(12) United States Patent
Bleck

(10) Patent No.: US 11,377,488 B2
(45) Date of Patent: Jul. 5, 2022

(54) MULTIFUNCTIONAL PROTEIN MOLECULES COMPRISING DECORIN AND USE THEREOF

(71) Applicant: CATALENT PHARMA SOLUTIONS, LLC, Somerset, NJ (US)

(72) Inventor: Gregory T. Bleck, Cross Plains, WI (US)

(73) Assignee: CATALENT PHARMA SOLUTIONS, LLC, Somerset, NJ (US)

( * ) Notice: Subject to any disclaimer, the term of this patent is extended or adjusted under 35 U.S.C. 154(b) by 175 days.

(21) Appl. No.: 16/457,045

(22) Filed: Jun. 28, 2019

(65) Prior Publication Data

US 2020/0010539 A1    Jan. 9, 2020

Related U.S. Application Data

(60) Provisional application No. 62/693,766, filed on Jul. 3, 2018.

(51) Int. Cl.
| | | |
|---|---|---|
| *C07K 16/22* | (2006.01) | |
| *C07K 14/47* | (2006.01) | |
| *C07K 16/28* | (2006.01) | |
| *A61P 35/00* | (2006.01) | |

(52) U.S. Cl.
CPC .............. *C07K 16/22* (2013.01); *A61P 35/00* (2018.01); *C07K 14/4725* (2013.01); *C07K 16/2818* (2013.01); *C07K 16/2827* (2013.01); *C07K 2317/24* (2013.01); *C07K 2317/56* (2013.01)

(58) Field of Classification Search
CPC ................ C07K 16/22; C07K 14/4725; C07K 16/2818; A61P 35/00
See application file for complete search history.

(56) References Cited

FOREIGN PATENT DOCUMENTS

| | | |
|---|---|---|
| CA | 3046452 | 6/2014 |
| CN | 1789424 | 6/2006 |
| WO | 2010/040508 | 4/2010 |
| WO | 2010/045506 | 4/2010 |
| WO | 2016/073879 | 5/2016 |
| WO | 2017/214706 | 12/2017 |
| WO | 2017/214707 | 12/2017 |
| WO | 2018/014260 | 1/2018 |
| WO | 2018/156649 | 8/2018 |
| WO | 2018/195386 | 10/2018 |

OTHER PUBLICATIONS

Jarvinen et al., Decorin: A Growth Factor Antagonist for Tumor Growth Inhibition, BioMed Research International, vol. 2015, Article ID 654765 (Year: 2015).*
Topalian et al., Immune Checkpoint Blockade: A Common Denominator Approach to Cancer Therapy, Cancer Cell 27, Publication Date: Apr. 13, 2015 (Year: 2015).*
Berger et al., Fusion protein technologies for biopharmaceuticals: Applications and challenges, mAbs 7:3, 456-460, Publication Date: May 1, 2015 (Year: 2015).*
Uniprot DCN sequence (https://www.uniprot.org/uniprot/P07585). (Year: 2021).*
Ruhland et al., The glycosaminoglycan chain of decorin plays an important role in collagen fibril formation at the early stages of fibrillogenesis, FEBS Journal, 274 (2007), 4246-4255, Publication Year: 2007 (Year: 2007).*
Bowie et al., Deciphering the Message in Protein Sequences: Tolerance to Amino Acid Substitutions, Science, 1990, 247:1306-1310 (Year: 1990).*
Burgess et al., Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue, J. of Cell Biol. 111:2129-2138, 1990 (Year: 1990).*
Lazar et al., Transforming Growth Factor ox: Mutation of Aspartic Acid 47 and Leucine 48 Results in Different Biological Activities, Mol. Cell. Biol., 8:1247-1252, 1988 (Year: 1988).*
Bork, Powers and pitfalls in sequence analysis: the 70% hurdle, Genome Research, 2000, 10:398-400 (Year: 2000).*
Jarvinen et al., Target-seeking antifibrotic compound enhances wound healing and suppresses scar formation in mice, PNAS, vol. 107, 50, 21671-21676, with Supporting Information (Year: 2015).*
Brinkmann et al., The making of bispecific antibodies, mAbs, vol. 9, No. 2, 182-212 (Year: 2017).*
International Search Report and Written Opinion, Int'l Patent Application No. PCT/US2019/039862, dated Sep. 20, 2019, 11 pages.
Kontermann, R. "Dual Targeting strategies with bispecific antibodies" MABS, vol. 4, No. 2, Mar. 1, 2012, pp. 182-197.
Corraliza-Gorjon, I. et al. "New Strategies Using Antibody Combinations to Increase Cancer Treatment Effectiveness" Frontiers in Immunology, vol. 8, Dec. 21, 2017, Luasanne, CH, 31 pages.
Lan, Y. et al. "Enhanced preclinical antitumor activity of m7824, a bifunctional fusion protein simultaneously targeting PD-L1 and TGF-beta" Sci. Transl. Med. Jan. 17, 2018, retrieved from the internet, 16 pages.
Hui Liang et al. "A collagen-binding EGFR antibody fragment targeting tumors with a collagen-rich extracellular matrix" Scientific Reports, vol. 6, No. 1, Feb. 17, 2016, 14 pages.
Sofeu Feugaing David Denis et al. "More than matrix: The multifaceted role of decorin in cancer" Europen Journal of Cell Biology, vol. 92, No. 1, Jan. 1, 2013, pp. 1-11.
Supplementary European Search Report, EP Patent Application No. 19830823.1, dated Mar. 16, 2022, 5 pages.

* cited by examiner (Continued)

*Primary Examiner* — Peter J Reddig
*Assistant Examiner* — Cheng Lu
(74) *Attorney, Agent, or Firm* — Cas; J. Mitchell Jones

(57) ABSTRACT

The present invention relates to multifunctional protein molecules comprising decorin and uses thereof. In particular, the present invention relates to multifunctional protein molecules comprising decorin and a targeting polypeptide such as an antibody and methods of their production and uses thereof.

16 Claims, 7 Drawing Sheets

Specification includes a Sequence Listing.

| Lane | RD | ID Number | Sample Description | Result |
|---|---|---|---|---|
| 10 | NA | NA | Noves Sharps STD | NA |
| 11 | RD151006 | 15-2784 | 2134- N. VI Pool – NR | See Gel |
| 12 | RD151006 | 15-2784 | 2134- N. VI Pool – R | See Gel |

MULTIFUNCTIONAL PROTEIN MOLECULES COMPRISING DECORIN AND USE THEREOF

This Applications claims priority to U.S. Provisional Application No. 62/693,766, filed Jul. 3, 2018, the entire contents of which are incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted on Jun. 28, 2019 and identified as follows: One 215,000 Byte ASCII (Text) file named "33890 ST25" created on Jun. 28, 2019.

FIELD OF THE INVENTION

The present invention relates to multifunction protein molecules comprising decorin and uses thereof. In particular, the present invention relates to multifunctional protein molecules comprising decorin and a targeting polypeptide such as an antibody and methods of their production and uses thereof.

BACKGROUND OF THE INVENTION

VEGF

Angiogenesis is the physiological process through which new blood vessels form from pre-existing vessels. This is distinct from vasculogenesis, which is the de novo formation of endothelial cells from mesoderm cell precursors. The first vessels in the developing embryo form through vasculogenesis, after which angiogenesis is responsible for most, if not all, blood vessel growth during development and in disease.

Angiogenesis is a normal and vital process in growth and development, as well as in wound healing and in the formation of granulation tissue. However, it is also a fundamental step in the transition of tumors from a benign state to a malignant one, leading to the use of angiogenesis inhibitors in the treatment of cancer.

Vascular endothelial growth factor (VEGF), originally known as vascular permeability factor (VPF), is a signal protein produced by cells that stimulates vasculogenesis and angiogenesis. It is part of the system that restores the oxygen supply to tissues when blood circulation is inadequate. Serum concentration of VEGF is high in bronchial asthma and diabetes mellitus. VEGF's normal function is to create new blood vessels during embryonic development, new blood vessels after injury, muscle following exercise, and new vessels (collateral circulation) to bypass blocked vessels.

When VEGF is overexpressed, it can contribute to disease. Solid cancers cannot grow beyond a limited size without an adequate blood supply; cancers that can express VEGF are able to grow and metastasize. Overexpression of VEGF can cause vascular disease in the retina of the eye and other parts of the body. Drugs such as bevacizumab and ranibizumab can inhibit VEGF and control or slow those diseases.

VEGF is a sub-family of growth factors, to be specific, the platelet-derived growth factor family of cystine-knot growth factors. They are important signaling proteins involved in both vasculogenesis (the de novo formation of the embryonic circulatory system) and angiogenesis (the growth of blood vessels from pre-existing vasculature).

Checkpoint Inhibitors

An important part of the immune system is its ability to tell between normal cells in the body and those it sees as "foreign." This lets the immune system attack the foreign cells while leaving the normal cells alone. To do this, it uses "checkpoints"—molecules on certain immune cells that need to be activated (or inactivated) to start an immune response. Cancer cells sometimes find ways to use these checkpoints to avoid being attacked by the immune system. But drugs that target these checkpoints hold a lot of promise as cancer treatments.

Checkpoint inhibitors seek to overcome one of cancer's main defenses against an immune system attack. Immune system T cells patrol the body constantly for signs of disease or infection. When they encounter another cell, they probe certain proteins on its surface, which serve as insignia of the cell's identity. If the proteins indicate the cell is normal and healthy, the T cell leaves it alone. If the proteins suggest the cell is infected or cancerous, the T cell will lead an attack against it. Once T cells initiate an attack, the immune system increases a series of additional molecules to prevent the attack from damaging normal tissues in the body. These molecules are known as immune checkpoints.

Checkpoint inhibitors block these normal proteins on cancer cells, or the proteins on T cells that respond to them. The result is to remove the blinders that prevented T cells from recognizing the cells as cancerous and leading an immune system assault on them. Three checkpoint inhibitors have received rapid approval from the U.S. Food and Drug Administration for cancer, including ipilimumab (Yervoy®), pembrolizumab (Keytruda®), and nivolumab (Opdivo®). These and other immune checkpoint therapies represent one of the most promising frontiers in cancer treatment today.

Additional therapeutic agents that target VEGF or immune checkpoints are needed.

SUMMARY OF THE INVENTION

The present invention relates to multifunction protein molecules comprising decorin and uses thereof. In particular, the present invention relates to multifunctional protein molecules comprising decorin and a targeting polypeptide such as an antibody and methods of their production and uses thereof.

Accordingly, in some embodiments, the present invention provides multifunctional protein molecules comprising at least one decorin molecule or functional portion thereof linked to an antigen binding protein.

In some preferred embodiments, the antigen binding protein is selected from the group consisting of a VEGF-A antigen binding protein and a checkpoint inhibitor antigen binding protein. In some preferred embodiments, the checkpoint inhibitor antigen binding protein binds a checkpoint inhibitor protein selected from the group consisting of PD-1, PD-L1, CTLA-4, PD-L2, CD27, CD28, CD40, CD47, CD115, CD122, CD137, OX40, GITR, ICOS, A2AR, B7-H3, B7-H4, BTLA, IDO, KIR, LAG3, NOX2, TIM-3, VISTA, SIGLEC-7, TIGIT and 4-1BB. In some particularly preferred embodiments, the checkpoint inhibitor antigen binding protein binds a checkpoint inhibitor protein selected from the group consisting of PD-1, PD-L1, CTLA-4, PD-L2.

In some preferred embodiments, the antigen binding protein is an antibody. In some preferred embodiments, the antibody is a monoclonal antibody. In some preferred embodiments, the monoclonal antibody is selected from the group consisting of bevacizumab, ranibizumab, ipilimumab, atezolizumab, avelumab, durvalumab, nivolumab and pembrolizumab.

In some preferred embodiments, the decorin polypeptide is a decorin core protein. In some preferred embodiments, the decorin core protein comprises a mutation at position 4 of the mature decorin core protein. In some preferred embodiments, the mutation is a serine to alanine mutation. In some preferred embodiments, the decorin core protein lacks substantial modification by glycosaminoglycans molecules at position 4 of the mature decorin core protein. In some preferred embodiments, the fusion protein comprises two or more copies of the decorin polypeptide.

In some preferred embodiments, the at least a functional portion of a decorin molecule comprises a decorin domain or domains that binds a signaling molecule selected from the group consisting of Transforming Growth Factor-β (TGF-β), Connective Tissue Growth Factor (CTGF), Platelet-Derived Growth Factor (PDGF), Vascular Endothelial Growth Factor Receptor 2 (VEGFR2), Hepatocyte Growth Factor Receptor (HGFR), Insulin-like Growth Factor 1 Receptor (IGF-1R), Epidermal Growth Factor Receptors (EGFRs), myostatin and C1q. In some preferred embodiments, the TGF-β binding domain comprises amino acids Asp45-Lys359 of full length endogenous human decorin or amino acids Leu155-Val260 of full length endogenous human decorin. In some preferred embodiments, the multifunctional protein molecule comprises two or more copies of the at least a functional portion of a decorin molecule.

In some preferred embodiments, the decorin molecule is operably linked to a heavy chain of the antibody. In some preferred embodiments, the antigen binding protein is bi-specific. In some preferred embodiments, the antigen binding protein is multi-specific.

In some preferred embodiments, the multifunctional protein molecule is a fusion protein. In some preferred embodiments, the decorin molecule is chemically linked to the antigen binding protein.

In some preferred embodiments, the present invention provides a nucleic acid or set of nucleic acids encoding a multifunctional protein molecule as described above. In some preferred embodiments, the present invention provides a vector or vectors comprising the nucleic acid or set of nucleic acids. In some preferred embodiments, the present invention provides a host cell comprising the vector or vectors.

In some preferred embodiments, the present invention provides methods of inhibiting a target protein and a signaling molecule in a cell, comprising: contacting the cell with the multifunctional protein molecule, nucleic acid molecule, or vector as described above under conditions such that at least one activity of the target protein and at least one activity of a signaling protein are inhibited in the cell, wherein the target protein is selected from the group consisting of VEGF-1, PD-1, PD-L1, CTLA-4, PD-L2, CD27, CD28, CD40, CD47, CD115, CD122, CD137, OX40, GITR, ICOS, A2AR, B7-H3, B7-H4, BTLA, IDO, KIR, LAG3, NOX2, TIM-3, VISTA, SIGLEC-7, TIGIT and 4-1BB. In some preferred embodiments, the cell is in vitro or in vivo. In some preferred embodiments, the cell is in a subject. In some preferred embodiments, the contacting results in inhibition of an activity selected from the group consisting of angiogenesis, PD-1 activity, PD-L1 activity, CTLA-4 activity, PD-L2 activity, CD27 activity, CD28 activity, CD40 activity, CD47 activity, CD115 activity, CD122 activity, CD137 activity, OX40 activity, GITR activity, ICOS activity, A2AR activity, B7-H3 activity, B7-H4 activity, BTLA activity, IDO activity, KIR activity, LAG3 activity, NOX2 activity, TIM-3 activity, VISTA activity, SIGLEC-7 activity, TIGIT activity and 4-1BB activity. In some preferred embodiments, the cancer is selected from the group consisting of lung cancer, colorectal cancer, liver cancer, breast cancer, kidney cancer, cervical cancer, ovarian cancer, and glioblastoma. In some preferred embodiments, the signaling protein is selected from the group consisting of Transforming Growth Factor-β (TGF-β), Connective Tissue Growth Factor (CTGF), Platelet-Derived Growth Factor (PDGF), Vascular Endothelial Growth Factor Receptor 2 (VEGFR2), Hepatocyte Growth Factor Receptor (HGFR), Insulin-like Growth Factor 1 Receptor (IGF-1R), various epidermal growth factor receptors (EGFRs), myostatin and C1q. In some preferred embodiments, the signaling protein is Transforming Growth Factor-β (TGF-β).

In some preferred embodiments, the present invention provides methods of treating a disorder characterized by angiogenesis or tumor growth, comprising: administering a multifunctional protein molecule, nucleic acid molecule, or vector as described above to a subject under conditions such that angiogenesis or tumor growth is inhibited in the subject. In some preferred embodiments, the tumor is selected from the group consisting of lung cancer, colorectal cancer, liver cancer, breast cancer, kidney cancer, cervical cancer, ovarian cancer, and glioblastoma.

DEFINITIONS

Figure 1:
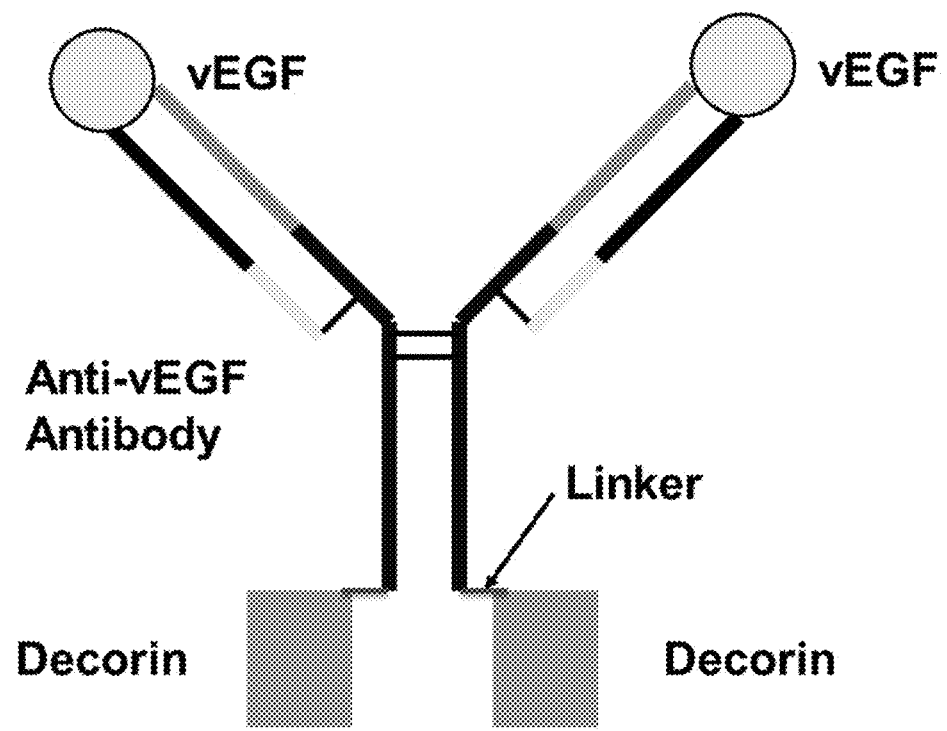
FIG. 1 is a schematic diagram of a fusion protein of the present invention.

To facilitate understanding of the invention, a number of terms are defined below.

As used herein, the term "decorin" refers to a protein molecule having a mature protein sequence that is at least 80% identical to SEQ ID NOs: 1, 2, or 6 or a portion thereof.

As used herein, the term "decorin core protein" refers to a decorin protein molecule that has a mutation at amino acid 4 of mature decorin and that substantially lacks modification with a glycosaminoglycan (GAG; i.e., is non-gagylated) at amino acid 4.

As used herein, the term "multifunctional protein molecule" refers to protein molecules that comprises two or more polypeptide sub-portions derived from at least two different sources. The multifunctional protein molecules may be recombinant fusion proteins encoded by a fusion gene or may be made by chemical addition (e.g., by covalent modification) of a polypeptide to another polypeptide. For example, fusion proteins of the present invention may preferably comprise one or more decorin molecules or functional portions thereof linked to an antigen binding protein via a linker sequence or may be "chemical fusions" wherein one or more decorin molecules or functional portions thereof are covalently linked to an antigen binding protein, for example, via a modified amino acid.

As used herein, the term "host cell" refers to any eukaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms "homology" and "percent identity" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid sequence and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "signal sequence" refers to any DNA sequence which, when operably linked to a recombinant DNA sequence, encodes a signal peptide which is capable of causing the secretion of the recombinant polypeptide. In general, the signal peptides comprise a series of about 15 to 30 hydrophobic amino acid residues (See, e.g., Zwizinski et al., J. Biol. Chem. 255(16): 7973-77 [1980], Gray et al., Gene 39(2): 247-54 [1985], and Martial et al., Science 205: 602-607 [1979]). Such secretion signal sequences are preferably derived from genes encoding polypeptides secreted from the cell type targeted for tissue-specific expression (e.g., secreted milk proteins for expression in and secretion from mammary secretory cells). Secretory DNA sequences, however, are not limited to such sequences. Secretory DNA sequences from proteins secreted from many cell types and organisms may also be used (e.g., the secretion signals for t-PA, serum albumin, lactoferrin, and growth hormone, and secretion signals from microbial genes encoding secreted polypeptides such as from yeast, filamentous fungi, and bacteria).

As used herein, the term "purified" refers to molecules, either nucleic or amino acid sequences, that are removed from their normal environment, isolated or separated. An "isolated nucleic acid sequence" is therefore a purified nucleic acid sequence. "Substantially purified" molecules are at least 60% free, preferably at least 75% free, and more preferably at least 90% free from other components with which they are normally associated.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, β, ϑ, γ, and μ, respectively.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" refers to the particular site on an antigen molecule to which an antibody binds.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences* of *Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W. H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

DETAILED DESCRIPTION OF THE INVENTION

The present invention relates to multifunctional molecules comprising a decorin molecule or functional portion thereof operably linked to an antigen binding protein such as an immunoglobulin molecule, truncated fragment of an antigen molecule, or a single chain antibody. In particular, the present invention relates to fusion polypeptides comprising decorin and a VEGF or immune checkpoint targeting polypeptide (preferably a checkpoint inhibitor) and methods of their production and uses thereof. Embodiments of the present invention provide fusion polypeptides comprising a decorin polypeptide fused to an antigen binding protein of interest, nucleic acids encoding such polypeptides, and uses thereof. Exemplary compositions and methods are described herein. The decorin utilized in the fusion molecules may be wild type decorin, decorin core protein, or functional portions of either of these proteins, such as the portion(s) that bind TGF-β, or other signaling molecules such as Connective Tissue Growth Factor (CTGF), Platelet-Derived Growth Factor (PDGF), Vascular Endothelial Growth Factor Receptor 2 (VEGFR2), Hepatocyte Growth Factor Receptor (HGFR), Insulin-like Growth Factor 1 Receptor (IGF-1R), various epidermal growth factor receptors (EGFRs), myostatin and C1q.

I. Decorin

In preferred embodiments, multifunctional protein molecules of the present invention comprise one or more decorin polypeptides or functional portions thereof. Decorin has been shown to suppress transforming growth factor-beta-induced expression of plasminogen activator inhibitor-1 (See e.g., Wahab et al., Biochem J. 2002 Mar. 15; 362(Pt 3): 643-649; herein incorporated by reference in its entirety). Transforming growth factor-beta (TGF-β) is a key mediator of extracellular matrix (ECM) accumulation in sclerotic kidney diseases such as diabetic nephropathy. While not being limited to a particular mechanism, it is contemplated that the combination of decorin and a VEGF binding protein will improve efficacy over the VEGF binding protein by itself, through inhibiting TGF-β activity in combination with the blockage of VEGF.

Native decorin is a glycoprotein with an attached glycosaminoglycan and an average molecular weight of 90-140 kD. In some preferred embodiments, the decorin is decorin core protein, i.e., a substantially non-gagylated decorin. In some embodiments, the decorin core protein comprises a mutation at amino acid 4 (i.e., the 4$^{th}$ amino acid from the N-terminus) of the mature decorin core protein molecule. In some embodiments, the mutation is a serine to alanine mutation. In some embodiments, the decorin core protein is at least 90%, 95%, 99% or 100% identical to SEQ ID NO:6 (mature decorin core protein), provided that that the decorin core protein comprises a mutation at amino acid 4 (i.e., the 4$^{th}$ amino acid from the N-terminus) of the mature decorin core protein molecule.

Decorin is commonly expressed as a pre-pro-protein. The present invention provides multifunctional protein molecules comprising an antigen binding protein in operable association with one or more decorin mature peptide sequences or functional portions thereof. In some embodiments, the decorin core protein portion of the fusion polypeptide is at least 90%, 95%, 99% or 100% identical to SEQ ID NO:6 (mature decorin core protein) or a functional portion thereof. In some embodiments, the decorin core protein comprises a mutation at amino acid 4 (i.e., the 4$^{th}$ amino acid from the N-terminus) of the mature decorin core protein molecule.

The present invention further provides nucleic acid sequences encoding fusion proteins, as well as vectors comprising the nucleic acid sequences. In some embodiments, the decorin core protein portion of the fusion polypeptide is at least 90%, 95%, 99% or 100% identical to SEQ ID NO:5 (mature decorin core protein), provided that that the decorin core protein comprises a mutation at amino acid 4 (i.e., the 4$^{th}$ amino acid from the N-terminus) of the mature decorin core protein molecule.

In some embodiments, the decorin molecule utilized in the multifunctional protein molecules may comprise one or more functional portions of the decorin molecule. Decorin molecules have a number of functional portions or domains, for example, those described in Järvinen and Prince, BioMed Research Int'l, Vol. 2015, Article ID 654765 (incorporated by reference herein in its entirety). In some preferred embodiments, the decorin functional portion binds to or otherwise interacts with Transforming Growth Factor-β (TGF-β), Connective Tissue Growth Factor (CTGF), Platelet-Derived Growth Factor (PDGF), Vascular Endothelial Growth Factor Receptor 2 (VEGFR2), Hepatocyte Growth Factor Receptor (HGFR), Insulin-like Growth Factor 1 Receptor (IGF-1R), various epidermal growth factor receptors (EGFRs), myostatin or C1q. Preferred decorin functional portions retain functional activity (such as binding to one of the signaling molecules just described) and are preferably at least 90%, 95%, 99% or 100% identical to the corresponding native decorin sequence. Preferred decorin functional portions are shorter than the full-length native decorin molecule, and for example, may be from 10 to 300 amino acid in length or from 10 to 120 amino acids in length. For example, the functional portion of the decorin molecule may be at least 90%, 95%, 99% or 100% identical to SEQ ID NO:64 (decorin TGF-β binding domain, ASP45-LYS359 of full length endogenous human decorin), SEQ ID NO:65 (two copies decorin TGF-β binding domain, ASP45-LYS359, separated by linker), SEQ ID NO:66 (decorin TGF-β binding domain, LEU155-VAL260 of full length endogenous human decorin), SEQ ID NO:67 (two copies decorin TGF-β binding domain, LEU155-VAL260, separated by linker).

Exemplary decorin polypeptides and method of purifying decorin are described, for example, in WO 2006038107; herein incorporated by reference in its entirety. Exemplary decorin nucleic acid and amino acid sequences are provided below and in FIGS. 1 and 2.

| SEQ ID NO. | Sequence |
| --- | --- |
| SEQ ID NO: 46<br>Decorin core protein | DEAAGIGPEVPDDRDEEPSLGPVCPERCQ<br>CHLRVVQCSDLGLDKVPKDLPPDTTLLD<br>LQNNKITEIKDGDFKNLKNLHALILVNNK<br>ISKVSPGAFTPLVKLERLYLSKNQLKELPE<br>KMPKTLQELRAHENEITKVRKVTFNGLN<br>QMIVIELGTNPLKSSGIENGAFQGMKKLS<br>YIRIADTNITSIPQGLPPSLTELHLDGNKIS<br>RVDAASLKGLNNLAKLGLSFNSISAVDN<br>GSLANTPHLRELHLDNNKLTRVPGGLAE<br>HKYIQVVYLHNNNISVVGSSDFCPPGHNT<br>KKASYSGVSLESNPVQYAVEIQPSTERCVY<br>VRSAIQLGNYK |
| SEQ ID NO: 47<br>Decorin propeptide | GPFQQRGLFDFMLE |
| SEQ ID NO: 48<br>Decorin propeptide | GGCCCGTTTCAACAGAGAGGCTTATTTG<br>ACTTTATGCTAGAA |
| SEQ ID NO : 49<br>Decorin core protein | GATGAGGCTGCAGGGATAGGCCCAGAA<br>GTTCCTGATGACCGCGACTTCGAGCCCT<br>CCCTAGGCCCAGTGTGCCCCTTCCGCTG<br>TCAATGCCATCTTCGAGTGGTCCAGTGT<br>TCTGATTTGGGTCTGGACAAAGTGCCA<br>AAGGATCTTCCCCCTGACACAACTCTGC<br>TAGACCTGCAAAACAACAAAATAACCG<br>AAATCAAAGATGGAGACTTTAAGAACC<br>TGAAGAACCTTCACGCATTGATTCTTGT<br>CAACAATAAAATTAGCAAAGTTAGTCC<br>TGGAGCATTTACACCTTTGGTGAAGTTG<br>GAACGACTTTATCTGTCCAAGAATCAG<br>CTGAAGGAATTGCCAGAAAAAATGCCC<br>AAAACTCTTCAGGAGCTGCGTGCCCAT<br>GAGAATGAGATCACCAAAGTGCGAAAA<br>GTTACTTTCAATGGACTGAACCAGATG<br>ATTGTCATAGAACTGGGCACCAATCCG<br>CTGAAGAGCTCAGGAATTGAAAATGGG<br>GCTTTCCAGGGAATGAAGAAGCTCTCC<br>TACATCCGCATTGCTGATACCAATATCA<br>CCAGCATTCCTCAAGGTCTTCCTCCTTC<br>CCTTACGGAATTACATCTTGATGGCAAC<br>AAAATCAGCAGAGTTGATGCAGCTAGC<br>CTGAAAGGACTGAATAATTTGGCTAAG<br>TTGGGATTGAGTTTCAACAGCATCTCTG<br>CTGTTGACAATGGCTCTCTGGCCAACAC<br>GCCTCATCTGAGGGAGCTTCACTTGGAC<br>AACAACAAGCTTACCAGAGTACCTGGT<br>GGGCTGGCAGAGCATAAGTACATCCAG<br>GTTGTCTACCTTCATAACAACAATATCT<br>CTGTAGTTGGATCAAGTGACTTCTGCCC<br>ACCTGGACACAACACCAAAAAGGCTTC<br>TTATTCGGGTGTGAGTCTTTTCAGCAAC<br>CCGGTCCAGTACTGGGAGATACAGCCA<br>TCCACCTTCAGATGTGTCTACGTGCGCT<br>CTGCCATTCAACTCGGAAACTATAAGT<br>GA |

-continued

| SEQ ID NO. | Sequence |
|---|---|
| SEQ ID NO: 64<br>Decorin TGF-β binding domain ASP45-LYS359 | DFEPSLGPVCPFRCQCHLRVVQCSDLGLDKV<br>PKDLPPDTTLLDLQNNKITEIKDGDFKNLKN<br>LHALILVNNKISKVSPGAFTPLVKLERLYLS<br>KNQLKELPEKMPKTLQELRAHENEITKVRKV<br>TFNGLNQMIVIELGTNPLKSSGIENGAFQGM<br>KKLSYIRIADTNITSIPQGLPPSLTELHLDG<br>NKISRVDAASLKGLNNLAKLGLSFNSISAVD<br>NGSLANTPHLRELHLDNNKLTRVPGGLAEHK<br>YIQVVYLHNNISVVGSSDFCPPGHNTKKAS<br>YSGVSLFSNPVQYWEIQPSTFRCVYVRSAIQ<br>LGNYK |
| SEQ ID NO: 65 Decorin TGF-β binding domain ASP45-LYS359, two copies separated by linker | DFEPSLGPVCPFRCQCHLRVVQCSDLGLDKV<br>PKDLPPDTTLLDLQNNKITEIKDGDFKNLKN<br>LHALILVNNKISKVSPGAFTPLVKLERLYLS<br>KNQLKELPEKMPKTLQELRAHENEITKVRKV<br>TFNGLNQMIVIELGTNPLKSSGIENGAFQGM<br>KKLSYIRIADTNITSIPQGLPPSLTELHLDG<br>NKISRVDAASLKGLNNLAKLGLSFNSISAVD<br>NGSLANTPHLRELHLDNNKLTRVPGGLAEHK<br>YIQVVYLHNNISVVGSSDFCPPGHNTKKAS<br>YSGVSLFSNPVQYWEIQPSTFRCVYVRSAIQ<br>LGNYK*SGGGGS*DFEPSLGPVCPFRCQCHLRV<br>VQCSDLGLDKVPKDLPPDTTLLDLQNNKITE<br>IKDGDFKNLKNLHALILVNNKISKVSPGAFT<br>PLVKLERLYLSKNQLKELPEKMPKTLQELRA<br>HENEITKVRKVTFNGLNQMIVIELGTNPLKS<br>SGIENGAFQGMKKLSYIRIADTNITSIPQGL<br>PPSLTELHLDGNKISRVDAASLKGLNNLAKL<br>GLSFNSISAVDNGSLANTPHLRELHLDNNKL<br>TRVPGGLAEHKYIQVVYLHNNISVVGSSDF<br>CPPGHNTKKASYSGVSLFSNPVQYWEIQPST<br>FRCVYVRSAIQLGNYK |
| SEQ ID NO: 66<br>Decorin TGF-β binding domain LEU155-VAL260 | LRAHENEITKVRKVTFNGLNQMIVIELGTNP<br>LKSSGIENGAFQGMKKLSYIRIADTNITSIP<br>QGLPPSLTELHLDGNKISRVDAASLKGLNNL<br>AKLGLSFNSISAV |
| SEQ ID NO: 67<br>Decorin TGF-β binding domain LEU155-VAL260<br>Two copies separated by linker | LRAHENEITKVRKVTFNGLNQMIVIELGTNP<br>LKSSGIENGAFQGMKKLSYIRIADTNITSIP<br>QGLPPSLTELHLDGNKISRVDAASLKGLNNL<br>AKLGLSFNSISAV*SGGGGS*LRAHENEITKVR<br>KVTFNGLNQMIVIELGTNPLKSSGIENGAFQ<br>GMKKLSYIRIADTNITSIPQGLPPSLTELHL<br>DGNKISRVDAASLKGLNNLAKLGLSFNSISA<br>V |

II. Binding Agents

Preferred embodiments of the present invention provide multifunctional protein molecules comprising a one or more decorin molecules or functional portion(s) thereof that are operably linked to a binding agent of interest. Preferred binding agents of interest include, but are not limited to, antigen binding proteins including immunoglobulins and fragments or derivatives thereof such as single chain antibodies that bind to molecules such as VEGF (Vascular endothelial growth factor) and checkpoint inhibitor proteins such as CTLA-4 (Cytotoxic T-lymphocyte antigen 4), PD-1 (Programmed cell death protein 1), PD-L1 (Programmed death-ligand 1), PD-L2 (Programmed death-ligand 2), CD27, CD28, CD40, CD47, CD115, CD122, CD137, OX40, GITR, ICOS, A2AR, B7-H3, B7-H4, BTLA, IDO, KIR, LAG3, NOX2, TIM-3, VISTA, SIGLEC-7, TIGIT and 4-1BB.

Binding agents (e.g., antigen binding proteins) generally interact with or bind specifically with a target. For example, the binding agents disclosed herein generally interact specifically with regions of, for example, VEGF, CTLA-4, PD-1 or PD-1, which are collectively referred to herein as target proteins. Binding "specifically" to a target protein means that the amount of binding to the target protein is more than the amount of binding to non-target protein targets (e.g., there may be background nonspecific binding). Generally, specific binding of binding agents to a protein, for example, may be achieved by binding to a specific sequence of amino acids within a protein target. These sequences may be referred to as epitopes. Molecules containing the epitopes may be used to stimulate binding agents like antibodies and may be referred to as immunogens. The binding agents may also recognize specific 2- and/or 3-dimensional structures as part of the epitope. Antigen binding protein may be monospecific, bi-specific, or multispecific.

The specific interaction or binding of a binding agent with its target is thought to be a type of equilibrium reaction. In one example, the specific binding can be quantified. The quantification may use a dissociation constant, or Kd is known in the art to be a type of equilibrium constant that describes the propensity of, in this case, an antibody to separate from the antigen or epitope to which it has bound. Thus, Kd describes the affinity that an antibody has for an epitope. The lower the Kd, the higher is the affinity of a binding agent for its target.

In certain embodiments, the binding agent is a monoclonal antibody. The antibody (e.g., monoclonal antibody) may also be of any suitable isotype or isotype subclass. The binding agent may also be a derivative of an antibody such as, for example, a Fab, F(ab')2, Fab' single chain antibody, Fv, single chain, mono-specific antibody, bi-specific antibody, tri-specific antibody, multi-valent antibody, chimeric antibody, humanized antibody, human antibody, shark antibody, nanobody (e.g., antibody comprising a single monomeric variable domain), camelid antibody (e.g., from the Camelidae family) microbody, intrabody (e.g., intracellular antibody), or de-fucosylated antibody and/or derivative thereof. Mimetics of binding agents and/or antibodies are also contemplated as being within the present invention. The binding agent may also comprise a detectable label and/or effector moiety attached thereto.

Where the binding agent is an antigen binding protein such as an immunoglobulin or derivative thereof, it may be identified with reference to the nucleotide and/or amino acid sequence corresponding to the variable and/or complementarity determining regions ("CDRs") thereof. For instance, an exemplary binding agent that is, is derived from, or is related to the monoclonal antibodies described herein may comprise a heavy and/or a light chain that each comprise one or more constant and/or variable regions. The variable regions typically comprise one or more CDRs that in large part determine the binding specificity of the antibody. These monoclonal antibodies may be identified by analysis of the nucleotide sequences encoding the variable regions. The monoclonal antibodies may also be identified by analysis of the amino acid sequences of (e.g., encoded by the nucleotide sequences) the variable regions.

The amino acids in the multifunctional protein molecules of the present invention may also be substituted by any other amino acid as desired by one of ordinary skill in the art. For example, one of skill in the art may make conservative substitutions by replacing particular amino acids with others as is known in the art. Any of the amino acid sequences of the antigen binding proteins described herein may also be combined with any other variable region and/or CDR in any order and/or combination to form hybrid and/or fusion binding agents and/or inserted into other heavy and/or light chain variable regions using standard techniques. These may be used in conjunction with any constant regions.

CDRs (complementarity-determining regions) are amino acid sequences from antibodies that are, at least in part, responsible for binding of an antibody to a specific target. It is understood by those of skill in the art that CDRs may be identified using any of several techniques and/or schemes. CDRs of the binding agents shown herein may be identified using any of these techniques. For instance, one of ordinary skill in the art may identify CDRs using the Kabat Numbering Scheme, the Chothia Numbering Scheme, the Enhanced Chothia Numbering Scheme, and/or any of the available CDR Definition Schemes (e.g., AbM, contact definition, and/or as described by MacCullum, et al., *J Mol. Biol.*, 262(5):732-745, 1996. A summary of various schemes, in part based on, for example, Kabat et al., "Sequences of Proteins of immunological Interest," 5th Ed., Public Health Service, National Institutes of Health, Bethesda, Md., NIH publication No. 91-3242 (1991), and Al-Lazikani et al., "Standard conformations for the canonical structures of immunoglobulins," J. Mol. Biol. 273:927-948, 1997, These systems for identifying CDRs are merely exemplary and others may be suitable, as would be understood by one of ordinary skill in the art. CDRs thus identified may be used to identify suitable binding agents. For instance, equivalents of one or more of the monoclonal antibodies described herein. Such CDRs may also be combined with one another in any order and/or combination to form hybrid and/or fusion binding agents and/or inserted into the other heavy and/or light chain variable regions using standard techniques.

In some embodiments, the CDR sequences from antigen binding proteins described herein are joined to the constant regions of any antibody molecule of the same or a different species (e.g., human, goat, rat, sheep, chicken) of that from which the variable region amino acid sequence was derived.

Deamidation of asparagine residues to aspartic acid or isoaspartic acid is a common post-translational modification to proteins. Deamidation may occur with higher frequency when the asparagine is part of an asparagine-glycine dipeptide (Asp-Gly or N-G; the "NG" sequence). Deamidation may have detrimental effects on proteins. In one example, deamidation may potentially cause a change in the three-dimensional structure of a protein. In another example, for an antibody, deamidation in a region that affects binding to an antigen (e.g., variable regions and/or CDRs) may potentially cause lower or loss of antibody binding to the antigen.

Accordingly, in some embodiments, amino acid residues potentially susceptible to post-translational deamidation are substituted with those less or not susceptible. In one example, asparagine and/or glycine is substituted to modify the NG sequence for example, any amino acid that eliminates the NG sequence.

The constant regions of antibodies are derived from any of, for example, human (e.g., IgG (IgG1, IgG2, IgG3, IgG4), IgM, IgA (IgA1 and IgA2), IgD, and IgE), canine (e.g., IgG (IgGA, IgGB, IgGC, IgGD) IgA, IgD, IgE, and IgM), chicken (e.g., IgA, IgD, IgE, IgG, IgM, IgY), goat (e.g., IgG), mouse (e.g., IgA, IgG, IgD, IgE, IgM), pig (e.g., IgA, IgG, IgD, IgE, IgM), rat (e.g., IgA, IgG, IgD, IgE, IgM), feline (e.g., IgA, IgD, IgE, IgG, IgM) and/or a fragment and/or derivative thereof (e.g., as chimeric antibodies).

In one example, the binding agents are antibodies that have modified glycosylation patterns. IgG molecules, for example, typically contain N-linked oligosaccharides. Some IgG molecules contain a biantennary complex-type oligosaccharide linked to the antibody heavy chain. In human IgG, the oligosaccharide is generally linked to an asparagine residue at position 297 (N297) of the heavy chain (in the constant Fc region of the antibody heavy chain). Generally, a fucose is attached to the GLcNAC residue in the oligosaccharide that is nearest to N297. Absence of the fucose may enhance the ability of the antibodies to mediate antibody-dependent cellular cytotoxicity (ADCC). It is contemplated that removal of the fucose enhances the ability of the antibody to interact with Fc receptors. Antibodies of this type are referred to as "defucosylated". Defucosylated antibodies may be produced using techniques described herein that may be known in the art. In some embodiments, a nucleic acid sequence encoding an antibody may be expressed in a cell line that has modified glycosylation abilities (e.g., deleted, modified or lesser amount of fucosyl transferase) and fail to add the typical fucose moieties. A variety of these cell lines are known. In some embodiments, the antibodies disclosed herein bind to VEGF but contain defucosylated oligosaccharides. The binding agents (e.g., antibodies) may include other modifications that may result in decreased interaction with Fc receptors. For instance, alternative or additional amino acid substitutions may be made to the antibody molecules described herein.

As described above, in some embodiments, the binding agents may be antibodies or immunoglobulins. The term "antibody" or "antibodies" may refer to whole or fragmented antibodies in unpurified or partially purified form (e.g., hybridoma supernatant, ascites, polyclonal antisera) or in purified form. A "purified" antibody may be one that is separated from at least about 50% of the proteins with which it is initially found (e.g., as part of a hybridoma supernatant or ascites preparation). A purified antibody may be one that is separated from at least about 60%, 75%, 90%, or 95% of the proteins with which it is initially found. Suitable derivatives may also be fragments (e.g., Fab, F(ab')2 or single chain antibodies, like Fv, for example). The antibodies may be of any suitable origin or form including, for example, murine (e.g., produced by murine hybridoma cells), or expressed as chimeric antibodies, and the like.

Methods of preparing and utilizing various types of antibodies are well-known to those of skill in the art and would be suitable in practicing the present invention (see, for example, Harlow, et al. Antibodies: A Laboratory Manual, Cold Spring Harbor Laboratory, 1988; Harlow, et al., Using Antibodies: A Laboratory Manual, Portable Protocol No. 1, 1998; Kohler and Milstein, Nature, 256:495, 1975; Jones et al., Nature, 321:522-525, 1986; Riechmann et al., Nature, 332:323-329, 1988; Presta, Curr. Op. Struct. Biol., 2:593-596, 1992; Verhoeyen et al., Science, 239:1534-1536, 1988; Hoogenboom et al., J Mol. Biol., 227:381, 1991; Marks et al., J Mol. Biol., 222:581, 1991; Cole et al., Monoclonal Antibodies and Cancer Therapy, Alan R. Liss, p. 77, 1985; Boerner et al., J Immunol., 147(1):86-95, 1991; Marks et al., BioiTechnology 10, 779-783, 1992; Lonberg et al., Nature 368:856-859, 1994; Morrison, Nature 368:812-13, 1994; Fishwild et al., Nature Biotechnology 14, 845-51, 1996; Neuberger, Nature Biotechnology 14, 826, 1996; Lonberg and Huszar, Intern. Rev. Immunol. 13:65-93, 1995; as well as U.S. Pat. Nos. 4,816,567, 5,545,807, 5,545,806, 5,569,825, 5,625,126, 5,633,425, and 5,661,016).

In some preferred embodiments, the antigen binding protein binds to a checkpoint inhibitor selected from the group consisting of PD-1, PD-L1, PD-L2, CTLA-4, CD27, CD28, CD40, CD47, CD115, CD122, CD137, OX40, GITR, ICOS, A2AR, B7-H3, B7-H4, BTLA, IDO, KIR, LAG3, NOX2, TIM-3, VISTA, SIGLEC-7, TIGIT and 4-1BB. In some embodiments, the antigen binding protein inhibits the activity of a checkpoint inhibitor selected from the group consisting of PD-1, PD-L1, PD-L2, CTLA-4, CD27, CD28, CD40, CD47, CD115, CD122, CD137, OX40, GITR, ICOS, A2AR, B7-H3, B7-H4, BTLA, IDO, KIR, LAG3, NOX2, TIM-3, VISTA, SIGLEC-7, TIGIT and 4-1BB. In some embodiments, the antibody is a commercially available human or humanized monoclonal antibody that targets VEGF (e.g., Bevacizumab (Avastin), Ranibizumab (Lucentis), or Pegaptanib (Macugen)) or an immune system checkpoint molecule such as CTLA-4 (e.g., Ipilimumab (Yervoy)), PD-L1 (e.g., Atezolizumab (Tecentriq), Avelumab (Bavencio), or Durvalumab (Imfinzi)) or PD-1 (e.g., Nivolumab (Opdivo) or Pembrolizumab (Keytruda)).

Bevacizumab (Avastin) is a recombinant humanized monoclonal antibody that blocks angiogenesis by inhibiting vascular endothelial growth factor A (VEGF-A). VEGF-A is a growth factor protein that stimulates angiogenesis in a variety of diseases, especially in cancer. Bevacizumab was the first available angiogenesis inhibitor in the United States.

Ipilimumab (Yervoy) is a monoclonal antibody that works to activate the immune system by targeting CTLA-4, a protein receptor that downregulates the immune system and is classified as checkpoint inhibitor drug. T lymphocytes can recognize and destroy cancer cells. However, an inhibitory mechanism interrupts this destruction. Ipilimumab turns off this inhibitory mechanism and allows the lymphocytes to continue to destroy cancer cells. Cancer cells produce antigens, which the immune system can use to identify them. These antigens are recognized by dendritic cells that present the antigens to cytotoxic T lymphocytes (CTLs) in the lymph nodes. The CTLs recognize the cancer cells by those antigens and destroy them. However, along with the antigens, the dendritic cells present an inhibitory signal. That signal binds to a receptor, cytotoxic T lymphocyte-associated antigen 4 (CTLA-4), on the CTL and turns off the cytotoxic reaction. This allows the cancer cells to survive. Ipilimumab binds to CTLA-4, blocking the inhibitory signal, which allows the CTLs to destroy the cancer cells.

Atezolizumab (Tecentriq) is a fully humanized, engineered monoclonal antibody of IgG1 isotype against the protein PD-L1. Avelumab (Bavencio) is a fully human monoclonal antibody that binds to PD-L1. Durvalumab (Imfinzi) is a fully human monoclonal antibody that binds to PD-L1. Together, these molecules may be referred to as PD-L1 inhibitors and are classified as immune checkpoint inhibitors. PD-L1 can be highly expressed on certain tumors, which leads to reduced activation of immune cells (cytotoxic T-cells in particular) that might otherwise recognize and attack the cancer. The PD-L1 checkpoint inhibitors block the interaction of PD-L1 with programmed cell death protein 1 (PD-1) and CD80 receptors (B7-1Rs). Inhibition of PD-L1 by removes the immune inhibitor effect and thereby engender an anti-tumor response.

Nivolumab (Opdivo) is human monoclonal antibody that binds to PD-1. Pembrolizumab (Keytruda) is a humanized antibody that binds to PD-1. Together, these molecules may be referred to as PD-1 inhibitors and are classified as immune checkpoint inhibitors. These molecules act by blocking a negative regulator of T-cell activation, thus allowing the immune system to attack the tumor. This is an example of immune checkpoint blockade. PD-1 is a protein on the surface of activated T cells. As discussed above, if PD-L1 or PD-L2 binds to PD-1, the T cell becomes inactive. Many cancer cells make PD-L1, which inhibits T cells from attacking tumors. Nivolumab blocks PD-L1 from binding to PD-1, allowing the T cell to work.

It will be understood by those of skill in the art that the CDRs or variable regions of the referenced antibodies may be isolated (e.g., by cloning) and grafted into other frameworks or antigen binding proteins derivatives (e.g., a Fab, a F(ab')2, a Fab' single chain antibody, a Fv single chain, bi-specific antibody, tri-specific antibody, multi-valent antibody, humanized antibody, nanobody, camelid antibody, microbody, or intrabody) as desired. This, the present invention encompasses antigen binding proteins that are derived from the reference antibodies and which are identified by the reference to the CDRs of variable regions of the reference antibodies. For example, in some preferred embodiments, the antigen binding proteins of the present invention comprise the heavy and light chain variable regions from Bevacizumab, Ranibizumab, Pegaptanib, Ipilimumab, Atezolizumab, Avelumab, Durvalumab, Nivolumab or Pembrolizumab. In other preferred embodiments, the antigen binding proteins comprise one, two or all three of CDR1, CDR2 and CDR3 from the heavy and light chain variable regions from Bevacizumab, Ranibizumab, Pegaptanib, Ipilimumab, Atezolizumab, Avelumab, Durvalumab, Nivolumab or Pembrolizumab.

III. Multifunctional Polypeptides

Embodiments of the present invention provide multifunctional polypeptides and/or polynucleotides encoding a fusion polypeptide comprising a decorin polypeptide operably linked to a binding agent. Compositions comprising these binding agents, polypeptides, peptides, polynucleotides, expression vectors, and/or host cells are also provided in some embodiments. In certain embodiments, the compositions comprise a pharmaceutically acceptable carrier.

Figure 2:
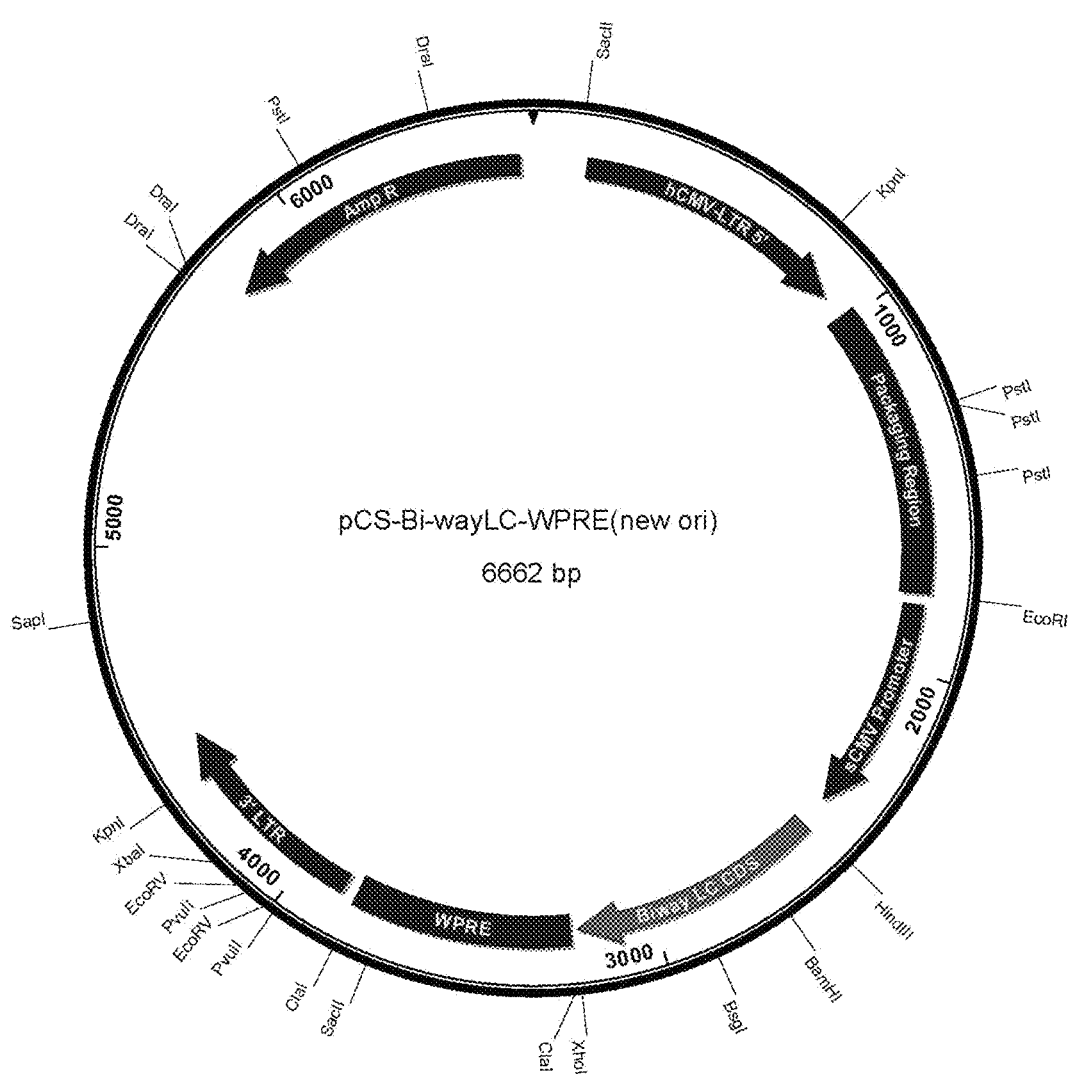
FIG. 2 is a map of an expression construct of the present invention.

In some preferred embodiments, the binding agent in the multifunctional protein molecule is an antibody as described above. A diagram of a decorin-antibody fusion of the present invention that targets VEGF is provided in FIG. 1. The skilled artisan will recognize that other antigen binding proteins described herein may be substituted for the VEGF antibody described in FIG. 1. Referring to FIG. 1, the fusion protein comprises the heavy and light chains of an antibody that binds to VEGF (e.g., Bevacizumab). A decorin molecule is operably linked to the C-terminal of each heavy chain via a peptide linker. The present invention is not limited to the use of any particular peptide linker, or to linkage of the decorin molecule to any particular amino acid of the antigen binding protein. In some preferred embodiments, the decorin molecule is linked via the C-terminal of either one or two of the antibody heavy chains, via the C-terminal of either one or two of the antibody light chains, via the N-terminal of either one or two of the antibody heavy chains, via the N-terminal of either one or two of the antibody light chains, or via an amino acid in the constant region of either one or two of the antibody heavy chains that is chemically modified to allow attachment of polypeptides such as the decorin molecule. Accordingly, the fusion proteins of the present invention may comprise one or preferably two decorin molecules or functional portions thereof and may comprise more than two decorin molecules or functional portions thereof.

A number of nucleic acid constructs encoding multifunctional protein molecules of the present invention are provided in the Examples. The following chart provides a summary of the sequences.

| | |
|---|---|
| SEQ ID NO: 1 | Bevacizumab-Decorin Fusion Heavy Chain Gene Sequence with Signal Sequence (SS) |
| SEQ ID NO: 2 | Bevacizumab-Decorin Fusion Heavy Chain Protein Sequence with SS |
| SEQ ID NO: 3 | Bevacizumab Light Chain Gene Sequence with SS |
| SEQ ID NO: 4 | Bevacizumab Light Chain Protein Sequence with SS |
| SEQ ID NO: 5 | Signal sequence for heavy and light chains |
| SEQ ID NO: 6 | Linker sequence between decorin and heavy chain |
| SEQ ID NO: 7 | Decorin |
| SEQ ID NO: 8 | Bevacizumab Heavy Chain Protein Sequence |
| SEQ ID NO: 9 | Bevacizumab Light Chain Protein Sequence |
| SEQ ID NO: 10 | Ipilimumab-Galacorin Fusion Heavy Chain Gene Sequence with SS |
| SEQ ID NO: 11 | Ipilimumab-Galacorin Fusion Heavy Chain Protein Sequence with SS |
| SEQ ID NO: 12 | Ipilimumab Light Chain Gene Sequence with SS |
| SEQ ID NO: 13 | Ipilimumab Light Chain Protein Sequence with SS |
| SEQ ID NO: 14 | Ipilimumab Heavy Chain Protein Sequence |
| SEQ ID NO: 15 | Ipilimumab Light Chain Protein Sequence |
| SEQ ID NO: 16 | Atezolizumab-Galacorin Fusion Heavy Chain Gene Sequence with SS |
| SEQ ID NO: 17 | Atezolizumab-Galacorin Fusion Heavy Chain Protein Sequence with SS |
| SEQ ID NO: 18 | Atezolizumab Light Chain Gene Sequence with SS |
| SEQ ID NO: 19 | Atezolizumab Light Chain Protein Sequence with SS |
| SEQ ID NO: 20 | Atezolizumab Heavy Chain Protein Sequence |
| SEQ ID NO: 21 | Atezolizumab Light Chain Protein Sequence |
| SEQ ID NO: 22 | Avelumab-Galacorin Fusion Heavy Chain Gene Sequence with SS |
| SEQ ID NO: 23 | Avelumab-Galacorin Fusion Heavy Chain Protein Sequence with SS |
| SEQ ID NO: 24 | Avelumab Light Chain Gene Sequence with SS |
| SEQ ID NO: 25 | Avelumab Light Chain Protein Sequence with SS |
| SEQ ID NO: 26 | Avelumab Heavy Chain Protein Sequence |
| SEQ ID NO: 27 | Avelumab Light Chain Protein Sequence |
| SEQ ID NO: 28 | Durvalumab-Galacorin Fusion Heavy Chain Gene Sequence with SS |
| SEQ ID NO: 29 | Durvalumab-Galacorin Fusion Heavy Chain Protein Sequence with SS |
| SEQ ID NO: 30 | Durvalumab Light Chain Gene Sequence with SS |
| SEQ ID NO: 31 | Durvalumab Light Chain Protein Sequence with SS |
| SEQ ID NO: 32 | Durvalumab Heavy Chain Protein Sequence |
| SEQ ID NO: 33 | Durvalumab Light Chain Protein Sequence |
| SEQ ID NO: 34 | Nivolumab-Galacorin Fusion Heavy Chain Gene Sequence with SS |
| SEQ ID NO: 35 | Nivolumab-Galacorin Fusion Heavy Chain Protein Sequence with SS |
| SEQ ID NO: 36 | Nivolumab Light Chain Gene Sequence with SS |
| SEQ ID NO: 37 | Nivolumab Light Chain Protein Sequence with SS |
| SEQ ID NO: 38 | Nivolumab Heavy Chain Protein Sequence |
| SEQ ID NO: 39 | Nivolumab Light Chain Protein Sequence |

| | |
|---|---|
| SEQ ID NO: 40 | Pembrolizumab-Galacorin Fusion Heavy Chain Gene Sequence with SS |
| SEQ ID NO: 41 | Pembrolizumab-Galacorin Fusion Heavy Chain Protein Sequence with SS |
| SEQ ID NO: 42 | Pembrolizumab Light Chain Gene Sequence with SS |
| SEQ ID NO: 43 | Pembrolizumab Light Chain Protein Sequence with SS |
| SEQ ID NO: 44 | Pembrolizumab Heavy Chain Protein Sequence |
| SEQ ID NO: 45 | Pembrolizumab Light Chain Protein Sequence |
| SEQ ID NO: 50 | Avelumab-Galacorin Fusion Heavy Chain Gene Sequence |
| SEQ ID NO: 51 | Avelumab-Galacorin Fusion Heavy Chain Protein Sequence |
| SEQ ID NO: 52 | Avelumab Light Chain Gene Sequence |
| SEQ ID NO: 53 | Avelumab Light Chain Protein Sequence |
| SEQ ID NO: 54 | Avelumab-Galacorin2x Fusion Heavy Chain Gene Sequence |
| SEQ ID NO: 55 | Avelumab-Galacorin2x Fusion Heavy Chain Protein Sequence |
| SEQ ID NO: 56 | Avelumab-Galacorin/Decorin (Asp45-Lys359 of full length endogenous human Decorin) TGF-Beta Binding Domains Fusion Heavy Chain Gene Sequence |
| SEQ ID NO: 57 | Avelumab-Galacorin/Decorin (Asp45-Lys359 of full length endogenous human Decorin) TGF-Beta Binding Domains Fusion Heavy Chain Protein Sequence |
| SEQ ID NO: 58 | Avelumab-Galacorin/Decorin (Asp45-Lys359 of full length endogenous human Decorin) TGF-Beta Binding Domains 2x Fusion Heavy Chain Gene Sequence |
| SEQ ID NO: 59 | Avelumab-Galacorin/Decorin (Asp45-Lys359 of full length endogenous human Decorin) TGF-Beta Binding Domains 2x Fusion Heavy Chain Protein Sequence |
| SEQ ID NO: 60 | Avelumab-Galacorin/Decorin (Leu155-Val260 of full length endogenous human Decorin) TGF-Beta Binding Domain Fusion Heavy Chain Gene Sequence |
| SEQ ID NO: 61 | Avelumab-Galacorin/Decorin (Leu155-Val260 of full length endogenous human Decorin) TGF-Beta Binding Domain Fusion Heavy Chain Protein Sequence |
| SEQ ID NO: 62 | Avelumab-Galacorin/Decorin (Leu155-Val260 of full length endogenous human Decorin) TGF-Beta Binding Domain 2x Fusion Heavy Chain Gene Sequence |
| SEQ ID NO: 63 | Avelumab-Galacorin/Decorin (Leu155-Val260 of full length endogenous human Decorin) TGF-Beta Binding Domain 2x Fusion Heavy Chain Protein Sequence |

Thus, in some preferred embodiments, the fusion proteins of the present invention comprise the heavy and light chain variable regions from Bevacizumab, Ranibizumab, Pegaptanib, Ipilimumab, Atezolizumab, Avelumab, Durvalumab, Nivolumab or Pembrolizumab operably linked to a decorin molecule, preferably a decorin core protein. In other preferred embodiments, the fusion proteins comprise one, two or all three of CDR1, CDR2 and CDR3 from the heavy and light chain variable regions from Bevacizumab, Ranibizumab, Pegaptanib, Ipilimumab, Atezolizumab, Avelumab, Durvalumab, Nivolumab or Pembrolizumab operably linked to a decorin molecule, preferably a decorin core protein.

In some preferred embodiments, the decorin molecule (or molecules if more than one copy is used) is decorin core protein having at least 80%, 90%, 95%, 99% or 100% identity to SEQ ID NO:7. In other preferred embodiments, the decorin molecule (or molecules if more than one copy is used) is a decorin TGF-β binding domain having at least 80%, 90%, 95%, 99% or 100% identity to SEQ ID NO:64 or 66. In some preferred embodiments, the decorin core protein inhibits the activity of TGF-β. In some preferred embodiments, the decorin core protein comprises one or more mutations that cause the decorin core protein to be non-gagylated. In some preferred embodiments, the decorin core protein comprises a mutation at amino acid 4 (i.e., the $4^{th}$ amino acid from the N-terminus) of the mature decorin core protein molecule. In some preferred embodiments, the decorin core protein molecule is linked to the heavy or light chain of a target antibody via a linker sequence. The present invention is not limited to any particular linker sequence. In some preferred embodiments, the linker sequence is SEQ ID NO:6. In some particularly preferred embodiments, the linker sequence is attached to the N-terminal of the heavy chain of the antibody and position between the heavy chain and the decorin core protein. Accordingly, in some preferred embodiments, the heavy chain fusion may be represented by the following formula:

Heavy chain protein-linker-decorin core protein

In other preferred embodiments, the fusions may represented by the following formulas:

C-terminal Heavy chain protein-linker-decorin

C-terminal Light chain protein-linker-decorin decorin-linker-N-terminal Heavy chain protein decorin-linker-N-terminal Light chain protein Constant region-linker-decorin wherein decorin may be wild-type decorin, decorin core protein, or a functional portion thereof as described in detail above and wherein the linkage is via amide bonds as in a fusion protein as is known in the art or or chemically modified amino acid in the N-terminal, C-terminal or constant region of the antigen binding protein. For example, aldehyde-tagged immunoglobulin (Ig) polypeptides can be converted by a formylglycine-generating enzyme to produce a 2-formylglycine (FGly)-modified Ig polypeptide. An FGly-modified Ig polypeptide can then be covalently and site-specifically bound to a moiety of interest to provide an Ig conjugate. See, e.g., U.S. Pat. No. 10,183,998, incorporated by reference herein in its entirety.

In some preferred embodiments, a secretion signal sequence precedes the heavy chain protein sequence to allow secretion from host cells during protein production. Likewise, in some preferred embodiments, a secretion signal sequence precedes the light chain protein sequence to allow secretion from host cells during protein production.

In some preferred embodiments, where the targeting molecule is Bevacizumab, the heavy chain sequence is at least 90%, 95%, 99% or 100% identical to SEQ ID NO:8 and the light chain sequence is at least 90%, 95%, 99% or 100% identical to SEQ ID NO:9. In some preferred embodiments, the targeting molecule binds to or inhibits VEGF-A.

In some preferred embodiments, where the targeting molecule is Ipilimumab, the heavy chain sequence is at least 90%, 95%, 99% or 100% identical to SEQ ID NO:14 and the light chain sequence is at least 90%, 95%, 99% or 100% identical to SEQ ID NO:15. In some preferred embodiments, the targeting molecule binds to or inhibits CTLA-4.

In some preferred embodiments, where the targeting molecule is Atezolizumab, the heavy chain sequence is at least 90%, 95%, 99% or 100% identical to SEQ ID NO:20 and the light chain sequence is at least 90%, 95%, 99% or 100% identical to SEQ ID NO:21. In some preferred embodiments, the targeting molecule binds to or inhibits PD-L1.

In some preferred embodiments, where the targeting molecule is Avelumab, the heavy chain sequence is at least 90%, 95%, 99% or 100% identical to SEQ ID NO:26 and the light chain sequence is at least 90%, 95%, 99% or 100% identical to SEQ ID NO:27. In some preferred embodiments, the targeting molecule binds to or inhibits PD-L1.

In some preferred embodiments, where the targeting molecule is Durvalumab, the heavy chain sequence is at least 90%, 95%, 99% or 100% identical to SEQ ID NO:32 and the light chain sequence is at least 90%, 95%, 99% or 100% identical to SEQ ID NO:33. In some preferred embodiments, the targeting molecule binds to or inhibits PD-L1.

In some preferred embodiments, where the targeting molecule is Nivolumab, the heavy chain sequence is at least 90%, 95%, 99% or 100% identical to SEQ ID NO:38 and the light chain sequence is at least 90%, 95%, 99% or 100% identical to SEQ ID NO:39. In some preferred embodiments, the targeting molecule binds to or inhibits PD-1.

In some preferred embodiments, where the targeting molecule is Pembrolizumab, the heavy chain sequence is at least 90%, 95%, 99% or 100% identical to SEQ ID NO:44 and the light chain sequence is at least 90%, 95%, 99% or 100% identical to SEQ ID NO:45. In some preferred embodiments, the targeting molecule binds to or inhibits PD-1.

In certain embodiments, preparations of fusion proteins are provided. Such preparations may comprise, for example, unpurified or purified fusion proteins. Typically, such preparations include a buffer such as phosphate- or tris-buffered saline (PBS or TBS, respectively). The preparations may also be formulated to contain excipients, like stabilizers, for example.

In some preferred embodiments, the present invention further provides nucleic acid expression constructs that encode the fusion proteins of the present invention. Accordingly, in some embodiments, the expression constructs encode the fusion protein sequences described above and are operably associated with additional nucleic acid sequences required for expression in the selected expression system.

In one example, nucleotide sequences encoding the fusion protein are constructed into a vector system, and then expressed in host cells. In one example, the host cells are cultured cells. In one example, the vector system is used in mammalian cultured cells under conditions where the fusion proteins are expressed.

The fusion polynucleotides of the present invention may be employed for producing fusion polypeptides by recombinant techniques. Thus, for example, the polynucleotide may be included in any one of a variety of expression vectors for expressing a polypeptide. In some embodiments of the present invention, vectors include, but are not limited to, retroviral vectors, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host. In some preferred embodiments, the vectors are retroviral vectors as described in U.S. Pat. Nos. 6,852,510 and 7,332,333 and U.S. pat. Publ. Nos. 200402335173 and 20030224415, all of which are incorporated herein by references in their entirety. In some especially preferred embodiments, the vectors are pseudotyped retroviral vectors.

In particular, some embodiments of the present invention provide recombinant constructs comprising one or more of the sequences as broadly described above. In some embodiments of the present invention, the constructs comprise a vector, such as a plasmid or viral vector, into which a sequence of the invention has been inserted, in a forward or reverse orientation. In still other embodiments, the heterologous structural sequence is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus-pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the E. coli S lac or trp, the phage lambda PL and PR, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by retroviral transduction, calcium phosphate transfection, DEAE-Dextran mediated transfection, or electroporation (See e.g., Davis et al. [1986] Basic Methods in Molecular Biology). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al. (1989) Molecular Cloning: A Laboratory Manual, Second Edition, Cold Spring Harbor, N.Y.

In some embodiments of the present invention, following transformation of a suitable host strain and growth of the host strain to an appropriate cell density in media, protein is secreted and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

Further embodiments provide kits including fusion proteins and optionally other components useful, necessary, or sufficient for using the fusion proteins (e.g., therapeutic, research, and screening applications). The fusion proteins of the kit may be provided in any suitable form, including frozen, lyophilized, or in a pharmaceutically acceptable buffer such as TBS or PBS.

The fusion proteins described herein and/or derivatives thereof may also be incorporated into compositions for use in vitro or in vivo. The antibody, fusion protein, or derivatives thereof may also be fixably attached to functional effector moieties such as cytotoxic drugs or toxins, or active fragments thereof such as diphtheria A chain, exotoxin A chain, ricin A chain, abrin A chain, curcin, crotin, phenomycin, enomycin, among others.

Functional moieties may also include radiochemicals. In one embodiment, the effector moieties may be fixably attached to the binding agents. In one example, the detectable labels are fixably attached to the binding agents by chemical bonds. In one example, the chemical bonds are covalent chemical bonds. In one example, the effector moieties are conjugated to the binding agents.

The fusion proteins described herein may be prepared as an injectable preparation, such as in suspension in a non-toxic parenterally acceptable diluent or solvent. Suitable vehicles and solvents that may be utilized include water, Ringer's solution, and isotonic sodium chloride solution, TBS and PBS, among others. The formulations may contain excipients, like stablizers, for example. In certain applications, the antibodies are suitable for use in vitro. In other applications, the antibodies are suitable for use in vivo. The preparations suitable for use in either case are well-known in the art and will vary depending on the particular application.

The fusion proteins may be combined with one or more pharmaceutically acceptable carriers prior to administration to a host. A pharmaceutically acceptable carrier is a material that is not biologically or otherwise undesirable, e.g., the material may be administered to a subject, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. Suitable pharmaceutical carriers and their formulations are described in, for example, *Remington s: The Science and Practice of Pharmacy, 2 yt Edition*, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose. The pH of the solution is generally from about 5 to about 8 or from about 7 to about 7.5. Other carriers include sustained-release preparations such as semipermeable matrices of solid hydrophobic polymers containing polypeptides or fragments thereof. Matrices may be in the form of shaped articles, e.g., films, liposomes or microparticles. It will be apparent to those persons skilled in the art that certain carriers may be more preferable depending upon, for instance, the route of administration and concentration of composition being administered. Carriers are those suitable for administration of polypeptides and/or fragments thereof to humans or other subjects.

Pharmaceutical compositions may also include carriers, thickeners, diluents, buffers, preservatives, surface active agents, adjuvants, immunostimulants, in addition to the fusion protein. Pharmaceutical compositions may also include one or more active ingredients such as antimicrobial agents, anti-inflammatory agents and anesthetics IV. Uses Embodiments of the present disclosure provide compositions and methods for research, screening, and therapeutic application. For example, embodiments of the present invention provide methods of treating a variety of diseases using the multifunctional protein molecules described herein.

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, and macular degeneration.

Some embodiments of the present invention provide methods for administering an effective amount of a fusion polypeptide of the invention and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In a particular embodiment, the additional therapeutic agent(s) is an anticancer agent.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anti-cancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of the invention and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. The Table below provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N'',-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co Inc Whitehouse Station, NJ |
| BCG Live (lyophilized preparation of an attenuated strain of Mycobacterium bovis (Bacillus Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by Streptomyces verticillus; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |

-continued

| | | |
|---|---|---|
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-l-triazeno)-imidazole-4-carboxamide (DTIC)) | DTIC-Dome | Bayer AG, Leverkusen, Germany |
| Dactinomycin, actinomycin D (actinomycin produced by Streptomyces parvullus, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |

| | | |
|---|---|---|
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperidinopiperidino)carbonyloxy]-1H-pyrano[3',4':6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |

| | | |
|---|---|---|
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Mechlorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |

| | | |
|---|---|---|
| Plicamycin, Mithramycin (antibiotic produced by Streptomyces plicatus) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b )-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo]5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine, 1,1',1"-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino[1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |

-continued

| | | |
|---|---|---|
| Vincristine (C$_{46}$H$_{56}$N$_4$O$_{10}$H$_2$SO$_4$) | Oncovin | Eli Lilly |
| Vinorelbine (3,4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724, 714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

In some embodiments of the present invention, a fusion protein of the invention and one or more therapeutic agents or anticancer agents are administered to an animal under one or more of the following conditions: at different periodicities, at different durations, at different concentrations, by different administration routes, etc.

Fusion proteins within the scope of this invention include all fusion proteins described herein wherein the fusion proteins of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than C12). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXPERIMENTAL

Example 1

Expression Constructs

This example describes the design of the expression constructs that are inserted into expression vectors for recombinant production of fusion proteins.

```
Anti-VEGF
Bevacizumab-Galacorin Fusion Heavy Chain Gene Sequence (SEQ ID NO: 1):
ATGATGTCCTTTGTCTCTCTGCTCCTGGTTGGCATCCTATTCCATGCCACCCAGGCCGAGGTGC

AGCTGGTGGAGTCTGGGGGAGGCTTGGTACAGCCTGGGGGGTCCCTGAGACTCTCCTGTGCAGC

CTCTGGATACACCTTTACCAACTATGGCATGAACTGGGTCCGCCAGGCTCCAGGGAAGGGGCTG

GAGTGGGTGGGCTGGATAAACACTTACACTGGTGAGCCAACATATGCAGCTGACTTCAAGCGCC

GGTTTACCTTCTCTTTGGACACCTCCAAGTCCACGGCCTATCTGCAAATGAACAGCCTGCGGGC

CGAGGACACGGCCGTATATTACTGTGCGAAATACCCCCACTACTACGGTAGTAGCCACTGGTAC

TTTGACGTGTGGGGCCAGGGAACCCTGGTCACCGTCTCCTCAGCCTCCACCAAGGGCCCATCGG
```

TCTTCCCCCTGGCACCCTCCTCCAAGAGCACCTCTGGGGGCACAGCGGCCCTGGGCTGCCTGGT

CAAGGACTACTTCCCCGAACCGGTGACGGTGTCGTGGAACTCAGGCGCCCTGACCAGCGGCGTG

CACACCTTCCCGGCTGTCCTACAGTCCTCAGGACTCTACTCCCTCAGCAGCGTGGTGACCGTGC

CCTCCAGCAGCTTGGGCACCCAGACCTACATCTGCAACGTGAATCACAAGCCCAGCAACACCAA

GGTGGACAAGAAAGTTGAGCCCAAATCTTGTGACAAAACTCACACATGCCCACCGTGCCCAGCA

CCTGAACTCCTGGGGGGACCGTCAGTCTTCCTCTTCCCCCCAAAACCCAAGGACACCCTCATGA

TCTCCCGGACCCCTGAGGTCACATGCGTGGTGGTGGACGTGAGCCACGAAGACCCTGAGGTCAA

GTTCAACTGGTACGTGGACGGCGTGGAGGTGCATAATGCCAAGACAAAGCCGCGGGAGGAGCAG

TACAACAGCACGTACCGGGTGGTCAGCGTCCTCACCGTCCTGCACCAGGACTGGCTGAATGGCA

AGGAGTACAAGTGCAAGGTCTCCAACAAAGCCCTCCCAGCCCCCATCGAGAAAACCATCTCCAA

AGCCAAAGGGCAGCCCCGAGAACCACAGGTGTACACCCTGCCCCCATCCCGGGAGGAGATGACC

AAGAACCAGGTCAGCCTGACCTGCCTGGTCAAAGGCTTCTATCCCAGCGACATCGCCGTGGAGT

GGGAGAGCAATGGGCAGCCGGAGAACAACTACAAGACCACGCCTCCCGTGCTGGACTCCGACGG

CTCCTTCTTCCTCTACAGCAAGCTCACCGTGGACAAGAGCAGGTGGCAGCAGGGGAACGTCTTC

TCATGCTCCGTGATGCATGAGGCTCTGCACAACCACTACACGCAGAAGAGCCTCTCCCTGTCTC

CCGGGAAA*TCCGGGGGTGGCGGATCC*GATGAGGCTCCAGGGATAGGCCCAGAAGTTCCTGATGA

CCGCGACTTCGAGCCCTCCCTAGGCCCAGTGTGCCCCTTCCGCTGTCAATGCCATCTTCGAGTG

GTCCAGTGTTCTGATTTGGGTCTGGACAAAGTGCCAAAGGATCTTCCCCCTGACACAACTCTGC

TAGACCTGCAAAACAACAAAATAACCGAAATCAAAGATGGAGACTTTAAGAACCTGAAGAACCT

TCACGCATTGATTCTTGTCAACAATAAAATTAGCAAAGTTAGTCCTGGAGCATTTACACCTTTG

GTGAAGTTGGAACGACTTTATCTGTCCAAGAATCAGCTGAAGGAATTGCCAGAAAAAATGCCCA

AAACTCTTCAGGAGCTGCGTGCCCATGAGAATGAGATCACCAAAGTGCGAAAAGTTACTTTCAA

TGGACTGAACCAGATGATTGTCATAGAACTGGGCACCAATCCGCTGAAGAGCTCAGGAATTGAA

AATGGGGCTTTCCAGGGAATGAAGAAGCTCTCCTACATCCGCATTGCTGATACCAATATCACCA

GCATTCCTCAAGGTCTTCCTCCTTCCCTTACGGAATTACATCTTGATGGCAACAAAATCAGCAG

AGTTGATGCAGCTAGCCTGAAAGGACTGAATAATTTGGCTAAGTTGGGATTGAGTTTCAACAGC

ATCTCTGCTGTTGACAATGGCTCTCTGGCCAACACGCCTCATCTGAGGGAGCTTCACTTGGACA

ACAACAAGCTTACCAGAGTACCTGGTGGGCTGGCAGAGCATAAGTACATCCAGGTTGTCTACCT

TCATAACAACAATATCTCTGTAGTTGGATCAAGTGACTTCTGCCCACCTGGACACAACACCAAA

AAGGCTTCTTATTCGGGTGTGAGTCTTTTCAGCAACCCGGTCCAGTACTGGGAGATACAGCCAT

CCACCTTCAGATGTGTCTACGTGCGCTCTGCCATTCAACTCGGAAACTATAAGTGA

Signal peptide coding sequence is shown in boldface type.
Heavy chain coding sequence is underlined with a straight
line. Linker coding sequence is shown in italics. Galacorin
coding sequence is underlined with a wavy line.

```
Bevacizumab-Galacorin Fusion Heavy Chain Protein Sequence (SEQ ID NO: 2):
MMSFVSLLLVGILFHATQAEVQLVESGGGLVQPGGSLRLSCAASGYTFTNYGMNWVRQAPGKGL

EWVGWINTYTGEPTYAADFKRRFTFSLDTSKSTAYLQMNSLRAEDTAVYYCAKYPHYYGSSHWY

FDVWGQGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCPPCPA

PELLGGPSVFLFPPKPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPREPQVYTLPPSREEMT

KNQVSLTCLVKGFYPSDIAVEWESNGQPENNYKTTPPVLDSDGSFFLYSKLTVDKSRWQQGNVF

SCSVMHEALHNHYTQKSLSLSPGKSGGGGSDEAAGIGPEVPDDRDFEPSLGPVCPFRCQCHLRV

VQCSDLGLDKVPKDLPPDTTLLDLQNNKITEIKDGDFKNLKNLHALILVNNKISKVSPGAFTPL

VKLERLYLSKNQLKELPEKMPKTLQELRAHENEITKVRKVTFNGLNQMIVIELGTNPLKSSGIE

NGAFQGMKKLSYIRIADTNITSIPQGLPPSLTELHLDGNKISRVDAASLKGLNNLAKLGLSFNS

ISAVDNGSLANTPHLRELHLDNNKLTRVPGGLAEHKYIQVVYLHNNNISVVGSSDFCPPGHNTK

KASYSGVSLFSNPVQYWEIQPSTFRCVYVRSAIQLGNYK
```

Signal peptide sequence is shown in boldface type. Heavy chain sequence is underlined with a straight line. Linker sequence is shown in italics. Galacorin sequence is underlined with a wavy line.

```
Bevacizumab Light Chain Gene
Sequence (SEQ ID NO: 3):
ATGATGTCCTTTGTCTCTCTGCTCCTGGTTGGCATCCTGTTCCATGCCAC

CCAGGCCGACATCCAGATGACCCAGTCTCCATCCTCCCTGTCTGCATCTG

TAGGAGACAGAGTCACCATCACTTGCAGTGCAAGTCAGGACATTAGCAAT

TATTTAAACTGGTATCAGCAGAAACCAGGGAAAGCTCCTAAGGTCCTGAT

CTATTTCACATCCAGTTTGCACTCAGGGGTCCCATCTAGGTTCAGTGGCA

GTGGATCTGGGACAGATTTCACTCTCACCATCAGCAGCCTGCAGCCTGAA

GATTTTGCAACTTATTACTGCCAACAGTATAGTACCGTGCCTTGGACGTT

CGGCCAAGGGACCAAGGTGGAAATCAAACGAACTGTGGCTGCACCATCTG

TCTTCATCTTCCCGCCATCTGATGAGCAGCTTAAGTCCGGAACTGCTAGC

GTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAG

AGCAGGACAGCAAGGACAGCACCTACAGCCTCAGCAGCACCCTGACGCTG

AGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGTT

AG
```

Signal peptide coding sequence is shown in boldface type.
Light chain coding sequence is underlined with a straight line.

```
Bevacizumab Light Chain Protein Sequence
(SEQ ID NO: 4):
MMSFVSLLLVGILFHATQADIQMTQSPSSLSASVGDRVTITCSASQDISN

YLNWYQQKPGKAPKVLIYFTSSLHSGVPSRFSGSGSGTDFTLTISSLQPE

DFATYYCQQYSTVPWTFGQGTKVEIKRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC
```

Signal peptide sequence is shown in boldface type. Light chain sequence is underlined with a straight line.
Component Amino Acid Sequences:

```
Signal sequence for heavy and light chains (SEQ ID NO: 5):
MMSFVSLLLVGILFHATQA Linker sequence between decorin and heavy chain (SEQ ID NO: 6):
SGGGGS Decorin (SEQ ID NO: 7):
DEAAGIGPEVPDDRDFEPSLGPVCPFRCQCHLRVVQCSDLGLDKVPKDLPPDTTLLDLQNNKIT

EIKDGDFKNLKNLHALILVNNKISKVSPGAFTPLVKLERLYLSKNQLKELPEKMPKTLQELRAH
```

-continued

ENEITKVRKVTFNGLNQMIVIELGTNPLKSSGIENGAFQGMKKLSYIRIADTNITSIPQGLPPS

LTELHLDGNKISRVDAASLKGLNNLAKLGLSFNSISAVDNGSLANTPHLRELHLDNNKLTRVPG

GLAEHKYIQVVYLHNNNISVVGSSDFCPPGHNTKKASYSGVSLFSNPVQYWEIQPSTFRCVYVR

SAIQLGNYK

Bevacizumab Heavy Chain Protein Sequence (SEQ ID NO: 8):
EVQLVESGGGLVQPGGSLRLSCAASGYTFTNYGMNWVRQAPGKGLEWVGWINTYTGEPTYAADF

KRRFTFSLDTSKSTAYLQMNSLRAEDTAVYYCAKYPHYYGSSHWYFDVWGQGTLVTVSSASTKG

PSVFPLAPSSKSTSGGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTYRVVSVLTVLHQDWL

NGKEYKCKVSNKALPAPIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCSVMHEALHNHYTQKSLS

LSPGK

Bevacizumab Light Chain Protein Sequence (SEQ ID NO: 9):
DIQMTQSPSSLSASVGDRVTITCSASQDISNYLNWYQQKPGKAPKVLIYFTSSLHSGVPSRFSG

SGSGTDFTLTISSLQPEDFATYYCQQYSTVPWTFGQGTKVEIKRTVAAPSVFIFPPSDEQLKSG

TASVVCLLNNFYPREAKVQWKVDNALQSGNSQESVTEQDSKDSTYSLSSTLTLSKADYEKHKVY

ACEVTHQGLSSPVTKSFNRGEC

Anti-CTLA4
Ipilimumab-Galacorin Fusion Heavy Chain Gene Sequence (SEQ ID NO: 10):
ATGATGTCCTTTGTCTCTCTGCTCCTGGTTGGCATCCTATTCCATGCCACCCAGGCCCAGGTGC

AGCTGGTGGAGTCCGGCGGCGGCGTCGTGCAGCCCGGCCGGTCCCTGCGGCTGTCCTGCGCCGC

CTCCGGCTTCACCTTCTCCTCCTACACCATGCACTGGGTGCGGCAGGCCCCCGGCAAGGGCCTG

GAGTGGGTGACTTTCATCTCCTACGACGGCAACAACAAGTACTACGCCGACTCCGTGAAGGGCC

GGTTCACCATCTCCCGCGACAACTCCAAGAACACCCTGTACCTGCAGATGAACTCCCTGCGGGC

CGAGGACACCGCCATCTACTACTGCGCCCGGACCGGCTGGCTGGGCCCCTTCGACTACTGGGGC

CAGGGCACCCTGGTGACCGTGTCCTCCGCCTCCACCAAGGGCCCATCGGTCTTCCCCCTGGCAC

CCTCTAGCAAGAGCACCTCTGGGGGCACAGCGGCCCTGGGCTGCCTGGTCAAGGACTACTTCCC

CGAACCGGTGACGGTGTCGTGGAACTCAGGCGCCCTGACCAGCGGCGTGCACACCTTCCCGGCT

GTCCTACAGTCCTCAGGACTCTACTCCCTCAGCAGCGTGGTGACCGTGCCCTCCAGCAGCTTGG

GCACCCAGACCTACATCTGCAACGTGAATCACAAGCCCAGCAACACCAAGGTGGACAAGCGGGT

TGAGCCCAAATCTTGTGACAAAACTCACACATGCCCACCGTGCCCAGCACCTGAACTCCTGGGG

GGACCGTCAGTCTTCCTCTTCCCCCCAAAACCCAAGGACACCCTCATGATCTCCCGGACCCCTG

AGGTCACATGCGTGGTGGTGGACGTGAGCCACGAAGACCCTGAGGTCAAGTTCAACTGGTACGT

GGACGGCGTGGAGGTGCATAATGCCAAGACAAAGCCGCGGGAGGAGCAGTACAACAGCACGTAC

CGTGTGGTCAGCGTCCTCACCGTCCTGCACCAGGACTGGCTGAATGGCAAGGAGTACAAGTGCA

AGGTCTCCAACAAAGCCCTCCCAGCCCCCATCGAGAAAACCATCTCCAAAGCCAAAGGGCAGCC

CCGAGAACCACAGGTGTACACCCTGCCTCCATCCCGCGATGAGCTGACCAAGAACCAGGTCAGC

CTGACCTGCCTGGTCAAAGGCTTCTATCCCAGCGACATCGCCGTGGAGTGGGAGAGCAATGGGC

AGCCGGAGAACAACTACAAGACCACGCCTCCCGTGCTGGACTCCGACGGCTCCTTCTTCCTCTA

TAGCAAGCTCACCGTGGACAAGAGCAGGTGGCAGCAGGGGAACGTCTTCTCATGCTCCGTGATG

CATGAGGCTCTGCACAACCACTACACGCAGAAGAGCCTCTCCCTGTCTCCTGGGAAA*TCCGGGG*

-continued

*GTGGCGGATCC*GATGAGGCTGCAGGGATAGGCCCAGAAGTTCCTGATGACCGCGACTTCGAGCC

CTCCCTAGGCCCAGTGTGCCCCTTCCGCTGTCAATGCCATCTTCGAGTGGTCCAGTGTTCTGAT

TTGGGTCTGGACAAAGTGCCAAAGGATCTTCCCCCTGACACAACTCTGCTAGACCTGCAAAACA

ACAAAATAACCGAAATCAAAGATGGAGACTTTAAGAACCTGAAGAACCTTCACGCATTGATTCT

TGTCAACAATAAAATTAGCAAAGTTAGTCCTGGAGCATTTACACCTTTGGTGAAGTTGGAACGA

CTTTATCTGTCCAAGAATCAGCTGAAGGAATTGCCAGAAAAAATGCCCAAAACTCTTCAGGAGC

TGCGTGCCCATGAGAATGAGATCACCAAAGTGCGAAAAGTTACTTTCAATGGACTGAACCAGAT

GATTGTCATAGAACTGGGCACCAATCCGCTGAAGAGCTCAGGAATTGAAAATGGGGCTTTCCAG

GGAATGAAGAAGCTCTCCTACATCCGCATTGCTGATACCAATATCACCAGCATTCCTCAAGGTC

TTCCTCCTTCCCTTACGGAATTACATCTTGATGGCAACAAAATCAGCAGAGTTGATGCAGCTAG

CCTGAAAGGACTGAATAATTTGGCTAAGTTGGGATTGAGTTTCAACAGCATCTCTGCTGTTGAC

AATGGCTCTCTGGCCAACACGCCTCATCTGAGGGAGCTTCACTTGGACAACAACAAGCTTACCA

GAGTACCTGGTGGGCTGGCAGAGCATAAGTACATCCAGGTTGTCTACCTTCATAACAACAATAT

CTCTGTAGTTGGATCAAGTGACTTCTGCCCACCTGGACACAACACCAAAAAGGCTTCTTATTCG

GGTGTGAGTCTTTTCAGCAACCCGGTCCAGTACTGGGAGATACAGCCATCCACCTTCAGATGTG

TCTACGTGCGCTCTGCCATTCAACTCGGAAACTATAAGTGA

Signal peptide coding sequence is shown in boldface type.
Heavy chain coding sequence is underlined with a straight line. Linker coding sequence is shown in italics. Galacorin coding sequence is underlined with a wavy line.

Ipilimumab-Galacorin Fusion Heavy Chain Protein Sequence (SEQ ID NO: 11):
MMSFVSLLLVGILFHATQAQVQLVESGGGVVQPGRSLRLSCAASGFTFSSYTMHWVRQAPGKGL

EWVTFISYDGNNKYYADSVKGRFTISRDNSKNTLYLQMNSLRAEDTAIYYCARTGWLGPFDYWG

QGTLVTVSSASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKRVEPKSCDKTHTCPPCPAPELLG

GPSVFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSRDELTKNQVS

LTCLVKGFYPSDIAVEWESNGQPENNYKTIPPVLDSDGSFFLYSKLTVDKSRWQQGNVFSCSVM

HEALHNHYTQKSLSLSPGK*SGGGGS*DEAAGIGPEVPDDRDFEPSLGPVCPFRCQCHLRVVQCSD

LGLDKVPKDLPPDTTLLDLQNNKITEIKDGDFKNLKNLHALILVNNKISKVSPGAFTPLVKLER

LYLSKNQLKELPEKMPKTLQELRAHENEITKVRKVTFNGLNQMIVIELGTNPLKSSGIENGAFQ

GMKKLSYIRIADTNITSIPQGLPPSLTELHLDGNKISRVDAASLKGLNNLAKLGLSFNSISAVD

NGSLANTPHLRELHLDNNKLTRVPGGLAEHKYIQVVYLHNNNISVVGSSDFCPPGHNTKKASYS

GVSLFSNPVQYWEIQPSTFRCVYVRSAIQLGNYK

Signal peptide sequence is shown in boldface type. Heavy chain sequence is underlined with a straight line. Linker sequence is shown in italics. Galacorin sequence is underlined with a wavy line.

Ipilimumab Light Chain Gene Sequence
(SEQ ID NO: 12):
ATGATGTCCTTTGTCTCTCTGCTCCTGGTTGGCATCCTATTCCATGCCAC

CCAGGCCGAGATCGTGCTGACCCAGTCCCCCGGCACCCTGTCCCTGTCCC

CCGGCGAGCGGGCCACCCTGTCCTGCCGGGCCTCCCAGTCCGTGGGCTCC

TCCTACCTGGCCTGGTACCAGCAGAAGCCCGGCCAGGCCCCCCGGCTGCT

GATCTACGGCGCCTTCTCCCGCGCCACCGGCATCCCCGACCGGTTCTCCG

GCTCCGGCTCCGGCACCGACTTCACCCTGACCATCTCCCGGCTGGAGCCC

GAGGACTTCGCCGTGTACTACTGCCAGCAGTACGGCTCCTCCCCCTGGAC

CTTCGGCCAGGGCACCAAGGTGGAGATCAAGCGAACTGTGGCTGCACCAT

CTGTCTTCATCTTCCCGCCATCTGATGAGCAGCTTAAGTCCGGAACTGCT

AGCGTTGTGTGCCTGCTGAATAACTTCTATCCCAGAGAGGCCAAAGTACA

GTGGAAGGTGGATAACGCCCTCCAATCGGGTAACTCCCAGGAGAGTGTCA

CAGAGCAGGACAGCAAGGACAGCACCTACAGCCTCAGCAGCACCCTGACG

CTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGT

GTTAG

Signal peptide coding sequence is shown in boldface type. Light chain coding sequence is underlined with a straight line.

Ipilimumab Light Chain Protein Sequence
(SEQ ID NO: 13):
MMSFVSLLLVGILFHATQAEIVLTQSPGTLSLSPGERATLSCRASQSVGS

SYLAWYQQKPGQAPRLLIYGAFSRATGIPDRFSGSGSGTDFTLTISRLEP

EDFAVYYCQQYGSSPWTFGQGTKVEIKRTVAAPSVFIFPPSDEQLKSGTA

SVVCLLNNFYPREAKVQWKVDNALQSGNSQESVTEQDSKDSTYSLSSTLT

LSKADYEKHKVYACEVTHQGLSSPVTKSFNRGEC

Signal peptide sequence is shown in boldface type. Light chain sequence is underlined with a straight line.
Component Amino Acid Sequences:

Signal sequence for heavy and light chains (SEQ ID NO: 5)
Linker sequence between decorin and heavy chain (SEQ ID NO: 6)
Decorin (SEQ ID NO: 7)
Ipilimumab Heavy Chain Protein Sequence (SEQ ID NO: 14):
QVQLVESGGGVVQPGRSLRLSCAASGFTFSSYTMHWVRQAPGKGLEWVTFISYDGNNKYYADSV

KGRFTISRDNSKNTLYLQMNSLRAEDTAIYYCARTGWLGPFDYWGQGTLVTVSSASTKGPSVFP

LAPSSKSTSGGTAALGCLVKDYFPEPVTVSWNSGALTSGVHTFPAVLQSSGLYSLSSVVTVPSS

SLGTQTYICNVNHKPSNTKVDKRVEPKSCDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALHNHYTQKSLSLSPGK

Ipilimumab Light Chain Protein Sequence (SEQ ID NO: 15):
EIVLTQSPGTLSLSPGERATLSCRASQSVGSSYLAWYQQKPGQAPRLLIYGAFSRATGIPDRFS

GSGSGTDFTLTISRLEPEDFAVYYCQQYGSSPWTFGQGTKVEIKRTVAAPSVFIFPPSDEQLKS

GTASVVCLLNNFYPREAKVQWKVDNALQSGNSQESVTEQDSKDSTYSLSSTLTLSKADYEKHKV

YACEVTHQGLSSPVTKSFNRGEC

Anti-PD-L1
Atezolizumab-Galacorin Fusion Heavy Chain Gene Sequence
(SEQ ID NO: 16):
ATGATGTCCTTTGTCTCTCTGCTCCTGGTTGGCATCCTATTCCATGCCACCCAGGCCGAGGTAC

AACTCGTGGAATCCGGCGGGGACTCGTCCAACCGGGTGGTAGTCTCAGGTTGAGCTGCGCTGC

GAGCGGTTTCACTTTCTCAGACTCATGGATTCATTGGGTGCGCCAAGCACCTGGAAAAGGGTTG

GAATGGGTTGCCTGGATCTCTCCTTACGGAGGTTCTACCTACTACGCTGATTCAGTAAAGGGGC

GGTTCACAATTTCAGCCGATACTTCCAAAAATACGGCTTACCTGCAAATGAACTCTTTGAGGGC

-continued

GGAGGATACGGCGGTCTACTACTGTGCACGCAGGCACTGGCCTGGAGGGTTCGATTATTGGGGT

CAAGGCACTTTGGTAACCGTATCCTCCGCTTCTACCAAAGGCCCATCAGTATTTCCTTTGGCTC

CCAGCTCTAAGTCCACTTCCGGTGGAACTGCCGCACTTGGATGTCTCGTCAAAGACTACTTTCC

TGAGCCGGTAACTGTGTCATGGAACTCCGGCGCCCTCACTAGCGGCGTCCATACATTTCCAGCG

GTTCTCCAGTCAAGTGGCCTCTACAGCCTGTCCAGTGTAGTTACTGTCCCGTCTTCTAGTCTGG

GAACGCAAACATATATTTGCAATGTGAATCATAAGCCTAGTAACACAAAAGTCGATAAAAAAGT

GGAGCCGAAAAGTTGTGACAAAACGCATACCTGTCCGCCTTGTCCGGCCCCCGAACTCTTGGGC

GGCCCATCAGTCTTTCTCTTCCCGCCCAAACCTAAGGACACGTTGATGATAAGTCGCACGCCCG

AGGTTACATGCGTCGTAGTCGATGTCAGCCACGAGGATCCGGAGGTAAAGTTTAACTGGTATGT

AGACGGAGTTGAAGTACACAACGCCAAAACTAAACCGAGAGAGGAGCAGTACGCATCAACCTAT

CGCGTAGTATCTGTATTGACGGTCCTTCACCAAGACTGGCTCAATGGGAAAGAATACAAGTGCA

AAGTTTCTAATAAAGCCCTCCCTGCACCAATCGAAAAGACTATTTCAAAAGCCAAAGGACAACC

AAGAGAACCACAAGTTTATACATTGCCACCTAGTCGCGAGGAGATGACTAAAAACCAAGTGTCC

CTTACTTGTCTCGTAAAGGGTTTCTATCCAAGCGACATAGCAGTTGAGTGGGAAAGTAATGGCC

AGCCGGAAAACAACTACAAGACGACCCCCCCGGTTCTCGACTCCGATGGATCATTCTTTTTGTA

TAGTAAACTCACAGTTGATAAGAGTCGATGGCAGCAGGGGAATGTTTTTTCTTGCTCTGTGATG

CACGAGGCGCTCCACAACCACTATACGCAAAAGTCCCTCAGCCTGAGCCCCGGGAAA*TCCGGG*

*GTGGCGGATCC*GATGAGGCTGCAGGGATAGGCCCAGAAGTTCCTGATGACCGCGACTTCGAGCC

CTCCCTAGGCCCAGTGTGCCCCTTCCGCTGTCAATGCCATCTTCGAGTGGTCCAGTGTTCTGAT

TTGGGTCTGGACAAAGTGCCAAAGGATCTTCCCCCTGACACAACTCTGCTAGACCTGCAAAACA

ACAAAATAACCGAAATCAAAGATGGAGACTTTAAGAACCTGAAGAACCTTCACGCATTGATTCT

TGTCAACAATAAAATTAGCAAAGTTAGTCCTGGAGCATTTACACCTTTGGTGAAGTTGGAACGA

CTTTATCTGTCCAAGAATCAGCTGAAGGAATTGCCAGAAAAAATGCCCAAAGTCTTCAGGAGC

TGCGTGCCCATGAGAATGAGATCACCAAAGTGCGAAAAGTTACTTTCAATGGACTGAACCAGAT

GATTGTCATAGAACTGGGCACCAATCCGCTGAAGAGCTCAGGAATTGAAAATGGGGCTTTCCAG

GGAATGAAGAAGCTCTCCTACATCCGCATTGCTGATACCAATATCACCAGCATTCCTCAAGGTC

TTCCTCCTTCCCTTACGGAATTACATCTTGATGGCAACAAAATCAGCAGAGTTGATGCAGGTAG

CCTGAAAGGACTGAATAATTTGGCTAAGTTGGGATTGAGTTTCAACAGCATCTCTGCTGTTGAC

AATGGCTCTCTGGCCAACACGCCTCATCTGAGGGAGCTTCACTTGGACAACAACAAGCTTACCA

GAGTACCTGGTGGGCTGGCAGAGCATAAGTACATCCAGGTTGTCTACCTTCATAACAACAATAT

CTCTGTAGTTGGATCAAGTGACTTCTGCCCACCTGGACACAACACCAAAAAGGCTTCTTATTCG

GGTGTGAGTCTTTTCAGCAACCCGGTCCAGTACTGGGAGATACAGCCATCCACCTTCAGATGTG

TCTACGTGCGCTCTGCCATTCAACTCGGAAACTATAAGTGA

Signal peptide coding sequence is shown in boldface type.
Heavy chain coding sequence is underlined with a straight line. Linker coding sequence is shown in italics. Galacorin coding sequence is underlined with a wavy line.

```
Atezolizumab-Galacorin Fusion Heavy Chain Protein Sequence (SEQ ID NO: 17):
MMSFVSLLLVGILFHATQAEVQLVESGGGLVQPGGSLRLSCAASGFTFSDSWIHWVRQAPGKGL

EWVAWISPYGGSTYYADSVKGRFTISADTSKNTAYLQMNSLRAEDTAVYYCARRHWPGGFDYWG

QGTLVTVSSASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDKTHTCPPCPAPELLG

GPSVFLFPPKPKDTLMISRTPEVTCVVVDVSHEDPEVKFNWYVDGVEVHNAKTKPREEQYASTY

RVVSVLTVLHQDWLNGKEYKCKVSNKALPAPIEKTISKAKGQPREPQVYTLPPSREEMTKNQVS

LTCLVKGFYPSDIAVEWESNGQPENNYKTIPPVLDSDGSFFLYSKLTVDKSRWQQGNVFSCSVM

HEALHNHYTQKSLSLSPGKSGGGGSDEAAGIGPEVPDDRDFEPSLGPVCPFRCQCHLRVVQCSD

LGLDKVPKDLPPDTTLLDLQNNKITEIKDGDFKNLKNLHALILVNNKISKVSPGAFTPLVKLER

LYLSKNQLKELPEKMPKTLQELRAHENEITKVRKVTFNGLNQMIVIELGTNPLKSSGIENGAFQ

GMKKLSYIRIADTNITSIPQGLPPSLTELHLDGNKISRVDAASLKGLNNLAKLGLSFNSISAVD

NGSLANTPHLRELHLDNNKLTRVPGGLAEHKYIQVVYLHNNNISVVGSSDFCPPGHNTKKASYS

GVSLFSNPVQYWEIQPSTFRCVYVRSAIQLGNYK
```

Signal peptide sequence is shown in boldface type. Heavy chain sequence is underlined with a straight line. Linker sequence is shown in italics. Galacorin sequence is underlined with a wavy line.

```
Atezolizumab Light Chain Gene Sequence
(SEQ ID NO: 18):
ATGATGTCCTTTGTCTCTCTGCTCCTGGTTGGCATCCTATTCCATGCCAC

CCAGGCCGACATTCAGATGACACAATCACCTAGCAGTCTGAGTGCGAGCG

TAGGTGATCGCGTAACGATTACCTGCAGGGCCTCTCAAGACGTGTCAACG

GCAGTGGCGTGGTACCAGCAGAAGCCTGGTAAAGCTCCTAAGCTCCTCAT

CTATTCAGCTTCCTTCTTGTATAGTGGAGTACCGTCAAGATTTTCCGGAA

GCGGATCAGGTACAGATTTTACTTTGACTATCAGTAGTTTGCAGCCAGAG

GATTTCGCTACATATTACTGTCAACAATATCTCTATCACCCTGCCACTTT

TGGACAAGGGACTAAAGTCGAAATAAAACGAACAGTGGCCGCACCAAGCG

TTTTTATCTTTCCCCCATCCGACGAGCAGTTGAAGAGCGGCACCGCGTCC

GTGGTCTGCCTGTTGAATAATTTCTATCCAAGGGAGGCAAAAGTGCAATG

GAAAGTTGATAATGCGCTTCAATCCGGAAACTCACAAGAATCAGTAACAG
```

```
AACAAGACTCTAAAGACAGTACATATTCTCTTAGTAGCACACTCACTCTT

TCAAAGGCTGACTATGAGAAACATAAAGTGTACGCTTGTGAAGTGACACA

TCAAGGTCTTAGCTCCCCAGTAACTAAGAGCTTTAATAGGGGCGAGTGCT

GA
```

Signal peptide coding sequence is shown in boldface type. Light chain coding sequence is underlined with a straight line.

```
Atezolizumab Light Chain Protein Sequence
(SEQ ID NO: 19):
MMSFVSLLLVGILFHATQADIQMTQSPSSLSASVGDRVTITCRASQDVST

AVAWYQQKPGKAPKLLIYSASFLYSGVPSRFSGSGSGTDFTLTISSLQPE

DFATYYCQQYLYHPATFGQGTKVEIKRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC
```

Signal peptide sequence is shown in boldface type. Light chain sequence is underlined with a straight line.
Component Amino Acid Sequences:

```
Signal sequence for heavy and light chains (SEQ ID NO: 5)
Linker sequence between decorin and heavy chain (SEQ ID NO: 6)
Decorin (SEQ ID NO: 7)
Atezolizumab Heavy Chain Protein Sequence (SEQ ID NO: 20):
EVQLVESGGGLVQPGGSLRLSCAASGFTFSDSWIHWVRQAPGKGLEWVAWISPYGGSTYYADSV

KGRFTISADTSKNTAYLQMNSLRAEDTAVYYCARRHWPGGFDYWGQGTLVTVSSASTKGPSVFP
```

LAPSSKSTSGGTAALGCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSVFLFPPKPKDTLMISR

TPEVTCVVVDVSHEDPEVKFNWYVDGVEVHNAKTKPREEQYASTYRVVSVLTVLHQDWLNGKEY

KCKVSNKALPAPIEKTISKAKGQPREPQVYTLPPSREEMTKNQVSLTCLVKGFYPSDIAVEWES

NGQPENNYKTIPPVLDSDGSFFLYSKLTVDKSRWQQGNVFSCSVMHEALHNHYTQKSLSLSPGK

Atezolizumab Light Chain Protein Sequence (SEQ ID NO: 21):
DIQMTQSPSSLSASVGDRVTITCRASQDVSTAVAWYQQKPGKAPKLLIYSASFLYSGVPSRFSG

SGSGTDFTLTISSLQPEDFATYYCQQYLYHPATFGQGTKVEIKRTVAAPSVFIFPPSDEQLKSG

TASVVCLLNNFYPREAKVQWKVDNALQSGNSQESVTEQDSKDSTYSLSSTLTLSKADYEKHKVY

ACEVTHQGLSSPVTKSFNRGEC

Anti-PD-L1
Avelumab-Galacorin Fusion Heavy Chain Gene Sequence (SEQ ID NO: 22):
ATGATGTCCTTTGTCTCTCTGCTCCTGGTTGGCATCCTATTCCATGCCACCCAGGCCGAGGTAC

AGCTTTTGGAGTCAGGCGGGGGGCTCGTCCAACCTGGGGGGTCACTCCGGTTGTCATGTGCTGC

CAGTGGCTTCACATTCTCATCTTACATTATGATGTGGGTTCGACAGGCCCCTGGGAAGGGGCTG

GAGTGGGTTTCCTCCATCTACCCCTCCGGGGGAATTACCTTCTATGCCGACACGGTAAAGGGTC

GCTTCACTATAAGTCGAGATAACAGCAAAAATACGCTGTATCTCCAGATGAACTCTCTCAGGGC

TGAGGACACAGCTGTATATTACTGCGCGCGGATTAAGTTGGGGACCGTCACAACAGTGGATTAC

TGGGGTCAAGGCACTCTGGTAACCGTATCCTCAGCATCCACCAAGGGCCCAAGTGTATTCCCGC

TGGCCCCTTCAAGTAAATCCACGTCTGGCGGCACAGCCGCTCTCGGTTGCCTGGTTAAGGACTA

CTTCCCAGAACCTGTCACTGTCAGTTGGAACTCAGGCGCATTGACATCTGGTGTCCATACATTC

CCCGCAGTCCTGCAAAGCTCTGGACTTTACAGTCTTAGTAGCGTAGTGACAGTCCCATCTTCAA

GTCTTGGGACCCAAACTTATATTTGCAACGTAAATCATAAACCCTCCAACACTAAAGTAGACAA

AAAAGTAGAGCCGAAATCTTGCGACAAAACGCATACATGCCCACCATGTCCCGCTCCGGAACTC

CTGGGCGGCCCGTCCGTTTTTCTCTTTCCCCCAAAGCCCAAGGATACGCTTATGATCAGCAGAA

CACCGGAAGTTACTTGTGTAGTCGTTGACGTGTCTCACGAAGATCCCGAAGTCAAATTTAATTG

GTATGTGGATGGCGTCGAAGTGCACAACGCAAAAACCAAACCCAGAGAGGAACAGTATAACAGC

ACGTATCGAGTGGTCTCCGTACTTACGGTCCTCCACCAGGACTGGTTGAATGGCAAGGAGTACA

AGTGCAAAGTGAGCAATAAAGCGTTGCCAGCCCCGATCGAAAAAACCATCAGCAAGGCCAAGGG

ACAGCCTAGAGAGCCGCAGGTTTACACCTTGCCGCCATCAAGGGATGAACTGACTAAAAACCAG

GTATCCCTGACCTGCCTGGTTAAGGGTTTTTACCCCAGTGATATAGCGGTTGAATGGGAGTCTA

ACGGGCAGCCAGAGAACAACTACAAAACGACACCTCCCGTTCTGGATTCCGATGGCAGCTTTTT

CTTGTATTCTAAACTCACCGTGGATAAATCCCGATGGCAGCAAGGCAACGTCTTCTCCTGCAGC

GTGATGCATGAAGCCTTGCACAACCACTATACCCAAAAGAGTCTCAGCCTGTCACCCGGGAAA*T*

*CCGGGGGTGGCGGATCC*GATGAGGCTGCAGGGATAGGCCCAGAAGTTCCTGATGACCGCGACTT

CGAGCCCTCCCTAGGCCCAGTGTGCCCCTTCCGCTGTCAATGCCATCTTCGAGTGGTCCAGTGT

TCTGATTTGGGTCTGGACAAAGTGCCAAAGGATCTTCCCCCTGACACAACTCTGCTAGACCTGC

AAAACAACAAAATAACCGAAATCAAAGATGGAGACTTTAAGAACCTGAAGAACCTTCACGCATT

GATTCTTGTCAACAATAAAATTAGCAAAGTTAGTCCTGGAGCATTTACACCTTTGGTGAAGTTG

GAACGACTTTATCTGTCCAAGAATCAGCTGAAGGAATTGCCAGAAAAAATGCCCAAAACTCTTC

-continued

AGGAGCTGCGTGCCCATGAGAATGAGATCACCAAAGTGCGAAAAGTTACTTTCAATGGACTGAA

CCAGATGATTGTCATAGAACTGGGCACCAATCCGCTGAAGAGCTCAGGAATTGAAAATGGGGCT

TTCCAGGGAATGAAGAAGCTCTCCTACATCCGCATTGCTGATACCAATATCACCAGCATTCCTC

AAGGTCTTCCTCCTTCCCTTACGGAATTACATCTTGATGGCAACAAAATCAGCAGAGTTGATGC

AGCTAGCCTGAAAGGACTGAATAATTTGGCTAAGTTGGGATTGAGTTTCAACAGCATCTCTGCT

GTTGACAATGGCTCTCTGGCCAACACGCCTCATCTGAGGGAGCTTCACTTGGACAACAACAAGC

TTACCAGAGTACCTGGTGGGCTGGCAGAGCATAAGTACATCCAGGTTGTCTACCTTCATAACAA

CAATATCTCTGTAGTTGGATCAAGTGACTTCTGCCCACCTGGACACAACACCAAAAAGGCTTCT

TATTCGGGTGTGAGTCTTTTCAGCAACCCGGTCCAGTACTGGGAGATACAGCCATCCACCTTCA

GATGTGTCTACGTGCGCTCTGCCATTCAACTCGGAAACTATAAGTGA

Signal peptide coding sequence is shown in boldface type. Heavy chain coding sequence is underlined with a straight line. Linker coding sequence is shown in italics. Galacorin coding sequence is underlined with a wavy line.

Avelumab-Galacorin Fusion Heavy Chain Protein Sequence
(SEQ ID NO: 23):
MMSFVSLLLVGILFHATQAEVQLLESGGGLVQPGGSLRLSCAASGFTFSSYIMMWVRQAPGKGL

EWVSSIYPSGGITFYADTVKGRFTISRDNSKNTLYLQMNSLRAEDTAVYYCARIKLGTVTTVDY

WGQGTLVTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTVDKSRWQQGNVFSCS

VMHEALHNHYTQKSLSLSPGK*SGGGGS*DEAAGIGPEVPDDRDFEPSLGPVCPFRCQCHLRVVQC

SDLGLDKVPKDLPPDTTLLDLQNNKITEIKDGDFKNLKNLHALILVNNKISKVSPGAFTPLVKL

ERLYLSKNQLKELPEKMPKTLQELRAHENEITKVRKVTFNGLNQMIVIELGTNPLKSSGIENGA

FQGMKKLSYIRIADTNITSIPQGLPPSLTELHLDGNKISRVDAASLKGLNNLAKLGLSFNSISA

VDNGSLANTPHLRELHLDNNKLTRVPGGLAEHKYIQVVYLHNNNISVVGSSDFCPPGHNTKKAS

YSGVSLFSNPVQYWEIQPSTFRCVYVRSAIQLGNYK

Signal peptide sequence is shown in boldface type. Heavy chain sequence is underlined with a straight line. Linker sequence is shown in italics. Galacorin sequence is underlined with a wavy line.

Avelumab Light Chain Gene Sequence
(SEQ ID NO: 24):
ATGGATGTCCTTTGTCTCTCTGCTCCTGGTTGGCATCCTATTCCATGCCAC

CCAGGCCCAGTCTGCACTTACACAACCGGCGTCCGTTTCCGGATCTCCAG

GACAGAGCATTACTATCAGTTGCACGGGAACCTCCTCAGACGTAGGGGGG

TATAATTATGTGTCTTGGTATCAACAGCATCCCGGGAAAGCCCCCAAACT

GATGATCTACGATGTCAGCAATAGACCAAGCGGTGTGAGTAATCGATTTA

GCGGGTCTAAATCTGGTAACACAGCATCCCTCACTATTAGTGGACTGCAA

GCAGAAGATGAGGCAGACTATTATTGCAGTAGCTATACGTCTAGTTCCAC

```
CCGCGTTTTTGGCACTGGGACGAAAGTCACCGTTCTCGGACAACCAAAAG

CAAACCCCACCGTGACTCTGTTTCCGCCTAGCAGCGAAGAATTGCAGGCC

AATAAGGCGACACTCGTATGCCTTATCTCCGACTTCTACCCGGGCGCTGT

GACAGTCGCGTGGAAAGCCGACGGCAGCCCTGTTAAAGCTGGAGTCGAGA

CCACGAAGCCGTCCAAGCAGAGTAACAATAAGTATGCTGCATCCAGTTAT

CTCTCTCTCACTCCGGAACAGTGGAAGTCCCATCGGTCCTATAGTTGCCA

AGTGACCCATGAGGGTTCCACCGTAGAGAAAACGGTAGCACCTACCGAAT

GTAGTTGA
```

Signal peptide coding sequence is shown in boldface type. Light chain coding sequence is underlined with a straight line.

```
Avelumab Light Chain Protein Sequence
(SEQ ID NO: 25):
MMSFVSLLLVGILFHATQAQSALTQPASVSGSPGQSITISCTGTSSDVGG

YNYVSWYQQHPGKAPKLMIYDVSNRPSGVSNRFSGSKSGNTASLTISGLQ

AEDEADYYCSSYTSSSTRVFGTGTKVTVLGQPKANPTVTLFPPSSEELQA

NKATLVCLISDFYPGAVTVAWKADGSPVKAGVETTKPSKQSNNKYAASSY

LSLTPEQWKSHRSYSCQVTHEGSTVEKTVAPTECS
```

Signal peptide sequence is shown in boldface type. Light chain sequence is underlined with a straight line.

Component Amino Acid Sequences:

```
Signal sequence for heavy and light chains (SEQ ID NO: 5)
Linker sequence between decorin and heavy chain (SEQ ID NO: 6)
Decorin (SEQ ID NO: 7)
Avelumab Heavy Chain Protein Sequence (SEQ ID NO: 26):
EVQLLESGGGLVQPGGSLRLSCAASGFTFSSYIMMWVRQAPGKGLEWVSSIYPSGGITFYADTV

KGRFTISRDNSKNTLYLQMNSLRAEDTAVYYCARIKLGTVTTVDYWGQGTLVTVSSASTKGPSV

FPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSP

GK

Avelumab Light Chain Protein Sequence (SEQ ID NO: 27):
QSALTQPASVSGSPGQSITISCTGTSSDVGGYNYVSWYQQHPGKAPKLMIYDVSNRPSGVSNRF

SGSKSGNTASLTISGLQAEDEADYYCSSYTSSSTRVFGTGTKVTVLGQPKANPTVTLFPPSSEE

LQANKATLVCLISDFYPGAVTVAWKADGSPVKAGVETTKPSKQSNNKYAASSYLSLTPEQWKSH

RSYSCQVTHEGSTVEKTVAPTECS

Anti-PD-L1
Durvalumab-Galacorin Fusion Heavy Chain Gene Sequence (SEQ ID NO: 28):
ATGATGTCCTTTGTCTCTCTGCTCCTGGTTGGCATCCTATTCCATGCCACCCAGGCCGAGGTCC

AGCTTGTTGAAAGCGGTGGTGGCCTCGTGCAGCCTGGTGGCAGTTTGCGGTTGTCTTGCGCAGC

TAGTGGTTTTACCTTCTCCAGATACTGGATGTCATGGGTCCGACAGGCCCCTGGCAAGGGGCTT

GAATGGGTTGCAAATATAAAGCAGGACGGTTCTGAAAAGTACTATGTAGACTCCGTCAAAGGAA

GATTTACTATTAGTCGAGACAACGCCAAGAATAGCCTCTACCTTCAGATGAATTCTTTGCGAGC

GGAGGACACAGCCGTATATTACTGCGCACGAGAAGGGGGGTGGTTCGGTGAACTGGCTTTTGAC

TACTGGGGCAAGGTACGCTTGTCACGGTGAGCTCTGCCTCTACAAAGGGGCCGTCTGTGTTTC

CACTTGCTCCATCTAGTAAGTCAACTTCTGGAGGTACTGCGGCATTGGGATGCCTTGTTAAGGA

TTATTTTCCCGAACCTGTAACTGTGAGCTGGAATTCAGGTGCCCTCACCTCTGGTGTACATACC

TTTCCAGCAGTTTTGCAATCTTCCGGTTTGTACTCTCTTAGTTCAGTTGTAACTGTCCCCTCTT

CCTCTCTTGGTACCCAAACATACATTTGTAATGTCAATCACAAACCAAGCAATACCAAGGTAGA

CAAGCGGGTGGAACCCAAATCTTGTGACAAAACTCATACCTGCCCACCATGTCCCGCCCCGGAG

TTTGAAGGAGGTCCAAGTGTATTTCTTTTCCCGCCTAAGCCTAAGGATACCCTCATGATAAGTC

GGACACCAGAGGTGACGTGTGTTGTGGTAGACGTGAGTCACGAAGATCCCGAAGTTAAATTTAA
```

-continued

TTGGTATGTGGACGGGGTGGAAGTCCATAACGCGAAGACAAAGCCACGCGAAGAGCAGTACAAT

TCCACGTACAGGGTGGTTAGCGTGCTTACCGTCCTGCATCAAGATTGGCTGAACGGGAAAGAAT

ACAAATGCAAAGTATCCAACAAGGCGTTGCCTGCGAGTATCGAGAAAACGATTTCTAAAGCTAA

AGGACAACCCCGGGAACCCCAGGTCTATACACTGCCGCCCAGCAGAGAAGAGATGACGAAAAAT

CAAGTATCCCTTACGTGTCTCGTCAAAGGCTTCTACCCTTCCGATATTGCTGTAGAGTGGGAAT

CTAACGGGCAGCCGGAAAATAACTACAAGACTACTCCGCCAGTACTTGATTCAGACGGCTCCTT

CTTCCTTTATTCAAAACTCACCGTAGATAAAAGTAGGTGGCAACAAGGTAATGTTTTTAGCTGT

AGCGTAATGCACGAAGCGTTGCATAACCATTATACACAGAAATCACTCAGCCTGTCCCCCGGGA

AATCCGGGGGTGGCGGATCCGATGAGGCTGCAGGGATAGGCCCAGAAGTTCCTGATGACCGCGA

CTTCGAGCCCTCCCTAGGCCCAGTGTGCCCCTTCCGCTGTCAATGCCATCTTCGAGTGGTCCAG

TGTTCTGATTTGGGTCTGGACAAAGTGCCAAAGGATCTTCCCCCTGACACAACTCTGCTAGACC

TGCAAAACAACAAAATAACCGAAATCAAAGATGGAGACTTTAAGAACCTGAAGAACCTTCACGC

ATTGATTCTTGTCAACAATAAAATTAGCAAAGTTAGTCCTGGAGCATTTACACCTTTGGTGAAG

TTGGAACGACTTTATCTGTCCAAGAATCAGCTGAAGGAATTGCCAGAAAAAATGCCCAAAACTC

TTCAGGAGCTGCGTGCCCATGAGAATGAGATCACCAAAGTGCGAAAAGTTACTTTCAATGGACT

GAACCAGATGATTGTCATAGAACTGGGCACCAATCCGCTGAAGAGCTCAGGAATTGAAAATGGG

GCTTTCCAGGGAATGAAGAAGCTCTCCTACATCCGCATTGCTGATACCAATATCACCAGCATTC

CTCAAGGTCTTCCTCCTTCCCTTACGGAATTACATCTTGATGGCAACAAAATCAGCAGAGTTGA

TGCAGCTAGCCTGAAAGGACTGAATAATTTGGCTAAGTTGGGATTGAGTTTCAACAGCATCTCT

GCTGTTGACAATGGCTCTCTGGCCAACACGCCTCATCTGAGGGAGCTTCACTTGGACAACAACA

AGCTTACCAGAGTACCTGGTGGGCTGGCAGAGCATAAGTACATCCAGGTTGTCTACCTTCATAA

CAACAATATCTCTGTAGTTGGATCAAGTGACTTCTGCCCACCTGGACACAACACCAAAAAGGCT

TCTTATTCGGGTGTGAGTCTTTTCAGCAACCCGGTCCAGTACTGGGAGATACAGCCATCCACCT

TCAGATGTGTCTACGTGCGCTCTGCCATTCAACTCGGAAACTATAAGTGA

Signal peptide coding sequence is shown in boldface type. Heavy chain coding sequence is underlined with a straight line. Linker coding sequence is shown in italics. Galacorin coding sequence is underlined with a wavy line.

Durvalumab-Galacorin Fusion Heavy Chain Protein Sequence (SEQ ID NO: 29):

MMSFVSLLLVGILFHATQAEVQLVESGGGLVQPGGSLRLSCAASGFTFSRYWMSWVRQAPGKGL

EWVANIKQDGSEKYYVDSVKGRFTISRDNAKNSLYLQMNSLRAEDTAVYYCAREGGWFGELAFD

YWGQGTLVTVSSASTKGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKRVEPKSCDKTHTCPPCPAPE

FEGGPSVFLFPPKPKDTLMISRTPEVTCVVVDVSHEDPEVKFNWYVDGVEVHNAKTKPREEQYN

STYRVVSVLTVLHQDWLNGKEYKCKVSNKALPASIEKTISKAKGQPREPQVYTLPPSREEMTKN

QVSLTCLVKGFYPSDIAVEWESNGQPENNYKTTPPVLDSDGSFFLYSKLTVDKSRWQQGNVFSC

SVMHEALHNHYTQKSLSLSPGK*SGGGGS*DEAAGIGPEVPDDRDFEPSLGPVCPFRCQCHLRVVQ

CSDLGLDKVPKDLPPDTTLLDLQNNKITEIKDGDFKNLKNLHALILVNNKISKVSPGAFTPLVK

LERLYLSKNQLKELPEKMPKTLQELRAHENEITKVRKVTFNGLNQMIVIELGTNPLKSSGIENG

AFQGMKKLSYIRIADTNITSIPQGLPPSLTELHLDGNKISRVDAASLKGLNNLAKLGLSFNSIS

AVDNGSLANTPHLRELHLDNNKLTRVPGGLAEHKYIQVVYLHNNNISVVGSSDFCPPGHNTKKA

SYSGVSLFSNPVQYWEIQPSTFRCVYVRSAIQLGNYK

Signal peptide sequence is shown in boldface type. Heavy chain sequence is underlined with a straight line. Linker sequence is shown in italics. Galacorin sequence is underlined with a wavy line.

Durvalumab Light Chain Gene Sequence
(SEQ ID NO: 30):
ATGATGTCCTTTGTCTCTCTGCTCCTGGTTGGCATCCTATTCCATGCCAC
CCAGGCCGAGATAGTTTTGACTCAAAGCCCTGGAACGCTCTCTTTGTCTC
CCGGCGAGCGGGCGACCCTTTCCTGTAGGGCTAGCCAGAGGGTATCTTCC
TCTTACCTGGCATGGTACCAGCAAAAGCCCGGACAAGCCCCCCGACTTCT
GATTTATGACGCCTCATCCCGGGCGACAGGCATCCCTGACCGATTTTCAG
GGAGTGGCTCTGGTACCGATTTTACGCTTACGATTTCCAGGCTGGAGCCC
GAGGATTTCGCAGTGTATTACTGTCAACAATACGGCAGCTTGCCCTGGAC
CTTTGGACAAGGAACCAAGGTAGAGATCAAAAGGACCGTTGCCGCCCCGT
CCGTGTTCATCTTCCCTCCGAGCGATGAGCAACTTAAAAGTGGAACTGCA
AGCGTTGTATGTCTTCTGAACAATTTCTATCCCCGAGAAGCCAAGGTACA
GTGGAAAGTGGATAATGCCCTCCAATCTGGCAATAGCCAAGAGTCTGTCA CAGAGCAGGACAGCAAGGACTCAACTTATTCACTTAGCTCCACCCTGACG
CTGAGTAAAGCAGACTACGAGAAGCATAAGGTGTATGCTTGTGAGGTTAC
ACACCAAGGCTTGTCTTCTCCTGTCACGAAGTCTTTCAATAGGGGCGAAT
GCTGA Signal peptide coding sequence is shown in boldface type. Light chain coding sequence is underlined with a straight line.

Durvalumab Light Chain Protein Sequence
(SEQ ID NO: 31):
MMSFVSLLLVGILFHATQAEIVLTQSPGTLSLSPGERATLSCRASQRVSS
SYLAWYQQKPGQAPRLLIYDASSRATGIPDRFSGSGSGTDFTLTISRLEP
EDFAVYYCQQYGSLPWTFGQGTKVEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC Signal peptide sequence is shown in boldface type. Light chain sequence is underlined with a straight line.
Component Amino Acid Sequences:

```
Signal sequence for heavy and light chains (SEQ ID NO: 5)
Linker sequence between decorin and heavy chain (SEQ ID NO: 6)
Decorin (SEQ ID NO: 7)
Durvalumab Heavy Chain Protein Sequence (SEQ ID NO: 32):
EVQLVESGGGLVQPGGSLRLSCAASGFTFSRYWMSWVRQAPGKGLEWVANIKQDGSEKYYVDSV

KGRFTISRDNAKNSLYLQMNSLRAEDTAVYYCAREGGWFGELAFDYWGQGTLVTVSSASTKGPS

VFPLAPSSKSTSGGTAALGCLVKDYFPEPVTVSWNSGALTSGVHTFPAVLQSSGLYSLSSVVTV

PSSSLGTQTYICNVNHKPSNTKVDKRVEPKSCDKTHTCPPCPAPEFEGGPSVFLFPPKPKDTLM

ISRTPEVTCVVVDVSHEDPEVKFNWYVDGVEVHNAKTKPREEQYNSTYRVVSVLTVLHQDWLNG

KEYKCKVSNKALPASIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHEALHNHYTQKSLSLS

PGK

Durvalumab Light Chain Protein Sequence (SEQ ID NO: 33):
EIVLTQSPGTLSLSPGERATLSCRASQRVSSSYLAWYQQKPGQAPRLLIYDASSRATGIPDRFS

GSGSGTDFTLTISRLEPEDFAVYYCQQYGSLPWTFGQGTKVEIKRTVAAPSVFIFPPSDEQLKS
```

-continued

GTASVVCLLNNFYPREAKVQWKVDNALQSGNSQESVTEQDSKDSTYSLSSTLTLSKADYEKHKV

YACEVTHQGLSSPVTKSFNRGEC

Anti-PD-1
Nivolumab-Galacorin Fusion Heavy Chain Gene Sequence
(SEQ ID NO: 34):
ATGATGTCCTTTGTCTCTCTGCTCCTGGTTGGCATCCTATTCCATGCCACCCAGGCCCAAGTCC

AGCTCGTGGAATCAGGAGGGGGTGTAGTCCAACCAGGGCGGAGCCTCCGACTTGATTGTAAAGC

ATCAGGAATTACATTTTCTAATAGCGGAATGCATTGGGTCCGACAAGCGCCAGGCAAGGGACTG

GAATGGGTCGCGGTGATATGGTATGATGGATCAAAACGCTATTATGCGGACTCTGTGAAGGGTC

GATTCACTATTAGCAGAGATAACAGCAAGAATACTCTCTTCCTTCAGATGAATTCACTTAGGGC

AGAGGACACAGCGGTGTACTATTGCGCGACGAACGACGATTATTGGGGCCAAGGGACATTGGTA

ACGGTGAGTTCTGCTAGTACTAAAGGGCCTTCCGTCTTCCCACTCGCCCCTTGTTCTAGAAGTA

CTAGTGAGTCAACAGCTGCTTTGGGTTGCTTGGTTAAAGACTACTTTCCTGAACCCGTGACTGT

GTCTTGGAATTCCGGTGCTCTTACTTCAGGTGTTCATACATTCCCAGCAGTATTGCAGAGCTCT

GGCTTGTATTCTCTCCTCAGTGGTGACAGTACCTTCCTCCTCTCTTGGCACAAAAACTTACA

CATGTAATGTAGACCATAAACCATCAAACACGAAAGTTGACAAGAGAGTAGAAAGCAAGTATGG

GCCTCCATGTCCCCCGTGCCCGGCGCCCGAGTTCCTGGGTGGTCCGTCAGTGTTCTTGTTCCCT

CCCAAGCCAAAAGATACATTGATGATAAGTCGGACGCCGGAGGTCACATGTGTAGTAGTTGATG

TCTCTCAGGAGGATCCTGAGGTGCAGTTTAACTGGTACGTCGATGGTGTTGAGGTACACAACGC

CAAAACTAAGCCGAGGGAAGAGCAGTTCAATTCAACATATCGGGTCGTGTCCGTATTGACAGTT

CTGCACCAAGATTGGTTGAACGGAAAAGAGTATAAGTGCAAAGTTAGCAATAAGGGACTTCCGT

CCTCAATTGAAAAAACCATTTCCAAAGCGAAAGGCCAACCTCGGGAACCTCAGGTATATACCTT

GCCACCCAGCCAAGAAGAAATGACTAAAAACCAGGTTAGTTTGACATGTTTGGTTAAAGGCTTT

TACCCGTCCGACATTGCCGTCGAGTGGGAAAGCAATGGGCAGCCTGAAAATAACTACAAGACAA

CCCCACCAGTATTGGATTCCGACGGTTCCTTCTTTCTTTACAGCCGCCTCACCGTCGATAAGAG

TCGGTGGCAAGAGGGGAATGTCTTTTCCTGTAGTGTCATGCACGAAGCACTTCACAACCATTAC

ACCCAAAAATCATTGTCCCTGTCACTGGGGAAA*TCCGGGGGTGGCGGATCC*GATGAGGCTGCAG

GGATAGGCCCAGAAGTTCCTGATGACCGCGACTTCGAGCCCTCCCTAGGCCCAGTGTGCCCCTT

CCGCTGTCAATGCCATCTTCGAGTGGTCCAGTGTTCTGATTTGGGTCTGGACAAAGTGCCAAAG

GATCTTCCCCCTGACACAACTCTGCTAGACCTGCAAAACAACAAAATAACCGAAATCAAAGATG

GAGACTTTAAGAACCTGAAGAACCTTCACGCATTGATTCTTGTCAACAATAAAATTAGCAAAGT

TAGTCCTGGAGCATTTACACCTTTGGTGAAGTTGGAACGACTTTATCTGTCCAAGAATCAGCTG

AAGGAATTGCCAGAAAAAATGCCCAAAACTCTTCAGGAGCTGCGTGCCCATGAGAATGAGATCA

CCAAAGTGCGAAAAGTTACTTTCAATGGACTGAACCAGATGATTGTCATAGAACTGGGCACCAA

TCCGCTGAAGAGCTCAGGAATTGAAAATGGGCTTTCCAGGGAATGAAGAAGCTCTCCTACATC

CGCATTGCTGATACCAATATCACCAGCATTCCTCAAGGTCTTCCTCCTTCCCTTACGGAATTAC

ATCTTGATGGCAACAAAATCAGCAGAGTTGATGCAGCTAGCCTGAAAGGACTGAATAATTTGGC

TAAGTTGGGATTGAGTTTCAACAGCATCTCTGCTGTTGACAATGGCTCTCTGGCCAACACGCCT

```
-continued
CATCTGAGGGAGCTTCACTTGGACAACAACAAGCTTACCAGAGTACCTGGTGGGCTGGCAGAGC

ATAAGTACATCCAGGTTGTCTACCTTCATAACAACAATATCTCTGTAGTTGGATCAAGTGACTT

CTGCCCACCTGGACACAACACCAAAAAGGCTTCTTATTCGGGTGTGAGTCTTTTCAGCAACCCG

GTCCAGTACTGGGAGATACAGCCATCCACCTTCAGATGTGTCTACGTGCGCTCTGCCATTCAAC

TCGGAAACTATAAGTGA
```

Signal peptide coding sequence is shown in boldface type. Heavy chain coding sequence is underlined with a straight line. Linker coding sequence is shown in italics. Galacorin coding sequence is underlined with a wavy line.

```
Nivolumab-Galacorin Fusion Heavy Chain Protein Sequence
(SEQ ID NO: 35):
MMSFVSLLLVGILFHATQAQVQLVESGGGVVQPGRSLRLDCKASGITFSNSGMHWVRQAPGKGL

EWVAVIWYDGSKRYYADSVKGRFTISRDNSKNTLFLQMNSLRAEDTAVYYCATNDDYWGQGTLV

TVSSASTKGPSVFPLAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPPCPAPEFLGGPSVFLFP

PKPKDTLMISRTPEVTCVVVDVSQEDPEVQFNWYVDGVEVHNAKTKPREEQFNSTYRVVSVLTV

LHQDWLNGKEYKCKVSNKGLPSSIEKTISKAKGQPREPQVYTLPPSQEEMTKNQVSLTCLVKGF

YPSDIAVEWESNGQPENNYKTTPPVLDSDGSFFLYSRLTVDKSRWQEGNVFSCSVMHEALHNHY

TQKSLSLSLGKSGGGGSDEAAGIGPEVPDDRDFEPSLGPVCPFRCQCHLRVVQCSDLGLDKVPK

DLPPDTTLLDLQNNKITEIKDGDFKNLKNLHALILVNNKISKVSPGAFTPLVKLERLYLSKNQL

KELPEKMPKTLQELRAHENEITKVRKVTFNGLNQMIVIELGTNPLKSSGIENGAFQGMKKLSYI

RIADTNITSIPQGLPPSLTELHLDGNKISRVDAASLKGLNNLAKLGLSFNSISAVDNGSLANTP

HLRELHLDNNKLTRVPGGLAEHKYIQVVYLHNNNISVVGSSDFCPPGHNTKKASYSGVSLFSNP

VQYWEIQPSTFRCVYVRSAIQLGNYK
```

Signal peptide sequence is shown in boldface type. Heavy chain sequence is underlined with a straight line. Linker sequence is shown in italics. Galacorin sequence is underlined with a wavy line.

```
Nivolumab Light Chain Gene Sequence
(SEQ ID NO: 36):
ATGATGTCCTTTGTCTCTCTGCTCCTGGTTGGCATCCTATTCCATGCCAC

CCAGGCCGAAATCGTATTGACTCAGTCCCTGCTACACTTTCACTGAGTC

CGGGTGAGCGGGCGACTTTGTCATGTCGGGCATCACAGAGTGTAAGTAGT

TATCTGGCCTGGTATCAACAGAAACCGGGACAGGCTCCTCGCCTGCTGAT

TTATGACGCAAGCAATCGCGCGACCGGCATCCCGGCGAGGTTCTCAGGGT

CTGGATCAGGTACTGACTTTACCCTTACGATCTCTTCTCTCGAACCTGAG

GATTTCGCTGTCTATTACTGCCAGCAGTCTTCTAACTGGCCGAGAACATT

TGGTCAAGGGACAAAAGTCGAGATTAAGCGAACTGTCGCAGCGCCATCTG

TCTTTATCTTCCCTCCAAGCGACGAACAGCTTAAGAGTGGCACCGCCAGT
```
```
-continued
GTTGTCTGCCTTCTGAATAACTTCTATCCAAGGGAAGCGAAAGTTCAGTG

GAAGGTGGATAACGCTCTGCAGTCTGGGAACTCTCAGGAAAGTGTAACAG

AACAAGACTCCAAAGACTCAACCTACTCTCTTAGTTCCACGTTGACCCTC

TCCAAAGCGGACTATGAGAAGCATAAGGTCTACGCTTGCGAGGTAACACA

CCAGGGGCTGAGTAGTCCGGTTACGAAGAGCTTCAACAGAGGGGAATGCT

GA
```

Signal peptide coding sequence is shown in boldface type. Light chain coding sequence is underlined with a straight line.

```
Nivolumab Light Chain Protein Sequence
(SEQ ID NO: 37):
MMSFVSLLLVGILFHATQAEIVLTQSPATLSLSPGERATLSCRASQSVSS

YLAWYQQKPGQAPRLLIYDASNRATGIPARFSGSGSGTDFTLTISSLEPE
```

<u>DFAVYYCQQSSNWPRTFGQGTKVEIKRTVAAPSVFIFPPSDEQLKSGTAS</u>

<u>VVCLLNNFYPREAKVQWKVDNALQSGNSQESVTEQDSKDSTYSLSSTLTL</u>

<u>SKADYEKHKVYACEVTHQGLSSPVTKSFNRGEC</u>  5

Signal peptide sequence is shown in boldface type. Light chain sequence is underlined with a straight line.
Component Amino Acid Sequences:

```
Signal sequence for heavy and light chains (SEQ ID NO: 5)
Linker sequence between decorin and heavy chain (SEQ ID NO: 6)
Decorin (SEQ ID NO: 7)
Nivolumab Heavy Chain Protein Sequence (SEQ ID NO: 38):
QVQLVESGGGVVQPGRSLRLDCKASGITFSNSGMHWVRQAPGKGLEWVAVIWYDGSKRYYADSV

KGRFTISRDNSKNTLFLQMNSLRAEDTAVYYCATNDDYWGQGTLVTVSSASTKGPSVFPLAPCS

RSTSESTAALGCLVKDYFPEPVTVSWNSGALTSGVHTFPAVLQSSGLYSLSSVVTVPSSSLGTK

TYTCNVDHKPSNTKVDKRVESKYGPPCPPCPAPEFLGGPSVFLFPPKPKDTLMISRTPEVTCVV

VDVSQEDPEVQFNWYVDGVEVHNAKTKPREEQFNSTYRVVSVLTVLHQDWLNGKEYKCKVSNKG

LPSSIEKTISKAKGQPREPQVYTLPPSQEEMTKNQVSLTCLVKGFYPSDIAVEWESNGQPENNY

KTTPPVLDSDGSFFLYSRLTVDKSRWQEGNVFSCSVMHEALHNHYTQKSLSLSLGK

Nivolumab Light Chain Protein Sequence (SEQ ID NO: 39):
EIVLTQSPATLSLSPGERATLSCRASQSVSSYLAWYQQKPGQAPRLLIYDASNRATGIPARFSG

SGSGTDFTLTISSLEPEDFAVYYCQQSSNWPRTFGQGTKVEIKRTVAAPSVFIFPPSDEQLKSG

TASVVCLLNNFYPREAKVQWKVDNALQSGNSQESVTEQDSKDSTYSLSSTLTLSKADYEKHKVY

ACEVTHQGLSSPVTKSFNRGEC

Anti-PD-1
Pembrolizumab-Galacorin Fusion Heavy Chain Gene Sequence (SEQ ID NO: 40):
```
ATGATGTCCTTTGTCTCTCTGCTCCTGGTTGGCATCCTATTCCATGCCACCCAGGCC<u>CAGGTGC</u>

<u>AATTGGTCCAAAGTGGGGTCGAGGTCAAGAAGCCAGGAGCTTCTGTAAAAGTTTCATGTAAGGC</u>

<u>ATCTGGGTATACCTTCACGAACTACTATATGTATTGGGTGCGCCAAGCGCCAGGGCAGGGCCTC</u>

<u>GAATGGATGGGTGGCATCAATCCGAGCAACGGGGGCACCAACTTTAACGAAAAGTTTAAAAACC</u>

<u>GGGTCACCTTGACAACGGACAGTAGCACGACTACCGCTTATATGGAGCTGAAGAGTTTGCAGTT</u>

<u>TGATGATACTGCGGTTTATTATTGTGCACGCAGAGATTATAGGTTCGACATGGGCTTCGACTAC</u>

<u>TGGGGTCAAGGTACTACGGTAACTGTATCATCTGCTAGTACAAAGGGCCCTTCCGTTTTCCCCC</u>

<u>TCGCCCCGTGCAGCCGCTCAACGTCCGAAAGCACCGCTGCACTTGGGTGCCTTGTAAAAGACTA</u>

<u>TTTTCCAGAGCCAGTTACCGTGTCTTGGAATAGTGGCGCACTTACGTCCGGGGTGCACACTTTT</u>

<u>CCGGCTGTCTTGCAATCCTCTGGACTCTATTCCTTGAGTAGCGTCGTAACAGTACCAAGTAGTA</u>

<u>GTCTCGGCACCAAAACGTATACGTGCAATGTTGATCATAAGCCTAGCAACACGAAAGTTGACAA</u>

<u>AAGAGTTGAGAGTAAATATGGACCCCCCTGTCCGCCATGCCCGGCCCCTGAATTCCTTGGGGGC</u>

<u>CCGTCTGTATTTCTTTTCCCGCCCAAGCCGAAGGATACACTGATGATAAGCAGAACGCCTGAGG</u>

<u>TTACCTGCGTCGTGGTCGACGTAAGCCAGGAAGATCCTGAGGTGCAATTTAATTGGTATGTGGA</u>

<u>CGGGGTCGAGGTTCATAATGCAAAAACAAAACCCCGAGAGGAGCAATTTAATTCAACGTACAGA</u>

<u>GTCGTTAGCGTACTTACAGTGCTGCACCAGGATTGGCTCAACGGGAAGGAGTATAAGTGCAAGG</u>

<u>TGTCTAATAAAGGTTTGCCCTCCAGTATAGAAAAAACCATCTCAAAGGCGAAAGGACAGCCTAG</u>

<u>AGAACCTCAAGTATATACCCTCCCACCCTCCCAAGAAGAGATGACAAAGAACCAAGTGAGTCTC</u>

<u>ACATGCCTCGTCAAGGGTTTCTACCCAAGCGATATAGCCGTAGAGTGGGAATCAAATGGTCAGC</u>

<u>CGGAGAATAACTACAAAACTACTCCGCCAGTCTTGGATAGCGACGGGTCTTTTTTCCTGTACTC</u>

-continued

TAGGCTGACGGTGGACAAGTCAAGATGGCAGGAAGGAAATGTTTTTAGCTGCTCCGTTATGCAT

GAGGCTCTCCACAATCATTATACACAAAAAAGTTTGTCTCTGTCATTGGGGAAA*TCCGGGGGTG*

*GCGGATCC*GATGAGGCTGCAGGGATAGGCCCAGAAGTTCCTGATGACCGCGACTTCGAGCCCTC

CCTAGGCCCAGTGTGCCCCTTCCGCTGTCAATGCCATCTTCGAGTGGTCCAGTGTTCTGATTTG

GGTCTGGACAAAGTGCCAAAGGATCTTCCCCCTGACACAACTCTGCTAGACCTGCAAAACAACA

AAATAACCGAAATCAAAGATGGAGACTTTAAGAACCTGAAGAACCTTCACGCATTGATTCTTGT

CAACAATAAAATTAGCAAAGTTAGTCCTGGAGCATTTACACCTTTGGTGAAGTTGGAACGACTT

TATCTGTCCAAGAATCAGCTGAAGGAATTGCCAGAAAAAATGCCCAAAACTCTTCAGGAGCTGC

GTGCCCATGAGAATGAGATCACCAAAGTGCGAAAAGTTACTTTCAATGGACTGAACCAGATGAT

TGTCATAGAACTGGGCACCAATCCGCTGAAGAGCTCAGGAATTGAAAATGGGGCTTTCCAGGGA

ATGAAGAAGCTCTCCTACATCCGCATTGCTGATACCAATATCACCAGCATTCCTCAAGGTCTTC

CTCCTTCCCTTACGGAATTACATCTTGATGGCAACAAAATCAGCAGAGTTGATGCAGCTAGCCT

GAAAGGACTGAATAATTTGGCTAAGTTGGGATTGAGTTTCAACAGCATCTCTGCTGTTGACAAT

GGCTCTCTGGCCAACACGCCTCATCTGAGGGAGCTTCACTTGGACAACAACAAGCTTACCAGAG

TACCTGGTGGGCTGGCAGAGCATAAGTACATCCAGGTTGTCTACCTTCATAACAACAATATCTC

TGTAGTTGGATCAAGTGACTTCTGCCCACCTGGACACAACACCAAAAAGGCTTCTTATTCGGGT

GTGAGTCTTTTCAGCAACCCGGTCCAGTACTGGGAGATACAGCCATCCACCTTCAGATGTGTCT

ACGTGCGCTCTGCCATTCAACTCGGAAACTATAAGTGA

40

Signal peptide coding sequence is shown in boldface type.
Heavy chain coding sequence is underlined with a straight
line. Linker coding sequence is shown in italics. Galacorin
coding sequence is underlined with a wavy line.

Pembrolizumab-Galacorin Fusion Heavy Chain Protein Sequence (SEQ ID NO: 41):
MMSFVSLLLVGILFHATQAQVQLVQSGVEVKKPGASVKVSCKASGYTFTNYYMYWVRQAPGQGL

EWMGGINPSNGGTNFNEKFKNRVTLTTDSSTTTAYMELKSLQFDDTAVYYCARRDYRFDMGFDY

PAVLQSSGLYSLSSVVTVPSSSLGTKTYTCNVDHKPSNTKVDKRVESKYGPPCPPCPAPEFLGG

PSVFLFPPKPKDTLMISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDKSRWQEGNVFSCSVMH

EALHNHYTQKSLSLSLGK*SGGGGS*DEAAGIGPEVPDDRDFEPSLGPVCPFRCQCHLRVVQCSDL

GLKDVPKDLPPDTTLLDLQNNKITEIKDGDFKNLKNLHALILVNNKISKVSPGAFTPLVKLERL

YLSKNQLKELPEKMPKTLQELRAHENEITKVRKVTFNGLNQMIVIELGTNPLKSSGIENGAFQG

MKKLSYIRIADTNITSIPQGLPPSLTELHLDGNKISRVDAASLKGLNNLAKLGLSFNSISAVDN

GSLANTPHLRELHLDNNKLTRVPGGLAEHKYIQVVYLHNNNISVVGSSDFCPPGHNTKKASYSG

VSLFSNPVQYWEIQPSTFRCVYVRSAIQLGNYK.

Signal peptide sequence is shown in boldface type. Heavy chain sequence is underlined with a straight line. Linker sequence is shown in italics. Galacorin sequence is underlined with a wavy line.

```
Pembrolizumab Light Chain Gene Sequence
(SEQ ID NO: 42):
ATGATGTCCTTTGTCTCTCTGCTCCTGGTTGGCATCCTATTCCATGCCAC

CCAGGCCGAAATTGTTCTTACGCAGAGTCCAGCAACTTTGTCACTCTCTC

CCGGCGAACGAGCGACATTGTCCTGTCGCGCGAGTAAGGGTGTCTCAACA

TCTGGATACTCATATCTGCATTGGTACCAGCAAAAACCGGGACAAGCGCC

GCGATTGCTGATTTATCTCGCCTCCTACCTTGAAAGTGGTGTGCCTGCGA

GGTTCTCCGGTAGTGGATCAGGCACCGATTTCACTTTGACCATCAGCAGC

CTCGAACCAGAAGATTTTGCCGTCTACTACTGCCAACATAGCAGGGATTT

GCCACTGACATTCGGCGGGGGTACGAAAGTTGAGATTAAACGGACTGTAG

CGGCACCTTCTGTCTTCATCTTCCCACCAAGCGATGAGCAGCTTAAAAGC

GGTACAGCTTCAGTGGTGTGCCTTTTGAACAACTTTTATCCGCGAGAAGC

CAAGGTCCAATGGAAGGTGGATAACGCTTTGCAATCCGGTAACTCACAGG
```

```
AGTCAGTAACAGAGCAAGATAGTAAAGATAGCACGTATTCACTTAGCAGT

ACCCTTACTCTTAGCAAGGCTGATTATGAAAAACATAAGGTATATGCGTG

CGAGGTAACGCACCAAGGACTTAGCTCCCCAGTGACGAAGTCATTTAACC

GGGGGGAGTGCTGA
```

Signal peptide coding sequence is shown in boldface type. Light chain coding sequence is underlined with a straight line.

```
Pembrolizumab Light Chain Protein Sequence
(SEQ ID NO: 43):
MMSFVSLLLVGILFHATQAEIVLTQSPATLSLSPGERATLSCRASKGVST

SGYSYLHWYQQKPGQAPRLLIYLASYLESGVPARFSGSGSGTDFTLTISS

LEPEDFAVYYCQHSRDLPLTFGGGTKVEIKRTVAAPSVFIFPPSDEQLKS

GTASVVCLLNNFYPREAKVQWKVDNALQSGNSQESVTEQDSKDSTYSLSS

TLTLSKADYEKHKVYACEVTHQGLSSPVTKSFNRGEC.
```

Signal peptide sequence is shown in boldface type. Light chain sequence is underlined with a straight line.
Component Amino Acid Sequences:

```
Signal sequence for heavy and light chains (SEQ ID NO: 5)
Linker sequence between decorin and heavy chain (SEQ ID NO: 6)
Decorin (SEQ ID NO: 7)
Pembrolizumab Heavy Chain Protein Sequence (SEQ ID NO: 44):
QVQLVQSGVEVKKPGASVKVSCKASGYTFTNYYMYWVRQAPGQGLEWMGGINPSNGGTNFNEKF

KNRVTLTTDSSTTTAYMELKSLQFDDTAVYYCARRDYRFDMGFDYWGQGTTVTVSSASTKGPSV

FPLAPCSRSTSESTAALGCLVKDYFPEPVTVSWNSGALTSGVHTFPAVLQSSGLLYSLSSVVTVP

SSSLGTKTYTCNVDHKPSNTKVDKRVESKYGPPCPPCPAPEFLGGPSVFLFPPKPKDTLMISRT

PEVTCVVVDVSQEDPEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVKGFYPSDIAVEWESN

GQPENNYKTTPPVLDSDGSFFLYSRLTVDKSRWQEGNVFSCSFMHEALHNHYTQKSLSLSLGK
Pembrolizumab Light Chain Protein Sequence (SEQ ID NO: 45):
EIVLTQSPATLSLSPGERATLSCRASKGVSTSGYSYLHWYQQKPGQAPRLLIYLASYLESGVPA

RFSGSGSGTDFTLTISSLEPEDFAVYYCQHSRDLPLTFGGGTKVEIKRTVAAPSVFIFPPSDEQ

LKSGTASVVCLLNNFYPREAKVQWKVDNALQSGNSQESVTEQDSKDSTYSLSSTLTLSKADYEK

HKVYACEVTHQGLSSPVTKSFNRGEC

Anti-PD-L1
Avelumab-Galacorin Fusion Heavy Chain Gene Sequence (SEQ ID NO: 50):
ATGATGTCCTTTGTCTCTCTGCTCCTGGTTGGCATCCTATTCCATGCCACCCAGGCCGAGGTAC

AGCTTTTGGAGTCAGGCGGGGGCTCGTCCAACCTGGGGGGTCACTCCGGTTGTCATGTGCTGC

CAGTGGCTTCACATTCTCATCTTACATTATGATGTGGGTTCGACAGGCCCCTGGGAAGGGGCTG

GAGTGGGTTTCCTCCATCTACCCCTCCGGGGGAATTACCTTCTATGCCGACACGGTAAAGGGTC

GCTTCACTATAAGTCGAGATAACAGCAAAAATACGCTGTATCTCCAGATGAACTCTCTCAGGGC

TGAGGACACAGCTGTATATTACTGCGCGCGGATTAAGTTGGGGACCGTCACAACAGTGGATTAC
```

TGGGGTCAAGGCACTCTGGTAACCGTATCCTCAGCATCCACCAAGGGCCCAAGTGTATTCCCGC

TGGCCCCTTCAAGTAAATCCACGTCTGGCGGCACAGCCGCTCTCGGTTGCCTGGTTAAGGACTA

CTTCCCAGAACCTGTCACTGTCAGTTGGAACTCAGGCGCATTGACATCTGGTGTCCATACATTC

CCCGCAGTCCTGCAAAGCTCTGGACTTTACAGTCTTAGTAGCGTAGTGACAGTCCCATCTTCAA

GTCTTGGGACCCAAACTTATATTTGCAACGTAAATCATAAACCCTCCAACACTAAAGTAGACAA

AAAAGTAGAGCCGAATCTTGCGACAAAACGCATACATGCCCACCATGTCCCGCTCCGGAACTC

CTGGGCGGCCCGTCCGTTTTTCTCTTTCCCCCAAAGCCCAAGGATACGCTTATGATCAGCAGAA

CACCGGAAGTTACTTGTGTAGTCGTTGACGTGTCTCACGAAGATCCCGAAGTCAAATTTAATTG

GTATGTGGATGGCGTCGAAGTGCACAACGCAAAAACCAAACCCAGAGAGGAACAGTATAACAGC

ACGTATCGAGTGGTCTCCGTACTTACGGTCCTCCACCAGGACTGGTTGAATGGCAAGGAGTACA

AGTGCAAAGTGAGCAATAAAGCGTTGCCAGCCCCGATCGAAAAAACCATCAGCAAGGCCAAGGG

ACAGCCTAGAGAGCCGCAGGTTTACACCTTGCCGCCATCAAGGGATGAACTGACTAAAAACCAG

GTATCCCTGACCTGCCTGGTTAAGGGTTTTTACCCCAGTGATATAGCGGTTGAATGGGAGTCTA

ACGGGCAGCCAGAGAACAACTACAAAACGACACCTCCCGTTCTGGATTCCGATGGCAGCTTTTT

CTTGTATTCTAAACTCACCGTGGATAAATCCCGATGGCAGCAAGGCAACGTCTTCTCCTGCAGC

GTGATGCATGAAGCCTTGCACAACCACTATACCCAAAAGAGTCTCAGCCTGTCACCCGGGAAAT

*CCGGGGGTGGCGGATCC*GATGAGGCTGCAGGGATAGGCCCAGAAGTTCCTGATGACCGCGACTT

CGAGCCCTCCCTAGGCCCAGTGTGCCCCTTCCGCTGTCAATGCCATCTTCGAGTGGTCCAGTGT

TCTGATTTGGGTCTGGACAAAGTGCCAAAGGATCTTCCCCCTGACACAACTCTGCTAGACCTGC

AAAACAACAAAATAACCGAAATCAAAGATGGAGACTTTAAGAACCTGAAGAACCTTCACGCATT

GATTCTTGTCAACAATAAAATTAGCAAAGTTAGTCCTGGAGCATTTACACCTTTGGTGAAGTTG

GAACGACTTTATCTGTCCAAGAATCAGCTGAAGGAATTGCCAGAAAAAATGCCCAAAACTCTTC

AGGAGCTGCGTGCCCATGAGAATGAGATCACCAAAGTGCGAAAAGTTACTTTCAATGGACTGAA

CCAGATGATTGTCATAGAACTGGGCACCAATCCGCTGAAGAGCTCAGGAATTGAAAATGGGGCT

TTCCAGGGAATGAAGAAGCTCTCCTACATCCGCATTGCTGATACCAATATCACCAGCATTCCTC

AAGGTCTTCCTCCTTCCCTTACGGAATTACATCTTGATGGCAACAAAATCAGCAGAGTTGATGC

AGCTAGCCTGAAAGGACTGAATAATTTTGGCTAAGTTGGGATTGAGTTTCAACAGCATCTCTGCT

GTTGACAATGGCTCTCTGGCCAACACGCCTCATCTGAGGGAGCTTCACTTGGACAACAACAAGC

TTACCAGAGTACCTGGTGGGCTGGCAGAGCATAAGTACATCCAGGTTGTCTACCTTCATAACAA

CAATATCTCTGTAGTTGGATCAAGTGACTTCTGCCCACCTGGACACAACACCAAAAAGGCTTCT

TATTCGGGTGTGAGTCTTTTCAGCAACCCGGTCCAGTACTGGGAGATACAGCCATCCACCTTCA

GATGTGTCTACGTGCGCTCTGCCATTCAACTCGGAAACTATAAGTGA

Signal peptide coding sequence is shown in boldface type. Heavy chain coding sequence is underlined with a straight line. Linker coding sequence is shown in italics. Galacorin coding sequence is underlined with a wavy line.

```
Avelumab-Galacorin Fusion Heavy Chain Protein Sequence (SEQ ID NO: 51):
MMSFVSLLLVGILFHATQAEVQLLESGGGLVQPGGSLRLSCAASGFTFSSYIMMWVRQAPGKGL

EWVSSIYPSGGITFYADTVKGRFTISRDNSKNTLYLQMNSLRAEDTAVYYCARIKLGTVTTVDY

WGQGTLVTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTVDKSRWQQGNVFSCS

VMHEALHNHYTQKSLSLSPGKSGGGGSDEAAGIGPEVPDDRDFEPSLGPVCPFRCQCHLRVVQC

SDLGLDKVPKDLPPDTTLLDLQNNKITEIKDGDFKNLKNLHALILVNNKISKVSPGAFTPLVKL

ERLYLSKNQLKELPEKMPKTLQELRAHENEITKVRKVTFNGLNQMIVIELGTNPLKSSGIENGA

FQGMKKLSYIRIADTNITSIPQGLPPSLTELHLDGNKISRVDAASLKGLNNLAKLGLSFNSISA

VDNGSLANTPHLRELHLDNNKLTRVPGGLAEHKYIQVVYLHNNNISVVGSSDFCPPGHNTKKAS

YSGVSLFSNPVQYWEIQPSTFRCVYVRSAIQLGNYK.
```

Signal peptide sequence is shown in boldface type. Heavy chain sequence is underlined with a straight line. Linker sequence is shown in italics. Galacorin sequence is underlined with a wavy line.

```
Avelumab Light Chain Gene Sequence
(SEQ ID NO: 52):
ATGATGTCCTTTGTCTCTCTGCTCCTGGTTGGCATCCTATTCCATGCCAC

CCAGGCCCAGTCTGCACTTACACAACCGGCGTCCGTTTCCGGATCTCCAG

GACAGAGCATTACTATCAGTTGCACGGGAACCTCCTCAGACGTAGGGGGG

TATAATTATGTGTCTTGGTATCAACAGCATCCCGGGAAAGCCCCCAAACT

GATGATCTACGATGTCAGCAATAGACCAAGCGGTGTGAGTAATCGATTTA

GCGGGTCTAAATCTGGTAACACAGCATCCCTCACTATTAGTGGACTGCAA

GCAGAAGATGAGGCAGACTATTATTGCAGTAGCTATACGTCTAGTTCCAC

CCGCGTTTTTGGCACTGGGACGAAAGTCACCGTTCTCGGACAACCAAAAG

CAAACCCCACCGTGACTCTGTTTCCGCCTAGCAGCGAAGAATTGCAGGCC

AATAAGGCGACACTCGTATGCCTTATCTCCGACTTCTACCCGGGCGCTGT

GACAGTCGCGTGGAAAGCCGACGGCAGCCCTGTTAAAGCTGGAGTCGAGA

CCACGAAGCCGTCCAAGCAGAGTAACAATAAGTATGCTGCATCCAGTTAT

CTCTCTCTCACTCCGGAACAGTGGAAGTCCCATCGGTCCTATAGTTGCCA

AGTGACCCATGAGGGTTCCACCGTAGAGAAAACGGTAGCACCTACCGAAT

GTAGTTGA
```

Signal peptide coding sequence is shown in boldface type. Light chain coding sequence is underlined with a straight line.

```
Avelumab Light Chain Protein Sequence
(SEQ ID NO: 53):
MMSFVSLLLVGILFHATQAQSALTQPASVSGSPGQSITISCTGTSSDVGG

YNYVSWYQQHPGKAPKLMIYDVSNRPSGVSNRFSGSKSGNTASLTISGLQ

AEDEADYYCSSYTSSSTRVFGTGTKVTVLGQPKANPTVTLFPPSSEELQA

NKATLVCLISDFYPGAVTVAWKADGSPVKAGVETTKPSKQSNNKYAASSY

LSLTPEQWKSHRSYSCQVTHEGSTVEKTVAPTECS.
```

Signal peptide sequence is shown in boldface type. Light chain sequence is underlined with a straight line.

Anti-PD-L 1

In some embodiments, constructs comprise two or more copies of galacorin or other decorin molecule attached to each C heavy chain gene or a portion of the galacorin molecule (e.g., TGF-Beta binding moiety) attached to the heavy chain gene as a single entity or as two or more copies. There are multiple TGF-Beta binding domains in the Galacorin/Decorin molecule. These domains are configured in any suitable configuration. In some embodiments, each of the above-described options is attached to a bi- or multi specific antibody directed at 2 or more targets. Exemplary sequences are shown below.

Avelumab-Galacorin2x Fusion Heavy Chain Gene Sequence (SEQ ID NO:54):
ATGATGTCCTTTGTCTCTCTGCTCCTGGTTGGCATCCTATTCCATGCCACCCAGGCC<u>GAGGTAC

AGCTTTTGGAGTCAGGCGGGGGCTCGTCCAACCTGGGGGGTCACTCCGGTTGTCATGTGCTGC

CAGTGGCTTCACATTCTCATCTTACATTATGATGTGGGTTCGACAGGCCCCTGGGAAGGGGCTG

GAGTGGGTTTCCTCCATCTACCCCTCCGGGGGAATTACCTTCTATGCCGACACGGTAAAGGGTC

GCTTCACTATAAGTCGAGATAACAGCAAAAATACGCTGTATCTCCAGATGAACTCTCTCAGGGC

TGAGGACACAGCTGTATATTACTGCGCGCGGATTAAGTTGGGGACCGTCACAACAGTGGATTAC

TGGGGTCAAGGCACTCTGGTAACCGTATCCTCAGCATCCACCAAGGGCCCAAGTGTATTCCCGC

TGGCCCCTTCAAGTAAATCCACGTCTGGCGGCACAGCCGCTCTCGGTTGCCTGGTTAAGGACTA

CTTCCCAGAACCTGTCACTGTCAGTTGGAACTCAGGCGCATTGACATCTGGTGTCCATACATTC

CCCGCAGTCCTGCAAAGCTCTGGACTTTACAGTCTTAGTAGCGTAGTGACAGTCCCATCTTCAA

GTCTTGGGACCCAAACTTATATTTGCAACGTAAATCATAAACCCTCCAACACTAAAGTAGACAA

AAAAGTAGAGCCGAAATCTIGCGACAAAACGCATACATGCCCACCATGTCCCGCTCCGGAACTC

CTGGGCGGCCCGTCCGTTTTTCTCTTTCCCCCAAAGCCCAAGGATACGCTTATGATCAGCAGAA

CACCGGAAGTTACTTGTGTAGTCGTTGACGTGTCTCACGAAGATCCCGAAGTCAAATTTAATTG

GTATGTGGATGGCGTCGAAGTGCACAACGCAAAAACCAAACCCAGAGAGGAACAGTATAACAGC

ACGTATCGAGTGGTCTCCGTACTTACGGTCCTCCACCAGGACTGGTTGAATGGCAAGGAGTACA

AGTGCAAAGTGAGCAATAAAGCGTTGCCAGCCCCGATCGAAAAAACCATCAGCAAGGCCAAGGG

ACAGCCTAGAGAGCCGCAGGTTTACACCTTGCCGCCATCAAGGGATGAACTGACTAAAAACCAG

GTATCCCTGACCTGCCTGGTTAAGGGTTTTTACCCCAGTGATATAGCGGTTGAATGGGAGTCTA

ACGGGCAGCCAGAGAACAACTACAAAACGACACCTCCCGTTCTGGATTCCGATGGCAGCTTTTT

CTTGTATTCTAAACTCACCGTGGATAAATCCCGATGGCAGCAAGGCAACGTCTTCTCCTGCAGC

GTGATGCATGAAGCCTTGCACAACCACTATACCCAAAAGAGTCTCAGCCTGTCACCCGGGAAAT</u>

*CCGGGGGTGGCGGATCC*<span style="text-decoration: wavy underline">ATGAGGCTGCAGGGATAGGCCCAGAAGTTCCTGATGACCGCGACTT

CGAGCCCTCCCTAGGCCCAGTGTGCCCCTTCCGCTGTCAATGCCATCTTCGAGTGGTCCAGTGT

TCTGATTTGGGTCTGGACAAAGTGCCAAAGGATCTTCCCCCTGACACAACTCTGCTAGACCTGC

AAAACAACAAAATAACCGAAATCAAAGATGGAGACTTTAAGAACCTGAAGAACCTTCACGCATT

GATTCTTGTCAACAATAAAATTAGCAAAGTTAGTCCTGGAGCATTTACACCTTTGGTGAAGTTG

GAACGACTTTATCTGTCCAAGAATCAGCTGAAGGAATTGCCAGAAAAAATGCCCAAAACTCTTC

AGGAGCTGCGTGCCCATGAGAATGAGATCACCAAAGTGCGAAAAGTTACTTTCAATGGACTGAA

CCAGATGATTGTCATAGAACTGGGCACCAATCCGCTGAAGAGCTCAGGAATTGAAAATGGGGCT

TTCCAGGGAATGAAGAAGCTCTCCTACATCCGCATTGCTGATACCAATATCACCAGCATTCCTC

AAGGTCTTCCTCCTTCCCTTACGGAATTACATCTTGATGGCAACAAAATCAGCAGAGTTGATGC

AGCTAGCCTGAAAGGACTGAATAATTTGGCTAAGTTGGGATTGAGTTTCAACAGCATCTCTGCT

GTTGACAATGGCTCTCTGGCCAACACGCCTCATCTGAGGGAGCTTCACTTGGACAACAACAAGC</span>

-continued

TTACCAGAGTACCTGGTGGGCTGGCAGAGCATAAGTACATCCAGGTTGTCTACCTTCATAACAA

CAATATCTCTGTAGTTGGATCAAGTGACTTCTGCCCACCTGGACACAACACCAAAAAGGCTTCT

TATTCGGGTGTGAGTCTTTTCAGCAACCCGGTCCAGTACTGGGAGATACAGCCATCCACCTTCA

GATGTGTCTACGTGCGCTCTGCCATTCAACTCGGAAACTATAAG*TCCGGGGGTGGCGGATCCGA*

TGAGGCTGCAGGGATAGGCCCAGAAGTTCCTGATGACCGCGACTTCGAGCCCTCCCTAGGCCCA

GTGTGCCCCTTCCGCTGTCAATGCCATCTTCGAGTGGTCCAGTGTTCTGATTTGGGTCTGGACA

AAGTGCCAAAGGATCTTCCCCCTGACACAACTCTGCTAGACCTGCAAAACAACAAAATAACCGA

AATCAAAGATGGAGACTTTAAGAACCTGAAGAACCTTCACGCATTGATTCTTGTCAACAATAAA

ATTAGCAAAGTTAGTCCTGGAGCATTTACACCTTTGGTGAAGTTGGAACGACTTTATCTGTCCA

AGAATCAGCTGAAGGAATTGCCAGAAAAAATGCCCAAAACTCTTCAGGAGCTGCGTGCCCATGA

GAATGAGATCACCAAAGTGCGAAAAGTTACTTTCAATGGACTGAACCAGATGATTGTCATAGAA

CTGGGCACCAATCCGCTGAAGAGCTCAGGAATTGAAAATGGGGCTTTCCAGGGAATGAAGAAGC

TCTCCTACATCCGCATTGCTGATACCAATATCACCAGCATTCCTCAAGGTCTTCCTCCTTCCCT

TACGGAATTACATCTTGATGGCAACAAAATCAGCAGAGTTGATGCAGCTAGCCTGAAAGGACTG

AATAATTTGGCTAAGTTGGGATTGAGTTTCAACAGCATCTCTGCTGTTGACAATGGCTCTCTGG

CCAACACGCCTCATCTGAGGGAGCTTCACTTGGACAACAACAAGCTTACCAGAGTACCTGGTGG

GCTGGCAGAGCATAAGTACATCCAGGTTGTCTACCTTCATAACAACAATATCTCTGTAGTTGGA

TCAAGTGACTTCTGCCCACCTGGACACAACACCAAAAAGGCTTCTTATTCGGGTGTGAGTCTTT

TCAGCAACCCGGTCCAGTACTGGGAGATACAGCCATCCACCTTCAGATGTGTCTACGTGCGCTC

TGCCATTCAACTCGGAAACTATAAGTGA

Signal peptide coding sequence is shown in boldface type.
Heavy chain coding sequence is underlined with a straight
line. Linker coding sequences are shown in italics. Galacorin
coding sequences are underlined with a wavy line.

```
Avelumab-Galacorin2x Fusion Heavy Chain Protein Sequence (SEQ ID NO: 55):
MMSFVSLLLVGILFHATQAEVQLLESGGGLVQPGGSLRLSCAASGFTFSSYIMMWVRQAPGKGL

EWVSSIYPSGGITFYADTVKGRFTISRDNSKNTLYLQMNSLRAEDTAVYYCARIKLGTVTTVDY

WGQGTLVTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDELTKNQ
```

-continued

VSLTCLVKGFYPSDIAVEWESNGQPENNYKTTPPVLDSDGSFFLYSKLTVDKSRWQQGNVFSCS

VMHEALHNHYTQKSLSLSPGK*SGGGGS*DEAAGIGPEVPDDRDFEPSLGPVCPFRCQCHLRVVQC

SDLGLDKVPKDLPPDTTLLSLQNNKITEIKDGDFKNLKNLHALILVNNKISKVSPGAFTPLVKL

ERLYLSKNQLKELPEKMPKTLQELRAHENEITKVRKVTFNGLNQMIVIELGTNPLKSSGIENGA

FQGMKKLSYIRIADTNITSIPQGLPPSLTELHLDGNKISRVDAASLKGLNNLAKLGLSFNSISA

VDNGSLANTPHLRELHLDNNKLTRVPGGLAEHKYIQVVYLHNNNISVVGSSDFCPPGHNTKKAS

YSGVSLFSNPVQYWEIQPSTFRCVYVRSAIQLGNYK*SGGGGS*DEAAGIGPEVPDDRDFEPSLGP

VCPFRCQCHLRVVQCSDLGLDKVPKDLPPDTTLLDLQNNKITEIKDGDFKNLKNLHALILVNNK

ISKVSPGAFTPLVKLERLYLSKNQLKELPEKMPKTLQELRAHENEITKVRKVTFNGLNQMIVIE

LGTNPLKSSGIENGAFQGMKKLSYIRIADTNITSIPQGLPPSLTELHLDGNKISRVDAASLKGL

NNLAKLGLSFNSISAVDNGSLANTPHLRELHLDNNKLTRVPGGLAEHKYIQVVYLHNNNISVVG

SSDFCPPGHNTKKASYSGVSLFSNPVQYWEIQPSTFRCVYVRSAIQLGNYK.

Signal peptide sequence is shown in boldface type. Heavy chain sequence is underlined with a straight line. Linker sequences are shown in italics. Galacorin sequences are underlined with a wavy line.

Avelumab-Galacorin/Decorin (Asp45-Lys359 of full length endogenous human Decorin) TGF-Beta Binding Domains Fusion Heavy Chain Gene Sequence (SEQ ID NO:56):
ATGATGTCCTTTGTCTCTCTGCTCCTGGTTGGCATCCTATTCCATGCCACCCAGGCCGAGGTAC

AGCTTTTGGAGTCAGGCGGGGGGCTCGTCCAACCTGGGGGGTCACTCCGGTTGTCATGTGCTGC

CAGTGGCTTCACATTCTCATCTTACATTATGATGTGGGTTCGACAGGCCCCTGGGAAGGGGCTG

GAGTGGGTTTCCTCCATCTACCCCTCCGGGGGAATTACCTTCTATGCCGACACGGTAAAGGGTC

GCTTCACTATAAGTCGAGATAACAGCAAAAATACGCTGTATCTCCAGATGAACTCTCTCAGGGC

TGAGGACACAGCTGTATATTACTGCGCGCGGATTAAGTTGGGGACCGTCACAACAGTGGATTAC

TGGGGTCAAGGCACTCTGGTAACCGTATCCTCAGCATCCACCAAGGGCCCAAGTGTATTCCCGC

TGGCCCCTTCAAGTAAATCCACGTCTGGCGGCACAGCCGCTCTCGGTTGCCTGGTTAAGGACTA

CTTCCCAGAACCTGTCACTGTCAGTTGGAACTCAGGCGCATTGACATCTGGTGTCCATACATTC

CCCGCAGTCCTGCAAAGCTCTGGACTTTACAGTCTTAGTAGCGTAGTGACAGTCCCATCTTCAA

GTCTTGGGACCCAAACTTATATTTGCAACGTAAATCATAAACCCTCCAACACTAAAGTAGACAA

AAAAGTAGAGCCGAAATCTTGCGACAAAACGCATACATGCCCACCATGTCCCGCTCCGGAACTC

CTGGGCGGCCCGTCCGTTTTTCTCTTTCCCCCAAAGCCCAAGGATACGCTTATGATCAGCAGAA

CACCGGAAGTTACTTGTGTAGTCGTTGACGTGTCTCACGAAGATCCCGAAGTCAAATTTAATTG

GTATGTGGATGGCGTCGAAGTGCACAACGCAAAAACCAAACCCAGAGAGGAACAGTATAACAGC

ACGTATCGAGTGGTCTCCGTACTTACGGTCCTCCACCAGGACTGGTTGAATGGCAAGGAGTACA

AGTGCAAAGTGAGCAATAAAGCGTTGCCAGCCCCCGATCGAAAAAACCATCAGCAAGGCCAAGGG

-continued

ACAGCCTAGAGAGCCGCAGGTTTACACCTTGCCGCCATCAAGGGATGAACTGACTAAAAACCAG

GTATCCCTGACCTGCCTGGTTAAGGGTTTTTACCCCAGTGATATAGCGGTTGAATGGGAGTCTA

ACGGGCAGCCAGAGAACAACTACAAAACGACACCTCCCGTTCTGGATTCCGATGGCAGCTTTTT

CTTGTATTCTAAACTCACCGTGGATAAATCCCGATGGCAGCAAGGCAACGTCTTCTCCTGCAGC

GTGATGCATGAAGCCTTGCACAACCACTATACCCAAAAGAGTCTCAGCCTGTCACCCGGGAAA*T*

*CCGGGGGTGGCGGATCC*GACTTCGAGCCCTCCCTAGGCCCAGTGTGCCCCTTCCGCTGTCAATG

CCATCTTCGAGTGGTCCAGTGTTCTGATTTGGGTCTGGACAAAGTGCCAAAGGATCTTCCCCCT

GACACAACTCTGCTAGACCTGCAAAACAACAAAATAACCGAAATCAAAGATGGAGACTTTAAGA

ACCTGAAGAACCTTCACGCATTGATTCTTGTCAACAATAAAATTAGCAAAGTTAGTCCTGGAGC

ATTTACACCTTTGGTGAAGTTGGAACGACTTTATCTGTCCAAGAATCAGCTGAAGGAATTGCCA

GAAAAAATGCCCAAAACTCTTCAGGAGCTGCGTGCCCATGAGAATGAGATCACCAAAGTGCGAA

AAGTTACTTTCAATGGACTGAACCAGATGATTGTCATAGAACTGGGCACCAATCCGCTGAAGAG

CTCAGGAATTGAAAATGGGGCTTTCCAGGGAATGAAGAAGCTCTCCTACATCCGCATTGCTGAT

ACCAATATCACCAGCATTCCTCAAGGTCTTCCTCCTTCCCTTACGGAATTACATCTTGATGGCA

ACAAAATCAGCAGAGTTGATGCAGCTAGCCTGAAAGGACTGAATAATTTGGCTAAGTTGGGATT

GAGTTTCAACAGCATCTCTGCTGTTGACAATGGCTCTCTGGCCAACACGCCTCATCTGAGGGAG

CTTCACTTGGACAACAACAAGCTTACCAGAGTACCTGGTGGGCTGGCAGAGCATAAGTACATCC

AGGTTGTCTACCTTCATAACAACAATATCTCTGTAGTTGGATCAAGTGACTTCTGCCCACCTGG

ACACAACACCAAAAAGGCTTCTTATTCGGGTGTGAGTCTTTTCAGCAACCCGGTCCAGTACTGG

GAGATACAGCCATCCACCTTCAGATGTGTCTACGTGCGCTCTGCCATTCAACTCGGAAACTATA

AGTGA

Signal peptide coding sequence is shown in boldface type.
Heavy chain coding sequence is underlined with a straight
line. Linker coding sequence is shown in italics. Galacorin/
Decorin (Asp45-Lys 359) coding sequence is underlined
with a wavy line.

Avelumab-Galacorin/Decorin (Asp45-Lys359 of full length endogenous human Decorin) TGF-
Beta Binding Domains Fusion Heavy Chain Protein Sequence (SEQ ID NO:57):
MMSFVSLLLVGILFHATQAEVQLLESGGGLVQPGGSLRLSCAASGFTFSSYIMMWVRQAPGKGL

EWVSSIYPSGGITFYADTVKGRFTISRDNSKNTLYLQMNSLRAEDTAVYYCARIKLGTVTTVDY

WGQGTLVTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDELTKNQ

-continued

VSLTCLVKGFYPSDIAVEWESNGQPENNYKTTPPVLDSDGSFFLYSKLTVDKSRWQQGNVFSCS

VMHEALHNHYTQKSLSLSPGK*SGGGGS*DFEPSLGPVCPFRCQCHLRVVQCSDLGLDKVPKDLPP

DTTLLDLQNNKITEIKDGDFKNLKNLHALILVNNKISKVSPGAFTPLVKLERLYLSKNQLKELP

EKMPKTLQELRAHENEITKVRKVTFNGLNQMIVIELGTNPLKSSGIENGAFQGMKKLSYIRIAD

TNITSIPQGLPPSLTELHLDGNKISRVDAASLKGLNNLAKLGLSFNSISAVDNGSLANTPHLRE

LHLDNNKLTRVPGGLAEHKYIQVVYLHNNNISVVGSSDFCPPGHNTKKASYSGVSLFSNPVQYW

EIQPSTFRCVYVRSAIQLGNYK.

Signal peptide sequence is shown in boldface type. Heavy chain sequence is underlined with a straight line. Linker sequence is shown in italics. Galacorin/Decorin (Asp45-Lys 359) sequence is underlined with a wavy line.

Avelumab-Galacorin/Decorin (Asp45-Lys359 of full length endogenous human Decorin) TGF-Beta Binding Domains 2x Fusion Heavy Chain Gene Sequence (SEQ ID NO:58):
ATGATGTCCTTTGTCTCTCTGCTCCTGGTTGGCATCCTATTCCATGCCACCCAGGCCGAGGTAC

AGCTTTTGGAGTCAGGCGGGGGGCTCGTCCAACCTGGGGGGTCACTCCGGTTGTCATGTGCTGC

CAGTGGCTTCACATTCTCATCTTACATTATGATGTGGGTTCGACAGGCCCCTGGGAAGGGGCTG

GAGTGGGTTTCCTCCATCTACCCCTCCGGGGGAATTACCTTCTATGCCGACACGGTAAAGGGTC

GCTTCACTATAAGTCGAGATAACAGCAAAAATACGCTGTATCTCCAGATGAACTCTCTCAGGGC

TGAGGACACAGCTGTATATTACTGCGCGCGGATTAAGTTGGGGACCGTCACAACAGTGGATTAC

TGGGGTCAAGGCACTCTGGTAACCGTATCCTCAGCATCCACCAAGGGCCCAAGTGTATTCCCGC

TGGCCCCTTCAAGTAAATCCACGTCTGGCGGCACAGCCGCTCTCGGTTGCCTGGTTAAGGACTA

CTTCCCAGAACCTGTCACTGTCAGTTGGAACTCAGGCGCATTGACATCTGGTGTCCATACATTC

CCCGCAGTCCTGCAAAGCTCTGGACTTTACAGTCTTAGTAGCGTAGTGACAGTCCCATCTTCAA

GTCTTGGGACCCAAACTTATATTTGCAACGTAAATCATAAACCCTCCAACACTAAAGTAGACAA

AAAAGTAGAGCCGAAATCTIGCGACAAAACGCATACATGCCCACCATGTCCCGCTCCGGAACTC

CTGGGCGGCCCGTCCGTTTTTCTCTTTCCCCCAAAGCCCAAGGATACGCTTATGATCAGCAGAA

CACCGGAAGTTACTTGTGTAGTCGTTGACGTGTCTCACGAAGATCCCGAAGTCAAATTTAATTG

GTATGTGGATGGCGTCGAAGTGCACAACGCAAAAACCAAACCCAGAGAGGAACAGTATAACAGC

ACGTATCGAGTGGTCTCCGTACTTACGGTCCTCCACCAGGACTGGTTGAATGGCAAGGAGTACA

AGTGCAAAGTGAGCAATAAAGCGTTGCCAGCCCCGATCGAAAAAACCATCAGCAAGGCCAAGGG

ACAGCCTAGAGAGCCGCAGGTTTACACCTTGCCGCCATCAAGGGATGAACTGACTAAAAACCAG

GTATCCCTGACCTGCCTGGTTAAGGGTTTTTACCCCAGTGATATAGCGGTTGAATGGGAGTCTA

ACGGGCAGCCAGAGAACAACTACAAAACGACACCTCCCGTTCTGGATTCCGATGGCAGCTTTTT

CTTGTATTCTAAACTCACCGTGGATAAATCCCGATGGCAGCAAGGCAACGTCTTCTCCTGCAGC

GTGATGCATGAAGCCTTGCACAACCACTATACCCAAAAGAGTCTCAGCCTGTCACCCGGGAAAT

*CCGGGGGTGGCGGATCC*GACTTCGAGCCCTCCCTAGGCCCAGTGTGCCCCTTCCGCTGTCAATG

-continued

CCATCTTCGAGTGGTCCAGTGTTCTGATTTGGGTCTGGACAAAGTGCCAAAGGATCTTCCCCCT

GACACAACTCTGCTAGACCTGCAAAACAACAAAATAACCGAAATCAAAGATGGAGACTTTAAGA

ACCTGAAGAACCTTCACGCATTGATTCTTGTCAACAATAAAATTAGCAAAGTTAGTCCTGGAGC

ATTTACACCTTTGGTGAAGTTGGAACGACTTTATCTGTCCAAGAATCAGCTGAAGGAATTGCCA

GAAAAAATGCCCAAAACTCTTCAGGAGCTGCGTGCCCATGAGAATGAGATCACCAAAGTGCGAA

AAGTTACTTTCAATGGACTGAACCAGATGATTGTCATAGAACTGGGCACCAATCCGCTGAAGAG

CTCAGGAATTGAAAATGGGGCTTTCCAGGGAATGAAGAAGCTCTCCTACATCCGCATTGCTGAT

ACCAATATCACCAGCATTCCTCAAGGTCTTCCTCCTTCCCTTACGGAATTACATCTTGATGGCA

ACAAAATCAGCAGAGTTGATGCAGCTAGCCTGAAAGGACTGAATAATTTGGCTAAGTTGGGATT

GAGTTTCAACAGCATCTCTGCTGTTGACAATGGCTCTCTGGCCAACACGCCTCATCTGAGGGAG

CTTCACTTGGACAACAACAAGCTTACCAGAGTACCTGGTGGGCTGGCAGAGCATAAGTACATCC

AGGTTGTCTACCTTCATAACAACAATATCTCTGTAGTTGGATCAAGTGACTTCTGCCCACCTGG

ACACAACACCAAAAAGGCTTCTTATTCGGGTGTGAGTCTTTTCAGCAACCCGGTCCAGTACTGG

GAGATACAGCCATCCACCTTCAGATGTGTCTACGTGCGCTCTGCCATTCAACTCGGAAACTATA

AGTCCGGGGGTGGCGGATCCGACTTCGAGCCCTCCCTAGGCCCAGTGTGCCCCTTCCGCTGTCA

ATGCCATCTTCGAGTGGTCCAGTGTTCTGATTTGGGTCTGGACAAAGTGCCAAAGGATCTTCCC

CCTGACACAACTCTGCTAGACCTGCAAAACAACAAAATAACCGAAATCAAAGATGGAGACTTTA

AGAACCTGAAGAACCTTCACGCATTGATTCTTGTCAACAATAAAATTAGCAAAGTTAGTCCTGG

AGCATTTACACCTTTGGTGAAGTTGGAACGACTTTATCTGTCCAAGAATCAGCTGAAGGAATTG

CCAGAAAAAATGCCCAAAACTCTTCAGGAGCTGCGTGCCCATGAGAATGAGATCACCAAAGTGC

GAAAAGTTACTTTCAATGGACTGAACCAGATGATTGTCATAGAACTGGGCACCAATCCGCTGAA

GAGCTCAGGAATTGAAAATGGGGCTTTCCAGGGAATGAAGAAGCTCTCCTACATCCGCATTGCT

GATACCAATATCACCAGCATTCCTCAAGGTCTTCCTCCTTCCCTTACGGAATTACATCTTGATG

GCAACAAAATCAGCAGAGTTGATGCAGCTAGCCTGAAAGGACTGAATAATTTGGCTAAGTTGGG

ATTGAGTTTCAACAGCATCTCTGCTGTTGACAATGGCTCTCTGGCCAACACGCCTCATCTGAGG

-continued

GAGCTTCACTTGGACAACAACAAGCTTACCAGAGTACCTGGTGGGCTGGCAGAGCATAAGTACA

TCCAGGTTGTCTACCTTCATAACAACAATATCTCTGTAGTTGGATCAAGTGACTTCTGCCCACC

TGGACACAACACCAAAAAGGCTTCTTATTCGGGTGTGAGTCTTTTCAGCAACCCGGTCCAGTAC

TGGGAGATACAGCCATCCACCTTCAGATGTGTCTACGTGCGCTCTGCCATTCAACTCGGAAACT

ATAAGTGA

Signal peptide coding sequence is shown in boldface type. Heavy chain coding sequence is underlined with a straight line. Linker coding sequences are shown in italics. Galacorin/Decorin (Asp45-Lys 359) coding sequences are underlined with a wavy line.

Avelumab-Galacorin/Decorin (Asp45-Lys359 of full length endogenous human Decorin) TGF-Beta Binding Domains 2x Fusion Heavy Chain Protein Sequence (SEQ ID NO:59):

MMSFVSLLLVGILFHATQAEVQLLESGGGLVQPGGSLRLSCAASGFTFSSYIMMWVRQAPGKGL

EWVSSIYPSGGITFYADTVKGRFTISRDNSKNTLYLQMNSLRAEDTAVYYCARIKLGTVTTVDY

WGQGTLVTVSSASTKGPSVFPLAPSSKSTSGGTAALGCLVKDYFPEPVTVSWSGALTSGVHTF

PAVLQSSGLYSLSSVVTVPSSSLGTQTYICNVNHKPSNTKDKKVEPKSCDKTHTCPPCPAPEL

LGGPSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTVDKSRWQQGNVFSCS

VMHEALHNHYTQKSLSLSPGK*SGGGGS*DFEPSLGPVCPFRCQCHLRVVQCSDLGLDKVPKDLPP

DTTLLDLQNNKITEIKDGDFKNLKNLHALILVNNKISKVSPGAFTPLVKLERLYLSKNQLKELP

EKMPKTLQELRAHENEITKVRKVTFNGLNQMIVIELGTNPLKSSGIENGAFQGMKKLSYIRIAD

TNITSIPQGLPPSLTELHLDGNKISRVDAASLKGLNNLAKLGLSFNSISAVDNGSLANTPHLRE

LHLDNNKLTRVPGGLAEHKYIQVVYLHNNNISVVGSSDFCPPGHNTKKASYSGVSLFSNPVQYW

EIQPSTFRCVYVRSAIQLGNYK*SGGGGS*DFEPSLGPVCPFRCQCHLRVVQCSDLGLDKVPKDLP

PDTTLLDLQNNKITEIKDGDFKNLKNLHALILVNNKISKVSPGAFTPLVKLERLYLSKNQLKEL

PEKMPKTLQELRAHENEITKVRKVTFNGLNQMIVIELGTNPLKSSGIENGAFQGMKKLSYIRIA

DTNITSIPQGLPPSLTELHLDGNKISRVDAASLKGLNNLAKLGLSFNSISAVDNGSLANTPHLR

ELHLDNNKLTRVPGGLAEHKYIQVVYLHNNNISVVGSSDFCPPGHNTKKASYSGVSLFSNPVQY

WEIQPSTFRCVYVRSAIQLGNYK.

Signal peptide sequence is shown in boldface type. Heavy chain sequence is underlined with a straight line. Linker sequences are shown in italics. Galacorin/Decorin (Asp45-Lys 359) sequences are underlined with a wavy line.

Avelumab-Galacorin/Decorin (Leu155-Val260 of full length endogenous human Decorin) TGF-Beta Binding Domain Fusion Heavy Chain Gene Sequence (SEQ ID NO:60):
ATGATGTCCTTTGTCTCTCTGCTCCTGGTTGGCATCCTATTCCATGCCACCCAGGCC<u>GAGGTAC</u>

<u>AGCTTTTGGAGTCAGGCGGGGGGCTCGTCCAACCTGGGGGGTCACTCCGGTTGTCATGTGCTGC</u>

<u>CAGTGGCTTCACATTCTCATCTTACATTATGATGTGGGTTCGACAGGCCCCTGGGAAGGGGCTG</u>

<u>GAGTGGGTTTCCTCCATCTACCCCTCCGGGGGAATTACCTTCTATGCCGACACGGTAAAGGGTC</u>

<u>GCTTCACTATAAGTCGAGATAACAGCAAAAATACGCTGTATCTCCAGATGAACTCTCTCAGGGC</u>

<u>TGAGGACACAGCTGTATATTACTGCGCGCGGATTAAGTTGGGGACCGTCACAACAGTGGATTAC</u>

<u>TGGGGTCAAGGCACTCTGGTAACCGTATCCTCAGCATCCACCAAGGGCCCAAGTGTATTCCCGC</u>

<u>TGGCCCCTTCAAGTAAATCCACGTCTGGCGGCACAGCCGCTCTCGGTTGCCTGGTTAAGGACTA</u>

<u>CTTCCCAGAACCTGTCACTGTCAGTTGGAACTCAGGCGCATTGACATCTGGTGTCCATACATTC</u>

<u>CCCGCAGTCCTGCAAAGCTCTGGACTTTACAGTCTTAGTAGCGTAGTGACAGTCCCATCTTCAA</u>

<u>GTCTTGGGACCCAAACTTATATTTGCAACGTAAATCATAAACCCTCCAACACTAAAGTAGACAA</u>

<u>AAAAGTAGAGCCGAAATCTIGCGACAAAACGCATACATGCCCACCATGTCCCGCTCCGGAACTC</u>

<u>CTGGGCGGCCCGTCCGTTTTTCTCTTTCCCCCAAAGCCCAAGGATACGCTTATGATCAGCAGAA</u>

<u>CACCGGAAGTTACTTGTGTAGTCGTTGACGTGTCTCACGAAGATCCCGAAGTCAAATTTAATTG</u>

<u>GTATGTGGATGGCGTCGAAGTGCACAACGCAAAAACCAAACCCAGAGAGGAACAGTATAACAGC</u>

<u>ACGTATCGAGTGGTCTCCGTACTTACGGTCCTCCACCAGGACTGGTTGAATGGCAAGGAGTACA</u>

<u>AGTGCAAAGTGAGCAATAAAGCGTTGCCAGCCCCGATCGAAAAAACCATCAGCAAGGCCAAGGG</u>

<u>ACAGCCTAGAGAGCCGCAGGTTTACACCTTGCCGCCATCAAGGGATGAACTGACTAAAAACCAG</u>

<u>GTATCCCTGACCTGCCTGGTTAAGGGTTTTTACCCCAGTGATATAGCGGTTGAATGGGAGTCTA</u>

<u>ACGGGCAGCCAGAGAACAACTACAAAACGACACCTCCCGTTCTGGATTCCGATGGCAGCTTTTT</u>

<u>CTTGTATTCTAAACTCACCGTGGATAAATCCCGATGGCAGCAAGGCAACGTCTTCTCCTGCAGC</u>

<u>GTGATGCATGAAGCCTTGCACAACCACTATACCCAAAAGAGTCTCAGCCTGTCACCCGGGAAAT</u>

*CCGGGGGTGGCGGATCCC*TGCGTGCCCATGAGAATGAGATCACCAAAGTGCGAAAAGTTACTTT

CAATGGACTGAACCAGATGATTGTCATAGAACTGGGCACCAATCCGCTGAAGAGCTCAGGAATT

GAAAATGGGGCTTTCCAGGGAATGAAGAAGCTCTCCTACATCCGCATTGCTGATACCAATATCA

CCAGCATTCCTCAAGGTCTTCCTCCTTCCCTTACGGAATTACATCTTGATGGCAACAAAATCAG

CAGAGTTGATGCAGCTAGCCTGAAAGGACTGAATAATTTGGCTAAGTTGGGATTGAGTTTCAAC

AGCATCTCTGCTGTTTGA

Signal peptide coding sequence is shown in boldface type. Heavy chain coding sequence is underlined with a straight line. Linker coding sequence is shown in italics. Galacorin/Decorin (Leu155-Va1260) coding sequence is underlined with a wavy line.

Avelumab-Galacorin/Decorin (Leu155-Va1260 of full length endogenous human Decorin) TGF-Beta Binding Domain Fusion Heavy Chain Protein Sequence (SEQ ID NO:61):
MMSFVSLLLVGILFHATQAEVQLLESGGGLVQPGGSLRLSCAASGFITSSYIMMWVRQAPGKGL

EWVSSIYPSGGITFYADTVKGRFTISRDNSKNTLYLQMNSLRAEDTAVYYCARIKLGTVTTVDY

WGQGTLVTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTVDKSRWQQGNVFSCS

VMHEALHNHYTQKSLSLSPGK*SGGGGS*LRAHENEITKVRKVTFNGLNQMIVIELGTNPLKSSGI

ENGAFQGMKKLSYIRIADTNITSIPQGLPPSLTELHLDGNKISRVDAASLKGLNNLAKLGLSFN

SISAV.

Signal peptide sequence is shown in boldface type. Heavy chain sequence is underlined with a straight line. Linker sequence is shown in italics. Galacorin/Decorin (Leu155-Va1260) sequence is underlined with a wavy line.

Avelumab-Galacorin/Decorin (Leu155-Va1260 of full length endogenous human Decorin) TGF-Beta Binding Domain 2x Fusion Heavy Chain Gene Sequence (SEQ ID NO:62):
ATGATGTCCTTTGTCTCTCTGCTCCTGGTTGGCATCCTATTCCATGCCACCCAGGCCGAGGTAC

AGCTTTTGGAGTCAGGCGGGGGCTCGTCCAACCTGGGGGGTCACTCCGGTTGTCATGTGCTGC

CAGTGGCTTCACATTCTCATCTTACATTATGATGTGGGTTCGACAGGCCCCTGGGAAGGGGCTG

GAGTGGGTTTCCTCCATCTACCCCTCCGGGGGAATTACCTTCTATGCCGACACGGTAAAGGGTC

GCTTCACTATAAGTCGAGATAACAGCAAAAATACGCTGTATCTCCAGATGAACTCTCTCAGGGC

TGAGGACACAGCTGTATATTACTGCGCGCGGATTAAGTTGGGGACCGTCACAACAGTGGATTAC

TGGGGTCAAGGCACTCTGGTAACCGTATCCTCAGCATCCACCAAGGGCCCAAGTGTATTCCCGC

TGGCCCCTTCAAGTAAATCCACGTCTGGCGGCACAGCCGCTCTCGGTTGCCTGGTTAAGGACTA

CTTCCCAGAACCTGTCACTGTCAGTTGGAACTCAGGCGCATTGACATCTGGTGTCCATACATTC

CCCGCAGTCCTGCAAAGCTCTGGACTTTACAGTCTTAGTAGCGTAGTGACAGTCCCATCTTCAA

GTCTTGGGACCCAAACTTATATTTGCAACGTAAATCATAAACCCTCCAACACTAAAGTAGACAA

AAAAGTAGAGCCGAAATCTTGCGACAAAACGCATACATGCCCACCATGTCCCGCTCCGGAACTC

CTGGGCGGCCCGTCCGTTTTTCTCTTTCCCCCAAAGCCCAAGGATACGCTTATGATCAGCAGAA

CACCGGAAGTTACTTGTGTAGTCGTTGACGTGTCTCACGAAGATCCCGAAGTCAAATTTAATTG

GTATGTGGATGGCGTCGAAGTGCACAACGCAAAAACCAAACCCAGAGAGGAACAGTATAACAGC

ACGTATCGAGTGGTCTCCGTACTTACGGTCCTCCACCAGGACTGGTTGAATGGCAAGGAGTACA

AGTGCAAAGTGAGCAATAAAGCGTTGCCAGCCCCGATCGAAAAAACCATCAGCAAGGCCAAGGG

ACAGCCTAGAGAGCCGCAGGTTTACACCTTGCCGCCATCAAGGGATGAACTGACTAAAAACCAG

GTATCCCTGACCTGCCTGGTTAAGGGTTTTTACCCCAGTGATATAGCGGTTGAATGGGAGTCTA

-continued

```
ACGGGCAGCCAGAGAACAACTACAAAACGACACCTCCCGTTCTGGATTCCGATGGCAGCTTTTT

CTTGTATTCTAAACTCACCGTGGATAAATCCCGATGGCAGCAAGGCAACGTCTTCTCCTGCAGC

GTGATGCATGAAGCCTTGCACAACCACTATACCCAAAAGAGTCTCAGCCTGTCACCCGGGAAAT

CCGGGGGTGGCGGATCCCTGCGTGCCCATGAGAATGAGATCACCAAAGTGCGAAAAGTTACTTT

CAATGGACTGAACCAGATGATTGTCATAGAACTGGGCACCAATCCGCTGAAGAGCTCAGGAATT

GAAAATGGGGCTTTCCAGGGAATGAAGAAGCTCTCCTACATCCGCATTGCTGATACCAATATCA

CCAGCATTCCTCAAGGTCTTCCTCCTTCCCTTACGGAATTACATCTTGATGGCAACAAAATCAG

CAGAGTTGATGCAGCTAGCCTGAAAGGACTGAATAATTTGGCTAAGTTGGGATTGAGTTTCAAC

AGCATCTCTGCTGTTTCCGGGGGTGGCGGATCCCTGCGTGCCCATGAGAATGAGATCACCAAAG

TGCGAAAAGTTACTTTCAATGGACTGAACCAGATGATTGTCATAGAACTGGGCACCAATCCGCT

GAAGAGCTCAGGAATTGAAAATGGGGCTTTCCAGGGAATGAAGAAGCTCTCCTACATCCGCATT

GCTGATACCAATATCACCAGCATTCCTCAAGGTCTTCCTCCTTCCCTTACGGAATTACATCTTG

ATGGCAACAAAATCAGCAGAGTTGATGCAGCTAGCCTGAAAGGACTGAATAATTTGGCTAAGTT

GGGATTGAGTTTCAACAGCATCTCTGCTGTTTGA
```

Signal peptide coding sequence is shown in boldface type. Heavy chain coding sequence is underlined with a straight line. Linker coding sequences are shown in italics. Galacorin/Decorin (Leu155-Val260) coding sequences are underlined with a wavy line.

Avelumab-Galacorin/Decorin (Leu155-Val260 of full length endogenous human Decorin) TGF-Beta Binding Domain 2x Fusion Heavy Chain Protein Sequence (SEQ ID NO:63):
MMSFVSLLLVGILFHATQAEVQLLESGGGLVQPGGSLRLSCAASGFTFSSYIMMWVRQAPGKGL

EWVSSIYPSGGITFYADTVKGRFTISRDNSKNTLYLQMNSLRAEDTAVYYCARIKLGTVTTVDY

WGQGTLVTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTVDKSRWQQGNVFSCS

VMHEALHNHYTQKSLSLSPGK*SGGGGS*LRAHENEITKVRKVTFNGLNQMIVIELGTNPLKSSGI

ENGAFQGMKKLSYIRIADTNITSIPQGLPPSLTELHLDGNKISRVDAASLKGLNNLAKLGLSFN

SISAV*SGGGGS*LRAHENEITKVRKVTFNGLNQMIVIELGTNPLKSSGIENGAFQGMKKLSYIRI

ADTNITSIPQGLPPSLTELHLDGNKISRVDASLKGLNNLAKLGLSFNSISAV.

Signal peptide sequence is shown in boldface type. Heavy chain sequence is underlined with a straight line. Linker sequences are shown in italics. Galacorin/Decorin (Leu155-Val1260) sequences are underlined with a wavy line.

Example 2

This example describes the production of expression cells lines for the production of the fusion proteins described in Example 1.

Figure 3:
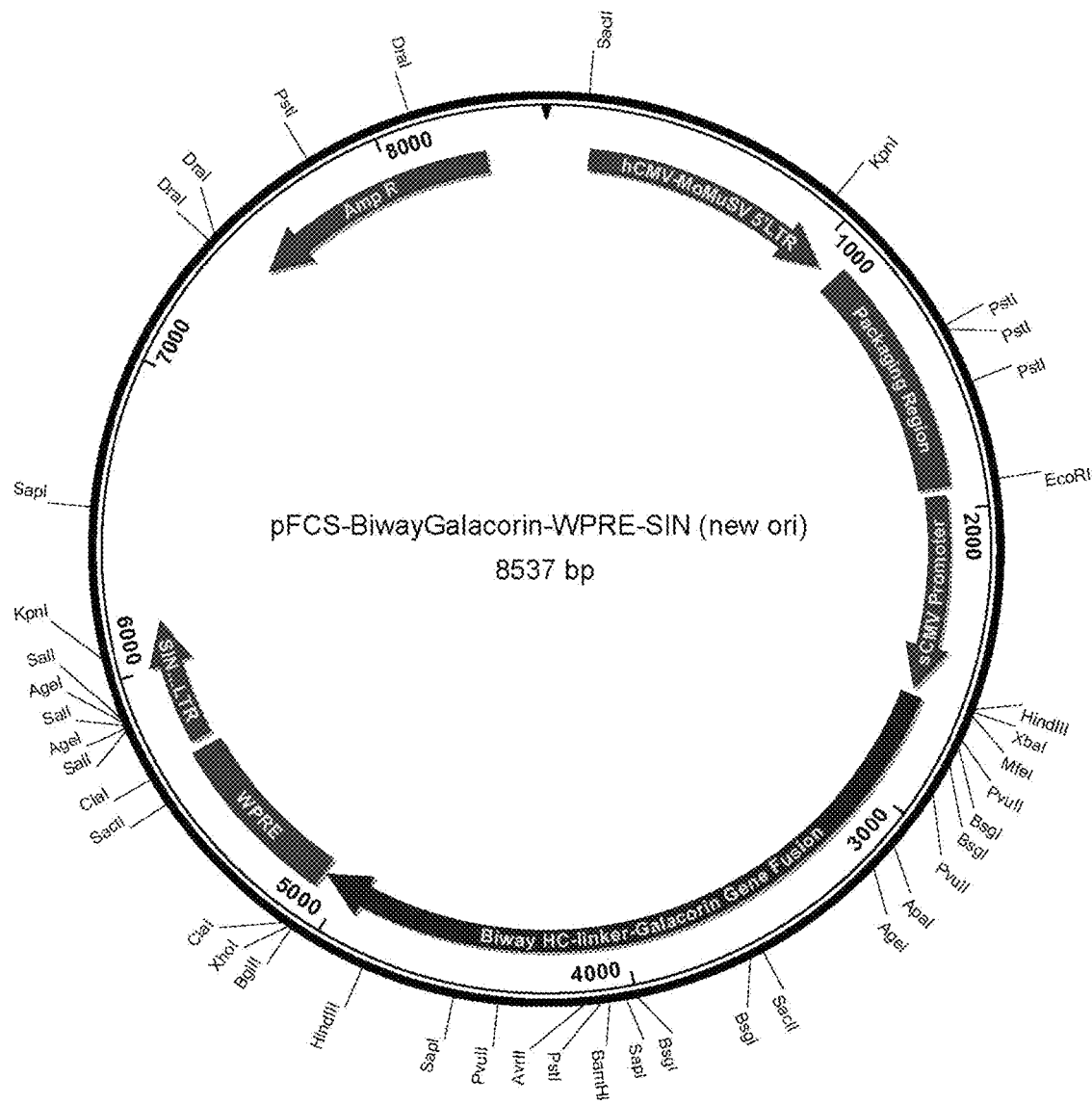
FIG. 3 is a map of an expression construct of the present invention.

Retrovector Production: The expression constructs outlined above were introduced into a HEK 293 cell line that constitutively produces the MLV gag, pro, and pol proteins. An envelope containing expression plasmid was also co-tranfected with either the bevacizumab light chain (See FIG. 2 for vector map) or bevacizumab heavy chain-galacorin fusion (See FIG. 3 for vector map) gene construct. The two co-transfections resulted in the production of replication incompetent high titer retrovector for either light chain or heavy chain-galacorin, that was concentrated by ultracentrifugation and used for cell transductions (See, e.g., Bleck, G. T. 2005 An alternative method for the rapid generation of stable, high-expressing mammalian cell lines (A Technical Review). Bioprocessing J. September/October pp 1-7; Bleck, G. T., 2010. GPEx® A Flexible Method for the Rapid Generation of Stable, High Expressing, Antibody Producing Mammalian Cell Lines Chapter 4 In: Current Trends in Monoclonal Antibody Development and Manufacturing, Biotechnology: Pharmaceutical Aspects, Edited by: S. J. Shire et al. © 2010 American Association of Pharmaceutical Scientists, DOI 10.1007/978-0-387-76643-0_4.).

Summary. Features of pCS-Bi-wayLC-WPRE (new ori), GDD2107.0003

| Component | Description | Function/Notes |
|---|---|---|
| 5' hCMV-MoMuSV LTR (R-U5)<br>bp 142-766 hCMV promoter<br>bp 767-911 MoMuSV R-U5 | A fusion of the human CMV promoter to the R-U5 regions of the Moloney Murine Sarcoma Virus 5' LTR | The human cytomegalovirus IE promoter has strong constitutive activity in most mammalian cells. Used to create high titer of retrovector particles when transfected into packaging cells.<br>The hCMV promoter is lost after the packaging cell step. |
| Extended packaging region<br>bp 981-1790 | MoMuLV/SV packaging region from the LTR through a mutated ATG site in the MLV Gag gene | Packaging region allows creation of retrovector particles by allowing RNA to associate with MoMuLV Gag/Pol gene products. |
| sCMV promoter<br>bp 1822-2424 | The immediate early promoter from simian CMV | Alternative strong constitutive promoter to drive expression of product gene. |
| Biway light chain gene<br>bp 2510-3211 | Biway light chain CDS | Biway light chain CDS directly cloned from Bio Basic's pUC57 plasmid |
| WPRE<br>bp 3230-3830 | A fragment from the woodchuck hepatitis B virus Pol gene | Region that is thought to aid export of unspliced RNA and improve protein expression. |
| 3' LTR<br>bp 3870-4463 | The 3' LTR from MoMuLV | Functions as a Poly A signal for RNA. Allows reverse transcription and DNA insertion of retrovector into mammalian cells from retrovector particles. |
| Plasmid backbone - E. coli origin of replication and β-lactamase gene for ampicillin resistance<br>bp 5765 < 6625<br>bp 1-148 | Basic E. coli plasmid sequences | Allows selection of plasmid containing bacteria in E. coli and replication of DNA in E. coli.<br>These regions are lost after transfecting plasmids into packaging cells and creating retrovector particles. |

Summary: Features of pFCS-BiwayGalacorin-WPRE-SIN (new ori), GDD2134.0001

| Component | Description | Function/Notes |
|---|---|---|
| 5' hCMV-MoMuSV LTR (R-U5)<br>bp 149-865 hCMV promoter<br>bp 866-1041 MoMuSV R-U5 | A fusion of the full-length human CMV promoter to the R-U5 regions of the Moloney Murine Sarcoma Virus 5' LTR | The human cytomegalovirus IE promoter has strong constitutive activity in most mammalian cells. Used to create high titer of retrovector particles when transfected into packaging cells.<br>The hCMV promoter is lost after the packaging cell step. |
| Extended packaging region<br>bp 1111-1920 | MoMuLV/SV packaging region from the LTR through a mutated ATG site in the MLV Gag gene | Packaging region allows creation of retrovector particles by allowing RNA to associate with MoMuLV Gag/Pol gene products. |
| sCMV promoter<br>bp 1952-2624 | The immediate early promoter from simian CMV | Alternative strong constitutive promoter to drive expression of product gene. |
| Biway HC-Galacorin gene fusion<br>bp 2650-5073 | Biway HC-Galacorin CDS | Full Biway HC-linker-Galacorin CDS assembled by PCR and cloned by restriction digestion |

-continued

| Component | Description | Function/Notes |
|---|---|---|
| WPRE<br>bp 5089-5689 | A fragment from the woodchuck Hepatitis B virus Pol gene | Region that is thought to aid export of unspliced RNA and improve protein expression. |
| SIN 3' LTR<br>bp 5730-6153 | The 3' LTR from MoMuLV | Functions as a Poly A signal for RNA. Allows reverse transcription and DNA insertion of retrovector into mammalian cells from retrovector particles. In proviral DNA deletion in U3 region is duplicated to 5' LTR hereby inactivating 5' LTR promoter activity. |
| Plasmid backbone - E. coli origin of replication and β-lactamase gene for ampicillin resistance<br>bp 7472-8332<br>bp 1-148 | Basic E. coli plasmid sequences | Allows selection of plasmid containing bacteria in E. coli and replication of DNA in E. coli.<br>These regions are lost after transfecting plasmids into packaging cells and creating retrovector particles. |

Transduction of GCHO Cells with Retrovector: The bevacizumab-galacorin fusion antibody pooled cell line was produced by multiple cycles of cell transduction of the GPEx® Chinese Hamster Ovary (GCHO) parental cell line, with two light chain transductions followed by two heavy chain-galacorin transductions performed once a week over the span of 4 weeks. These transductions were performed to generate a pooled cell line each of the two gene products.

Figure 4:
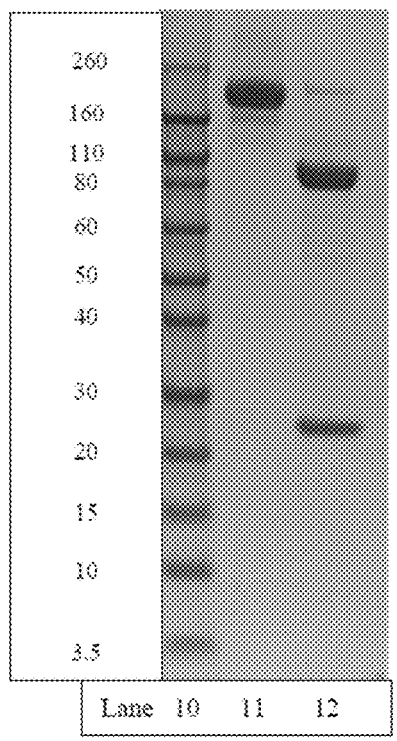
FIG. 4 is a SDS-PAGE gel of media from the pooled CHO cell line expressing the bevacizumab fusion protein. Lane 10. Molecular weight standards. Lane 11. Non-reduced media sample. Lane 12. Reduced media sample.

Fed Batch Production of Bevacizumab-Galacorin Fusion from the Pooled Population of Cells: Post-transduction, the pooled cell line for the Bevacizumab-Galacorin Fusion was scaled up for productivity in a fed batch study in duplicate 250 mL shake flasks. Each shake flask was seeded with 300,000 viable cells per mL in a 60 mL working volume of PF CHO LS media (HyClone) and incubated in a humidified (70-80%) shaking incubator at 130 rpm with 5% $CO_2$ and temperature of 37° C. Cultures were fed four times during the production run using two different feed supplements. Cultures were terminated when viabilities were ≤70%. Confirmation of the fusion antibody production was determined by SDS-PAGE gel analysis (FIG. 4) and by ELISA to quantitate the amount of product produced. The cultures produce 360 mg/L of the fusion antibody product. The product behave as expected in SDS-PAGE showing a predominant single band under non-reduced conditions and two bands (Heavy chain-galacorin fusion and light chain) under reduced conditions. The ~80 kDa size of the fusion heavy chain matches the expected size of that product and the light chain is the normal '25 kDa in size.

Example 3

This example describes expression of an Avelumab-Galacorin fusion.

Figure 5:
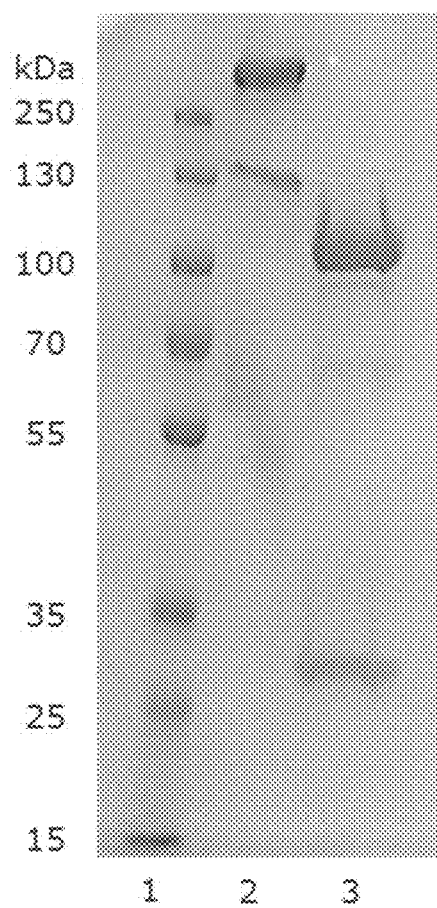
FIG. 5 is a SDS-PAGE gel of purified Avelumab-Galacorin fusion molecule. Lane 1: Molecular weight markers. Lane 2: Non-reduced purified Avelumab-Galacorin fusion. Lane 3: Reduced purified Avelumab-Galacorin fusion.
Figure 6:
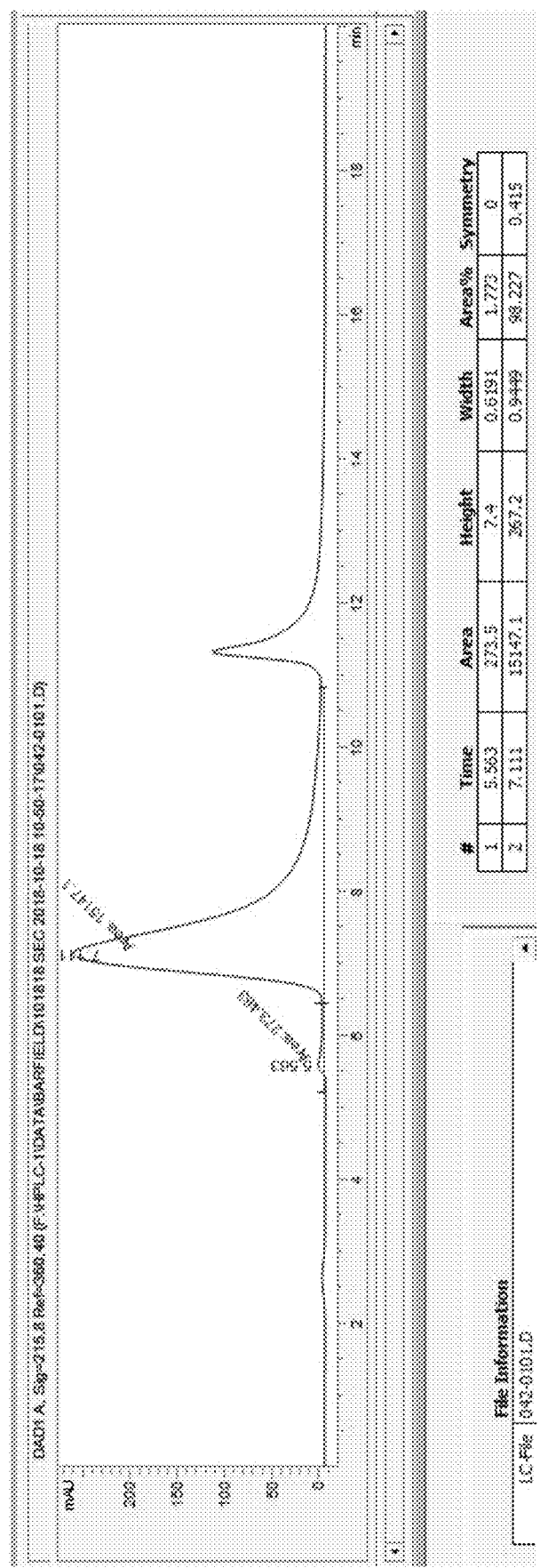
FIG. 6 is a SEC-HPLC chromatogram of purified Avelumab-Galacorin fusion molecule. Percent monomer was greater than 98%.

The gene construct of SEQ ID NO:50 was transiently transfected into ExpiCHO cells and production of the fusion molecule was performed at the 250 ml scale. The titer of the fusion on day of harvest was 377 mg/L. The fusion was purified over a MabSelectSuRe protein A column. The resulting purified protein was buffer exchanged into 20 mM NaCitrate, pH 5.5, 50 mM NaCl using tangential flow filtration. The resulting material was examined using SDS-PAGE gels and SEC-HPLC. The product showed expected size profile on the SDS-PAGE gel (FIG. 5) and showed very low aggregation levels on SEC-HPLC (FIG. 6).

Material produced in the above production was used for evaluation in a mouse tumor model study. The study used C57BL/6 mice and the MC-38 human colorectal cancer cells. Forty C57BL/6 mice were injected subcutaneously with MC-38 cells. Tumors were allowed to grow to approximately 100 $mm^3$ and then 10 mice each were assigned to 4 different treatments. Each group received a single dose treatment IV and tumor size was measure over subsequent days. Treatment groups were Vehicle, Galacorin/Decorin 4 mg/kg, Avelumab/Anti-PD-L1 17 mg/kg, or Avelumab/Anti PD-L1-Decorin/Galacorin fusion 25 mg/kg.

Figure 7:
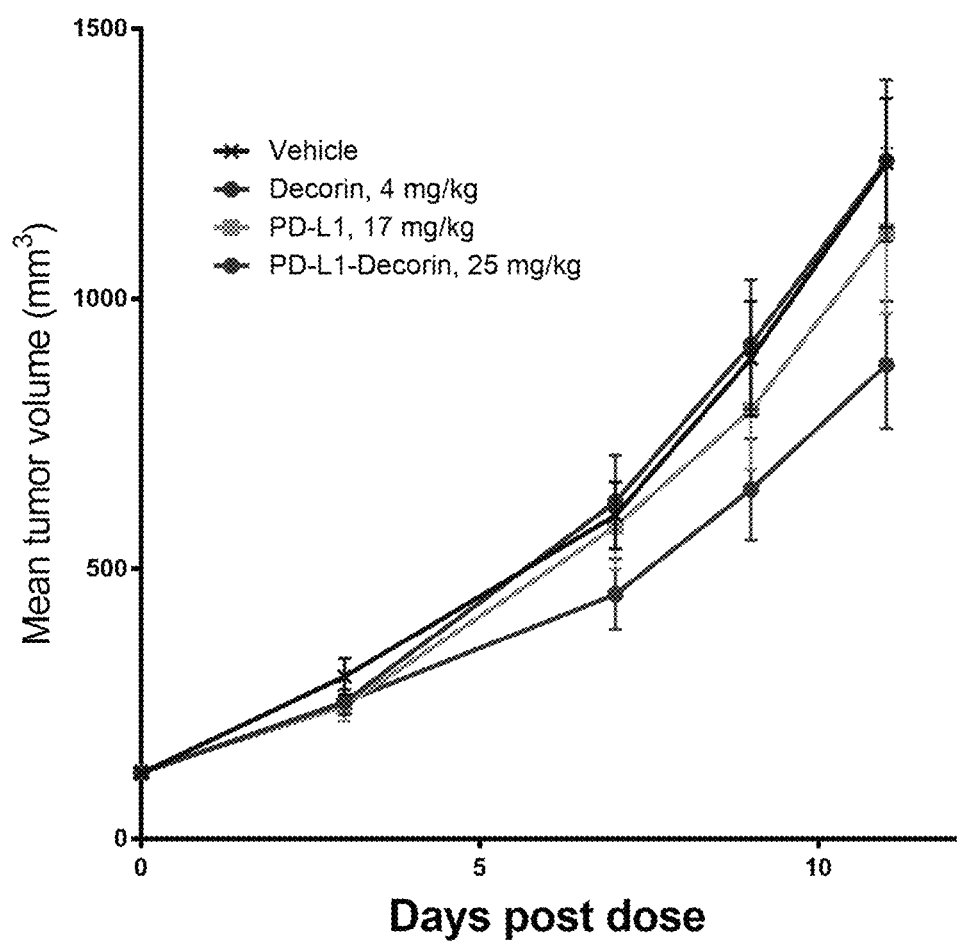
FIG. 7 is a graph of tumor growth in a C57BL/6 mouse MC-38 human colorectal cancer model after a single IV dose of the four treatments.

Tumor growth was inhibited by both the Avelumab/Anti-PD-L1 and Avelumab/Anti PD-L1-Decorin/Galacorin fusion treatments as compared to Vehicle and Decorin/Galacorin alone (FIG. 7). In addition, Avelumab/Anti PD-L1-Decorin/Galacorin fusion treatment also inhibited growth more effectively than Avelumab/Anti-PD-L1 alone.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of this invention are intended to be within the scope of the following claims.

What is claimed is:

1. A multifunctional protein molecule comprising at least one decorin molecule having at least 95% sequence identity to SEQ ID NO:7 linked to an antibody molecule selected from the group consisting of bevacizumab, ranibizumab, ipilimumab, atezolizumab, avelumab, durvalumab, nivolumab and pembrolizumab.

2. The multifunctional protein molecule of claim 1, wherein the decorin molecule comprises a mutation at position 4 as compared to wild-type decorin.

3. The multifunctional protein molecule of claim 2, wherein the mutation is a serine to alanine mutation.

4. The multifunctional protein molecule of claim 2, wherein the decorin molecule lacks modification by glycosaminoglycans molecules at position 4 of the decorin molecule.

5. The multifunctional protein molecule of claim 1, wherein the multifunctional protein molecule comprises two or more copies of the decorin molecule.

6. The multifunctional protein molecule of claim 1, wherein the decorin molecule comprises a decorin domain or domains that binds a signaling molecule selected from the group consisting of Transforming Growth Factor-β (TGF-β), Connective Tissue Growth Factor (CTGF), Platelet-Derived Growth Factor (PDGF), Vascular Endothelial Growth Factor Receptor 2 (VEGFR2), Hepatocyte Growth Factor Receptor (HGFR), Insulin-like Growth Factor 1 Receptor (IGF-1R), Epidermal Growth Factor Receptors (EGFRs), myostatin and C1q.

7. The multifunctional protein molecule of claim 6, wherein the TGF-β binding domain comprises amino acids Asp45-Lys359 of full length endogenous human decorin or amino acids Leu155-Val260 of full length endogenous human decorin.

8. The multifunctional protein molecule of claim 6, wherein the multifunctional protein molecule comprises two or more copies of the decorin molecule.

9. The multifunctional protein molecule of claim 1, wherein the decorin molecule is operably linked to a heavy chain of the antibody.

10. The multifunctional protein molecule of claim 1, wherein the multifunctional protein molecule is a fusion protein.

11. The multifunctional protein molecule of claim 1, wherein the decorin molecule is chemically linked to the antigen binding protein.

12. A nucleic acid or set of nucleic acids encoding a multifunctional protein molecule of claim 1.

13. A vector or vectors comprising the nucleic acid or set of nucleic acids of claim 12.

14. A host cell comprising the vector or vectors of claim 13.

15. A method of treating a disorder characterized by angiogenesis or tumor growth, comprising:
  administering the multifunctional protein molecule of claim 1 to a subject under conditions such that angiogenesis or tumor growth is inhibited in the subject.

16. The method of claim 15, wherein the tumor is selected from the group consisting of lung cancer, colorectal cancer, liver cancer, breast cancer, kidney cancer, cervical cancer, ovarian cancer, and glioblastoma.

* * * * *

SEQUENCE LISTING

```
<160> NUMBER OF SEQ ID NOS: 66

<210> SEQ ID NO 1
<211> LENGTH: 2424
<212> TYPE: DNA
<213> ORGANISM: Artificial Sequence
<220> FEATURE:
```

<223> OTHER INFORMATION: synthetic

<400> SEQUENCE: 1

```
atgatgtcct ttgtctctct gctcctggtt ggcatcctat tccatgccac ccaggccgag      60
gtgcagctgg tggagtctgg gggaggcttg gtacagcctg gggggtccct gagactctcc     120
tgtgcagcct ctggatacac ctttaccaac tatggcatga actgggtccg ccaggctcca     180
gggaaggggc tggagtgggt gggctggata aacacttaca ctggtgagcc aacatatgca     240
gctgacttca gcgccggtt taccttctct ttggacacct ccaagtccac ggcctatctg      300
caaatgaaca gcctgcgggc cgaggacacg gccgtatatt actgtgcgaa ataccccac      360
tactacggta gtagccactg gtactttgac gtgtggggcc agggaaccct ggtcaccgtc     420
tcctcagcct ccaccaaggg cccatcggtc ttccccctgg cacctcctc caagagcacc      480
tctggggca cagcggccct gggctgcctg gtcaaggact acttccccga accggtgacg      540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagaaagtt     720
gagcccaaat cttgtgacaa aactcacaca tgcccaccgt gcccagcacc tgaactcctg     780
gggggaccgt cagtcttcct cttccccca aaacccaagg acaccctcat gatctcccgg      840
accctgagg tcacatgcgt ggtggtggac gtgagccacg aagaccctga ggtcaagttc      900
aactggtacg tggacggcgt ggaggtgcat aatgccaaga caaagccgcg ggaggagcag     960
tacaacagca cgtaccgggt ggtcagcgtc ctcaccgtcc tgcaccagga ctggctgaat    1020
ggcaaggagt acaagtgcaa ggtctccaac aaagccctcc cagcccccat cgagaaaacc    1080
atctccaaag ccaaagggca gccccgagaa ccacaggtgt acaccctgcc cccatcccgg    1140
gaggagatga ccaagaacca ggtcagcctg acctgcctgg tcaaaggctt ctatcccagc    1200
gacatcgccg tggagtggga gagcaatggg cagccggaga caactacaa gaccacgcct     1260
cccgtgctgg actccgacgg ctccttcttc ctctacagca agctcaccgt ggacaagagc    1320
aggtggcagc aggggaacgt cttctcatgc tccgtgatgc atgaggctct gcacaaccac    1380
tacacgcaga agagcctctc cctgtctccc gggaaatccg ggggtggcgg atccgatgag    1440
gctgcaggga taggcccaga agttcctgat gaccgcgact cgagccctc cctaggccca     1500
gtgtgccct tccgctgtca atgccatctt cgagtggtcc agtgttctga tttgggtctg     1560
gacaaagtgc caaggatct cccccctgac acaactctgc tagacctgca aaacaacaaa    1620
ataaccgaaa tcaaagatgg agactttaag aacctgaaga accttcacgc attgattctt    1680
gtcaacaata aaattagcaa agttagtcct ggagcattta ccctttggt gaagttggaa      1740
cgactttatc tgtccaagaa tcagctgaag gaattgccag aaaaaatgcc caaaactctt    1800
caggagctgc gtgcccatga gaatgagatc accaaagtgc gaaaagttac tttcaatgga    1860
ctgaaccaga tgattgtcat agaactgggc accaatccgc tgaagagctc aggaattgaa    1920
aatgggctt ccagggaat gaagaagctc tcctacatcc gcattgctga taccaatatc      1980
accagcattc ctcaaggtct tcctccttcc cttacggaat acatcttga tggcaacaaa    2040
atcagcagag ttgatgcagc tagcctgaaa ggactgaata atttggctaa gttgggattg    2100
agtttcaaca gcatctctgc tgttgacaat ggctctctgg ccaacacgcc tcatctgagg    2160
gagcttcact tggacaacaa caagcttacc agagtacctg gtgggctggc agagcataag    2220
tacatccagg ttgtctacct tcataacaac aatatctctg tagttggatc aagtgacttc    2280
```

-continued

```
tgcccacctg gacacaacac caaaaaggct tcttattcgg gtgtgagtct tttcagcaac    2340
ccggtccagt actgggagat acagccatcc accttcagat gtgtctacgt gcgctctgcc    2400
attcaactcg gaaactataa gtga                                           2424
```

<210> SEQ ID NO 2
<211> LENGTH: 807
<212> TYPE: PRT
<213> ORGANISM: Artificial Sequence
<220> FEATURE:
<223> OTHER INFORMATION: synthetic

<400> SEQUENCE: 2

```
Met Met Ser Phe Val Ser Leu Leu Val Gly Ile Leu Phe His Ala
1               5                   10                  15

Thr Gln Ala Glu Val Gln Leu Val Glu Ser Gly Gly Gly Leu Val Gln
            20                  25                  30

Pro Gly Gly Ser Leu Arg Leu Ser Cys Ala Ala Ser Gly Tyr Thr Phe
        35                  40                  45

Thr Asn Tyr Gly Met Asn Trp Val Arg Gln Ala Pro Gly Lys Gly Leu
    50                  55                  60

Glu Trp Val Gly Trp Ile Asn Thr Tyr Thr Gly Glu Pro Thr Tyr Ala
65                  70                  75                  80

Ala Asp Phe Lys Arg Arg Phe Thr Phe Ser Leu Asp Thr Ser Lys Ser
                85                  90                  95

Thr Ala Tyr Leu Gln Met Asn Ser Leu Arg Ala Glu Asp Thr Ala Val
            100                 105                 110

Tyr Tyr Cys Ala Lys Tyr Pro His Tyr Tyr Gly Ser Ser His Trp Tyr
        115                 120                 125

Phe Asp Val Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335
```

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
            450                 455                 460

Ser Leu Ser Leu Ser Pro Gly Lys Ser Gly Gly Gly Ser Asp Glu
465                 470                 475                 480

Ala Ala Gly Ile Gly Pro Glu Val Pro Asp Asp Arg Asp Phe Glu Pro
                485                 490                 495

Ser Leu Gly Pro Val Cys Pro Phe Arg Cys Gln Cys His Leu Arg Val
            500                 505                 510

Val Gln Cys Ser Asp Leu Gly Leu Asp Lys Val Pro Lys Asp Leu Pro
            515                 520                 525

Pro Asp Thr Thr Leu Leu Asp Leu Gln Asn Asn Lys Ile Thr Glu Ile
            530                 535                 540

Lys Asp Gly Asp Phe Lys Asn Leu Lys Asn Leu His Ala Leu Ile Leu
545                 550                 555                 560

Val Asn Asn Lys Ile Ser Lys Val Ser Pro Gly Ala Phe Thr Pro Leu
                565                 570                 575

Val Lys Leu Glu Arg Leu Tyr Leu Ser Lys Asn Gln Leu Lys Glu Leu
            580                 585                 590

Pro Glu Lys Met Pro Lys Thr Leu Gln Glu Leu Arg Ala His Glu Asn
            595                 600                 605

Glu Ile Thr Lys Val Arg Lys Val Thr Phe Asn Gly Leu Asn Gln Met
610                 615                 620

Ile Val Ile Glu Leu Gly Thr Asn Pro Leu Lys Ser Ser Gly Ile Glu
625                 630                 635                 640

Asn Gly Ala Phe Gln Gly Met Lys Lys Leu Ser Tyr Ile Arg Ile Ala
                645                 650                 655

Asp Thr Asn Ile Thr Ser Ile Pro Gln Gly Leu Pro Pro Ser Leu Thr
            660                 665                 670

Glu Leu His Leu Asp Gly Asn Lys Ile Ser Arg Val Asp Ala Ala Ser
            675                 680                 685

Leu Lys Gly Leu Asn Asn Leu Ala Lys Leu Gly Leu Ser Phe Asn Ser
            690                 695                 700

Ile Ser Ala Val Asp Asn Gly Ser Leu Ala Asn Thr Pro His Leu Arg
705                 710                 715                 720

Glu Leu His Leu Asp Asn Asn Lys Leu Thr Arg Val Pro Gly Gly Leu
                725                 730                 735

Ala Glu His Lys Tyr Ile Gln Val Val Tyr Leu His Asn Asn Asn Ile
            740                 745                 750

Ser Val Val Gly Ser Ser Asp Phe Cys Pro Pro Gly His Asn Thr Lys
            755                 760                 765

Lys Ala Ser Tyr Ser Gly Val Ser Leu Phe Ser Asn Pro Val Gln Tyr
        770                 775                 780

Trp Glu Ile Gln Pro Ser Thr Phe Arg Cys Val Tyr Val Arg Ser Ala
785                 790                 795                 800

Ile Gln Leu Gly Asn Tyr Lys
                805

<210> SEQ ID NO 3
<211> LENGTH: 702
<212> TYPE: DNA
<213> ORGANISM: Artificial Sequence
<220> FEATURE:
<223> OTHER INFORMATION: synthetic

<400> SEQUENCE: 3

| | | |
|---|---|---|
| atgatgtcct tgtctctct gctcctggtt ggcatcctgt tccatgccac ccaggccgac | 60 |
| atccagatga cccagtctcc atcctccctg tctgcatctg taggagacag agtcaccatc | 120 |
| acttgcagtg caagtcagga cattagcaat tatttaaact ggtatcagca gaaaccaggg | 180 |
| aaagctccta aggtcctgat ctatttcaca tccagtttgc actcaggggt cccatctagg | 240 |
| ttcagtggca gtggatctgg gacagatttc actctcacca tcagcagcct gcagcctgaa | 300 |
| gattttgcaa cttattactg ccaacagtat agtaccgtgc cttggacgtt cggccaaggg | 360 |
| accaaggtgg aaatcaaacg aactgtggct gcaccatctg tcttcatctt cccgccatct | 420 |
| gatgagcagc ttaagtccgg aactgctagc gttgtgtgcc tgctgaataa cttctatccc | 480 |
| agagaggcca agtacagtg gaaggtggat aacgccctcc aatcgggtaa ctcccaggag | 540 |
| agtgtcacag agcaggacag caaggacagc acctacagcc tcagcagcac cctgacgctg | 600 |
| agcaaagcag actacgagaa acacaaagtc tacgcctgcg aagtcaccca tcagggcctg | 660 |
| agctcgcccg tcacaaagag cttcaacagg ggagagtgtt ag | 702 |

<210> SEQ ID NO 4
<211> LENGTH: 233
<212> TYPE: PRT
<213> ORGANISM: Artificial Sequence
<220> FEATURE:
<223> OTHER INFORMATION: synthetic

<400> SEQUENCE: 4

Met Met Ser Phe Val Ser Leu Leu Leu Val Gly Ile Leu Phe His Ala
1               5                   10                  15

Thr Gln Ala Asp Ile Gln Met Thr Gln Ser Pro Ser Ser Leu Ser Ala
            20                  25                  30

Ser Val Gly Asp Arg Val Thr Ile Thr Cys Ser Ala Ser Gln Asp Ile
        35                  40                  45

Ser Asn Tyr Leu Asn Trp Tyr Gln Gln Lys Pro Gly Lys Ala Pro Lys
    50                  55                  60

Val Leu Ile Tyr Phe Thr Ser Ser Leu His Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Ser Thr
            100                 105                 110

Val Pro Trp Thr Phe Gly Gln Gly Thr Lys Val Glu Ile Lys Arg Thr
        115                 120                 125

```
Val Ala Ala Pro Ser Val Phe Ile Phe Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 5
<211> LENGTH: 19
<212> TYPE: PRT
<213> ORGANISM: Artificial Sequence
<220> FEATURE:
<223> OTHER INFORMATION: synthetic

<400> SEQUENCE: 5

```
Met Met Ser Phe Val Ser Leu Leu Leu Val Gly Ile Leu Phe His Ala
1               5                   10                  15

Thr Gln Ala
```

<210> SEQ ID NO 6
<211> LENGTH: 6
<212> TYPE: PRT
<213> ORGANISM: Artificial Sequence
<220> FEATURE:
<223> OTHER INFORMATION: synthetic

<400> SEQUENCE: 6

```
Ser Gly Gly Gly Gly Ser
1               5
```

<210> SEQ ID NO 7
<211> LENGTH: 329
<212> TYPE: PRT
<213> ORGANISM: Artificial Sequence
<220> FEATURE:
<223> OTHER INFORMATION: synthetic

<400> SEQUENCE: 7

```
Asp Glu Ala Ala Gly Ile Gly Pro Glu Val Pro Asp Asp Arg Asp Phe
1               5                   10                  15

Glu Pro Ser Leu Gly Pro Val Cys Pro Phe Arg Cys Gln Cys His Leu
                20                  25                  30

Arg Val Val Gln Cys Ser Asp Leu Gly Leu Asp Lys Val Pro Lys Asp
            35                  40                  45

Leu Pro Pro Asp Thr Thr Leu Leu Asp Leu Gln Asn Asn Lys Ile Thr
        50                  55                  60

Glu Ile Lys Asp Gly Asp Phe Lys Asn Leu Lys Asn Leu His Ala Leu
65                  70                  75                  80

Ile Leu Val Asn Asn Lys Ile Ser Lys Val Ser Pro Gly Ala Phe Thr
                85                  90                  95

Pro Leu Val Lys Leu Glu Arg Leu Tyr Leu Ser Lys Asn Gln Leu Lys
```

```
                100             105             110
Glu Leu Pro Glu Lys Met Pro Lys Thr Leu Gln Glu Leu Arg Ala His
            115                 120                 125
Glu Asn Glu Ile Thr Lys Val Arg Lys Val Thr Phe Asn Gly Leu Asn
        130                 135                 140
Gln Met Ile Val Ile Glu Leu Gly Thr Asn Pro Leu Lys Ser Ser Gly
145                 150                 155                 160
Ile Glu Asn Gly Ala Phe Gln Gly Met Lys Lys Leu Ser Tyr Ile Arg
                165                 170                 175
Ile Ala Asp Thr Asn Ile Thr Ser Ile Pro Gln Gly Leu Pro Pro Ser
            180                 185                 190
Leu Thr Glu Leu His Leu Asp Gly Asn Lys Ile Ser Arg Val Asp Ala
        195                 200                 205
Ala Ser Leu Lys Gly Leu Asn Asn Leu Ala Lys Leu Gly Leu Ser Phe
    210                 215                 220
Asn Ser Ile Ser Ala Val Asp Asn Gly Ser Leu Ala Asn Thr Pro His
225                 230                 235                 240
Leu Arg Glu Leu His Leu Asp Asn Asn Lys Leu Thr Arg Val Pro Gly
                245                 250                 255
Gly Leu Ala Glu His Lys Tyr Ile Gln Val Val Tyr Leu His Asn Asn
            260                 265                 270
Asn Ile Ser Val Val Gly Ser Ser Asp Phe Cys Pro Pro Gly His Asn
        275                 280                 285
Thr Lys Lys Ala Ser Tyr Ser Gly Val Ser Leu Phe Ser Asn Pro Val
    290                 295                 300
Gln Tyr Trp Glu Ile Gln Pro Ser Thr Phe Arg Cys Val Tyr Val Arg
305                 310                 315                 320
Ser Ala Ile Gln Leu Gly Asn Tyr Lys
                325

<210> SEQ ID NO 8
<211> LENGTH: 453
<212> TYPE: PRT
<213> ORGANISM: Artificial Sequence
<220> FEATURE:
<223> OTHER INFORMATION: synthetic

<400> SEQUENCE: 8

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Asn Tyr
            20                  25                  30
Gly Met Asn Trp Val Arg Gln Ala Pro Gly Lys Gly Leu Glu Trp Val
        35                  40                  45
Gly Trp Ile Asn Thr Tyr Thr Gly Glu Pro Thr Tyr Ala Ala Asp Phe
    50                  55                  60
Lys Arg Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Lys Tyr Pro His Tyr Tyr Gly Ser Ser His Trp Tyr Phe Asp Val
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
```

```
                130                 135                 140
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
        450

<210> SEQ ID NO 9
<211> LENGTH: 214
<212> TYPE: PRT
<213> ORGANISM: Artificial Sequence
<220> FEATURE:
<223> OTHER INFORMATION: synthetic

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
```

```
            35                  40                  45
Tyr Phe Thr Ser Ser Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 10
<211> LENGTH: 2409
<212> TYPE: DNA
<213> ORGANISM: Artificial Sequence
<220> FEATURE:
<223> OTHER INFORMATION: synthetic

<400> SEQUENCE: 10

```
atgatgtcct ttgtctctct gctcctggtt ggcatcctat tccatgccac ccaggcccag    60
gtgcagctgg tggagtccgg cggcggcgtc gtgcagcccg gccggtccct gcggctgtcc   120
tgcgccgcct ccggcttcac cttctcctcc tacaccatgc actgggtgcg gcaggccccc   180
ggcaagggcc tggagtgggt gactttcatc tcctacgacg gcaacaacaa gtactacgcc   240
gactccgtga agggccggtt caccatctcc cgcgacaact ccaagaacac cctgtacctg   300
cagatgaact ccctgcgggc cgaggacacc gccatctact actgcgcccg gaccggctgg   360
ctgggcccct cgactactg gggccagggc accctggtga ccgtgtcctc cgcctccacc   420
aagggcccat cggtcttccc cctggcaccc tctagcaaga gcacctctgg gggcacagcg   480
gccctgggct gcctggtcaa ggactacttc cccgaaccgg tgacggtgtc gtggaactca   540
ggcgccctga ccagcggcgt gcacaccttc ccggctgtcc tacagtcctc aggactctac   600
tccctcagca gcgtggtgac cgtgccctcc agcagcttgg gcacccagac ctacatctgc   660
aacgtgaatc acaagcccag caacaccaag gtggacaagc gggttgagcc caaatcttgt   720
gacaaaactc acacatgccc accgtgccca gcacctgaac tcctgggggg accgtcagtc   780
ttcctcttcc ccccaaaacc caaggacacc ctcatgatct cccggacccc tgaggtcaca   840
tgcgtggtgg tggacgtgag ccacgaagac cctgaggtca agttcaactg gtacgtggac   900
ggcgtggagg tgcataatgc caagacaaag ccgcgggagg agcagtacaa cagcacgtac   960
cgtgtggtca gcgtcctcac cgtcctgcac caggactggc tgaatggcaa ggagtacaag  1020
```

```
tgcaaggtct ccaacaaagc cctcccagcc cccatcgaga aaaccatctc caaagccaaa    1080
gggcagcccc gagaaccaca ggtgtacacc ctgcctccat cccgcgatga gctgaccaag    1140
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta tagcaagctc accgtggaca agagcaggtg gcagcagggg    1320
aacgtcttct catgctccgt gatgcatgag gctctgcaca accactacac gcagaagagc    1380
ctctccctgt ctcctgggaa atccggggggt ggcggatccg atgaggctgc agggataggc    1440
ccagaagttc ctgatgaccg cgacttcgag ccctccctag gcccagtgtg ccccttccgc    1500
tgtcaatgcc atcttcgagt ggtccagtgt tctgatttgg gtctggacaa agtgccaaag    1560
gatcttcccc ctgacacaac tctgctagac ctgcaaaaca acaaaataac cgaaatcaaa    1620
gatggagact ttaagaacct gaagaacctt cacgcattga ttcttgtcaa caataaaatt    1680
agcaaagtta gtcctggagc atttacacct ttggtgaagt tggaacgact ttatctgtcc    1740
aagaatcagc tgaaggaatt gccagaaaaa atgcccaaaa ctcttcagga gctgcgtgcc    1800
catgagaatg agatcaccaa agtgcgaaaa gttactttca atggactgaa ccagatgatt    1860
gtcatagaac tgggcaccaa tccgctgaag agctcaggaa ttgaaaatgg ggctttccag    1920
ggaatgaaga agctctccta catccgcatt gctgatacca atatcaccag cattcctcaa    1980
ggtcttcctc cttcccttac ggaattacat cttgatggca caaaatcag cagagttgat    2040 gcagctagcc tgaaaggact gaataatttg gctaagttgg gattgagttt caacagcatc    2100
tctgctgttg acaatggctc tctggccaac acgcctcatc tgagggagct tcacttggac    2160
aacaacaagc ttaccagagt acctggtggg ctggcagagc ataagtacat ccaggttgtc    2220
taccttcata caacaatat ctctgtagtt ggatcaagtg acttctgccc acctggacac    2280
aacaccaaaa aggcttctta ttcgggtgtg agtctttca gcaacccggt ccagtactgg    2340
gagatacagc catccacctt cagatgtgtc tacgtgcgct ctgccattca actcggaaac    2400
tataagtga                                                            2409
```

<210> SEQ ID NO 11
<211> LENGTH: 802
<212> TYPE: PRT
<213> ORGANISM: Artificial Sequence
<220> FEATURE:
<223> OTHER INFORMATION: synthetic

<400> SEQUENCE: 11

```
Met Met Ser Phe Val Ser Leu Leu Leu Val Gly Ile Leu Phe His Ala
1               5                   10                  15

Thr Gln Ala Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Thr Met His Trp Val Arg Gln Ala Pro Gly Lys Gly Leu
    50                  55                  60

Glu Trp Val Thr Phe Ile Ser Tyr Asp Gly Asn Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Ile
            100                 105                 110
```

```
Tyr Tyr Cys Ala Arg Thr Gly Trp Leu Gly Pro Phe Asp Tyr Trp Gly
            115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys Ser Gly Gly Gly Gly Ser Asp Glu Ala Ala Gly Ile Gly
465                 470                 475                 480

Pro Glu Val Pro Asp Asp Arg Asp Phe Glu Pro Ser Leu Gly Pro Val
                485                 490                 495

Cys Pro Phe Arg Cys Gln Cys His Leu Arg Val Val Gln Cys Ser Asp
            500                 505                 510

Leu Gly Leu Asp Lys Val Pro Lys Asp Leu Pro Pro Asp Thr Thr Leu
        515                 520                 525

Leu Asp Leu Gln Asn Asn Lys Ile Thr Glu Ile Lys Asp Gly Asp Phe
```

```
        530                 535                 540
Lys Asn Leu Lys Asn Leu His Ala Leu Ile Leu Val Asn Asn Lys Ile
545                 550                 555                 560

Ser Lys Val Ser Pro Gly Ala Phe Thr Pro Leu Val Lys Leu Glu Arg
                565                 570                 575

Leu Tyr Leu Ser Lys Asn Gln Leu Lys Glu Leu Pro Glu Lys Met Pro
            580                 585                 590

Lys Thr Leu Gln Glu Leu Arg Ala His Glu Asn Glu Ile Thr Lys Val
        595                 600                 605

Arg Lys Val Thr Phe Asn Gly Leu Asn Gln Met Ile Val Ile Glu Leu
    610                 615                 620

Gly Thr Asn Pro Leu Lys Ser Ser Gly Ile Glu Asn Gly Ala Phe Gln
625                 630                 635                 640

Gly Met Lys Lys Leu Ser Tyr Ile Arg Ile Ala Asp Thr Asn Ile Thr
                645                 650                 655

Ser Ile Pro Gln Gly Leu Pro Pro Ser Leu Thr Glu Leu His Leu Asp
            660                 665                 670

Gly Asn Lys Ile Ser Arg Val Asp Ala Ala Ser Leu Lys Gly Leu Asn
        675                 680                 685

Asn Leu Ala Lys Leu Gly Leu Ser Phe Asn Ser Ile Ser Ala Val Asp
    690                 695                 700

Asn Gly Ser Leu Ala Asn Thr Pro His Leu Arg Glu Leu His Leu Asp
705                 710                 715                 720

Asn Asn Lys Leu Thr Arg Val Pro Gly Gly Leu Ala Glu His Lys Tyr
                725                 730                 735

Ile Gln Val Val Tyr Leu His Asn Asn Asn Ile Ser Val Val Gly Ser
            740                 745                 750

Ser Asp Phe Cys Pro Pro Gly His Asn Thr Lys Lys Ala Ser Tyr Ser
        755                 760                 765

Gly Val Ser Leu Phe Ser Asn Pro Val Gln Tyr Trp Glu Ile Gln Pro
    770                 775                 780

Ser Thr Phe Arg Cys Val Tyr Val Arg Ser Ala Ile Gln Leu Gly Asn
785                 790                 795                 800

Tyr Lys
```

<210> SEQ ID NO 12
<211> LENGTH: 705
<212> TYPE: DNA
<213> ORGANISM: Artificial Sequence
<220> FEATURE:
<223> OTHER INFORMATION: synthetic

<400> SEQUENCE: 12

```
atgatgtcct ttgtctctct gctcctggtt ggcatcctat tccatgccac ccaggccgag     60
atcgtgctga cccagtcccc cggcaccctg tccctgtccc ccggcgagcg ggccaccctg    120
tcctgccggg cctcccagtc cgtgggctcc tcctacctgg cctggtacca gcagaagccc    180
ggccaggccc ccggctgctg atctacggc gccttctccc gcgccaccgg catccccgac    240
cggttctccg gctccggctc cggcaccgac ttcaccctga ccatctcccg gctggagccc    300
gaggacttcg ccgtgtacta ctgccagcag tacggctcct cccccctgga cttcggccag    360
ggcaccaagg tggagatcaa gcgaactgtg gctgcaccat ctgtcttcat cttcccgcca    420
tctgatgagc agcttaagtc cggaactgct agcgttgtgt gcctgctgaa taacttctat    480
cccagagagg ccaaagtaca gtggaaggtg gataacgccc tccaatcggg taactcccag    540
```

```
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttag                    705
```

<210> SEQ ID NO 13
<211> LENGTH: 234
<212> TYPE: PRT
<213> ORGANISM: Artificial Sequence
<220> FEATURE:
<223> OTHER INFORMATION: synthetic

<400> SEQUENCE: 13

```
Met Met Ser Phe Val Ser Leu Leu Val Gly Ile Leu Phe His Ala
1               5                   10                  15

Thr Gln Ala Glu Ile Val Leu Thr Gln Ser Pro Gly Thr Leu Ser Leu
            20                  25                  30

Ser Pro Gly Glu Arg Ala Thr Leu Ser Cys Arg Ala Ser Gln Ser Val
        35                  40                  45

Gly Ser Ser Tyr Leu Ala Trp Tyr Gln Gln Lys Pro Gly Gln Ala Pro
    50                  55                  60

Arg Leu Leu Ile Tyr Gly Ala Phe Ser Arg Ala Thr Gly Ile Pro Asp
65                  70                  75                  80

Arg Phe Ser Gly Ser Gly Ser Gly Thr Asp Phe Thr Leu Thr Ile Ser
                85                  90                  95

Arg Leu Glu Pro Glu Asp Phe Ala Val Tyr Tyr Cys Gln Gln Tyr Gly
            100                 105                 110

Ser Ser Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 14
<211> LENGTH: 448
<212> TYPE: PRT
<213> ORGANISM: Artificial Sequence
<220> FEATURE:
<223> OTHER INFORMATION: synthetic

<400> SEQUENCE: 14

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
```

```
                35                  40                  45
Thr Phe Ile Ser Tyr Asp Gly Asn Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Arg Thr Gly Trp Leu Gly Pro Phe Asp Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 15
```

<211> LENGTH: 215
<212> TYPE: PRT
<213> ORGANISM: Artificial Sequence
<220> FEATURE:
<223> OTHER INFORMATION: synthetic

<400> SEQUENCE: 15

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 16
<211> LENGTH: 2409
<212> TYPE: DNA
<213> ORGANISM: Artificial Sequence
<220> FEATURE:
<223> OTHER INFORMATION: synthetic

<400> SEQUENCE: 16

| | | | | |
|---|---|---|---|---|
| atgatgtcct | ttgtctctct | gctcctggtt | ggcatcctat | tccatgccac | ccaggccgag | 60 |
| gtacaactcg | tggaatccgg | cggggggactc | gtccaaccgg | gtggtagtct | caggttgagc | 120 |
| tgcgctgcga | gcggtttcac | tttctcagac | tcatggattc | attgggtgcg | ccaagcacct | 180 |
| ggaaaagggt | tggaatgggt | tgcctggatc | tctccttacg | gaggttctac | ctactacgct | 240 |
| gattcagtaa | aggggcggtt | cacaatttca | gccgatactt | ccaaaaatac | ggcttacctg | 300 |
| caaatgaact | ctttgagggc | ggaggatacg | gcggtctact | actgtgcacg | caggcactgg | 360 |
| cctggagggt | tcgattattg | gggtcaaggc | actttggtaa | ccgtatcctc | cgcttctacc | 420 |
| aaaggcccat | cagtatttcc | tttggctccc | agctctaagt | ccacttccgg | tgaactgcc | 480 |
| gcacttggat | gtctcgtcaa | agactacttt | cctgagccgg | taactgtgtc | atggaactcc | 540 |
| ggcgccctca | ctagcggcgt | ccatacattt | ccagcggttc | tccagtcaag | tggcctctac | 600 |

```
agcctgtcca gtgtagttac tgtcccgtct tctagtctgg gaacgcaaac atatatttgc    660
aatgtgaatc ataagcctag taacacaaaa gtcgataaaa aagtggagcc gaaaagttgt    720
gacaaaacgc atacctgtcc gccttgtccg gcccccgaac tcttgggcgg cccatcagtc    780
tttctcttcc cgcccaaacc taaggacacg ttgatgataa gtcgcacgcc cgaggttaca    840
tgcgtcgtag tcgatgtcag ccacgaggat ccggaggtaa agtttaactg gtatgtagac    900
ggagttgaag tacacaacgc caaaactaaa ccgagagagg agcagtacgc atcaacctat    960
cgcgtagtat ctgtattgac ggtccttcac caagactggc tcaatgggaa agaatacaag   1020
tgcaaagttt ctaataaagc cctccctgca ccaatcgaaa agactatttc aaaagccaaa   1080
ggacaaccaa gagaaccaca agtttataca ttgccaccta gtcgcgagga gatgactaaa   1140
aaccaagtgt cccttacttg tctcgtaaag ggtttctatc caagcgacat agcagttgag   1200
tgggaaagta atggccagcc ggaaaacaac tacaagacga ccccccgggt tctcgactcc   1260
gatggatcat tcttttgta tagtaaactc acagttgata agagtcgatg gcagcagggg   1320
aatgtttttt cttgctctgt gatgcacgag gcgctccaca accactatac gcaaaagtcc   1380
ctcagcctga gccccgggaa tccggggggt ggcggatccg atgaggctgc agggataggc   1440
ccagaagttc ctgatgaccg cgacttcgag ccctccctag gcccagtgtg ccccttccgc   1500
tgtcaatgcc atcttcgagt ggtccagtgt tctgatttgg gtctggacaa agtgccaaag   1560
gatcttcccc ctgacacaac tctgctagac ctgcaaaaca acaaaataac cgaaatcaaa   1620
gatggagact taagaacct gaagaacctt cacgcattga ttcttgtcaa caataaaatt   1680
agcaaagtta gtcctggagc atttacacct ttggtgaagt tggaacgact ttatctgtcc   1740
aagaatcagc tgaaggaatt gccagaaaaa atgcccaaaa ctcttcagga gctgcgtgcc   1800
catgagaatg agatcaccaa agtgcgaaaa gttactttca atggactgaa ccagatgatt   1860
gtcatagaac tgggcaccaa tccgctgaag agctcaggaa ttgaaaatgg ggctttccag   1920
ggaatgaaga agctctccta catccgcatt gctgatacca atatcaccag cattcctcaa   1980
ggtcttcctc cttcccttac ggaattacat cttgatggca acaaaatcag cagagttgat   2040
gcagctagcc tgaaaggact gaataatttg gctaagttgg gattgagttt caacagcatc   2100
tctgctgttg acaatggctc tctggccaac acgcctcatc tgagggagct tcacttggac   2160
aacaacaagc ttaccagagt acctggtggg ctggcagagc ataagtacat ccaggttgtc   2220
taccttcata caacaatat ctctgtagtt ggatcaagtg acttctgccc acctggacac   2280
aacaccaaaa aggcttctta ttcgggtgtg agtcttttca gcaacccggt ccagtactgg   2340
gagatacagc catccacctt cagatgtgtc tacgtgcgct ctgccattca actcggaaac   2400
tataagtga                                                           2409
```

<210> SEQ ID NO 17
<211> LENGTH: 802
<212> TYPE: PRT
<213> ORGANISM: Artificial Sequence
<220> FEATURE:
<223> OTHER INFORMATION: synthetic

<400> SEQUENCE: 17

Met Met Ser Phe Val Ser Leu Leu Leu Val Gly Ile Leu Phe His Ala
1               5                   10                  15

Thr Gln Ala Glu Val Gln Leu Val Glu Ser Gly Gly Gly Leu Val Gln
            20                  25                  30

```
Pro Gly Gly Ser Leu Arg Leu Ser Cys Ala Ala Ser Gly Phe Thr Phe
            35                  40                  45

Ser Asp Ser Trp Ile His Trp Val Arg Gln Ala Pro Gly Lys Gly Leu
 50                  55                  60

Glu Trp Val Ala Trp Ile Ser Pro Tyr Gly Ser Thr Tyr Tyr Ala
 65                  70                  75                  80

Asp Ser Val Lys Gly Arg Phe Thr Ile Ser Ala Asp Thr Ser Lys Asn
                 85                  90                  95

Thr Ala Tyr Leu Gln Met Asn Ser Leu Arg Ala Glu Asp Thr Ala Val
            100                 105                 110

Tyr Tyr Cys Ala Arg Arg His Trp Pro Gly Gly Phe Asp Tyr Trp Gly
            115                 120                 125

Gln Gly Thr Leu Val Thr Val Ser Ser Ala Ser Thr Lys Gly Pro Ser
        130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Ala Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
```

| | | | | | | | | | | | |
|---|---|---|---|---|---|---|---|---|---|---|---|
| | | 450 | | | 455 | | | 460 | | | |
| Pro | Gly | Lys | Ser | Gly | Gly | Gly | Ser | Asp | Glu | Ala | Ala | Ile | Gly |
| 465 | | | | 470 | | | | 475 | | | | | 480 |

Pro Gly Lys Ser Gly Gly Gly Ser Asp Glu Ala Ala Ile Gly
465                 470                 475                 480

Pro Glu Val Pro Asp Asp Arg Asp Phe Glu Pro Ser Leu Gly Pro Val
                485                 490                 495

Cys Pro Phe Arg Cys Gln Cys His Leu Arg Val Val Gln Cys Ser Asp
                500                 505                 510

Leu Gly Leu Asp Lys Val Pro Lys Asp Leu Pro Pro Asp Thr Thr Leu
            515                 520                 525

Leu Asp Leu Gln Asn Asn Lys Ile Thr Glu Ile Lys Asp Gly Asp Phe
        530                 535                 540

Lys Asn Leu Lys Asn Leu His Ala Leu Ile Leu Val Asn Asn Lys Ile
545                 550                 555                 560

Ser Lys Val Ser Pro Gly Ala Phe Thr Pro Leu Val Lys Leu Glu Arg
                565                 570                 575

Leu Tyr Leu Ser Lys Asn Gln Leu Lys Glu Leu Pro Glu Lys Met Pro
            580                 585                 590

Lys Thr Leu Gln Glu Leu Arg Ala His Glu Asn Glu Ile Thr Lys Val
            595                 600                 605

Arg Lys Val Thr Phe Asn Gly Leu Asn Gln Met Ile Val Ile Glu Leu
610                 615                 620

Gly Thr Asn Pro Leu Lys Ser Ser Gly Ile Glu Asn Gly Ala Phe Gln
625                 630                 635                 640

Gly Met Lys Lys Leu Ser Tyr Ile Arg Ile Ala Asp Thr Asn Ile Thr
                645                 650                 655

Ser Ile Pro Gln Gly Leu Pro Pro Ser Leu Thr Glu Leu His Leu Asp
            660                 665                 670

Gly Asn Lys Ile Ser Arg Val Asp Ala Ala Ser Leu Lys Gly Leu Asn
            675                 680                 685

Asn Leu Ala Lys Leu Gly Leu Ser Phe Asn Ser Ile Ser Ala Val Asp
690                 695                 700

Asn Gly Ser Leu Ala Asn Thr Pro His Leu Arg Glu Leu His Leu Asp
705                 710                 715                 720

Asn Asn Lys Leu Thr Arg Val Pro Gly Gly Leu Ala Glu His Lys Tyr
                725                 730                 735

Ile Gln Val Val Tyr Leu His Asn Asn Ile Ser Val Val Gly Ser
            740                 745                 750

Ser Asp Phe Cys Pro Pro Gly His Asn Thr Lys Lys Ala Ser Tyr Ser
            755                 760                 765

Gly Val Ser Leu Phe Ser Asn Pro Val Gln Tyr Trp Glu Ile Gln Pro
        770                 775                 780

Ser Thr Phe Arg Cys Val Tyr Val Arg Ser Ala Ile Gln Leu Gly Asn
785                 790                 795                 800

Tyr Lys

<210> SEQ ID NO 18
<211> LENGTH: 702
<212> TYPE: DNA
<213> ORGANISM: Artificial Sequence
<220> FEATURE:
<223> OTHER INFORMATION: synthetic

<400> SEQUENCE: 18
atgatgtcct ttgtctctct gctcctggtt ggcatcctat tccatgccac ccaggccgac    60

| | | |
|---|---|---|
| attcagatga cacaatcacc tagcagtctg agtgcgagcg taggtgatcg cgtaacgatt | 120 |
| acctgcaggg cctctcaaga cgtgtcaacg gcagtggcgt ggtaccagca gaagcctggt | 180 |
| aaagctccta agctcctcat ctattcagct tccttcttgt atagtggagt accgtcaaga | 240 |
| ttttccggaa gcggatcagg tacagatttt actttgacta tcagtagttt gcagccagag | 300 |
| gatttcgcta catattactg tcaacaatat ctctatcacc ctgccacttt tggacaaggg | 360 |
| actaaagtcg aaataaaacg aacagtggcc gcaccaagcg ttttatctt tcccccatcc | 420 |
| gacgagcagt tgaagagcgg caccgcgtcc gtggtctgcc tgttgaataa tttctatcca | 480 |
| agggaggcaa aagtgcaatg gaaagttgat aatgcgcttc aatccggaaa ctcacaagaa | 540 |
| tcagtaacag aacaagactc taaagacagt acatattctc ttagtagcac actcactctt | 600 |
| tcaaaggctg actatgagaa acataaagtg tacgcttgtg aagtgacaca tcaaggtctt | 660 |
| agctccccag taactaagag ctttaatagg ggcgagtgct ga | 702 |

<210> SEQ ID NO 19
<211> LENGTH: 233
<212> TYPE: PRT
<213> ORGANISM: Artificial Sequence
<220> FEATURE:
<223> OTHER INFORMATION: synthetic

<400> SEQUENCE: 19

```
Met Met Ser Phe Val Ser Leu Leu Leu Val Gly Ile Leu Phe His Ala
1               5                   10                  15

Thr Gln Ala Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Val
        35                  40                  45

Ser Thr Ala Val Ala Trp Tyr Gln Gln Lys Pro Gly Lys Ala Pro Lys
    50                  55                  60

Leu Leu Ile Tyr Ser Ala Ser Phe Leu Tyr Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Leu Tyr
            100                 105                 110

His Pro Ala Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 20

<211> LENGTH: 448
<212> TYPE: PRT
<213> ORGANISM: Artificial Sequence
<220> FEATURE:
<223> OTHER INFORMATION: synthetic

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380
```

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 21
<211> LENGTH: 214
<212> TYPE: PRT
<213> ORGANISM: Artificial Sequence
<220> FEATURE:
<223> OTHER INFORMATION: synthetic

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 22
<211> LENGTH: 2415
<212> TYPE: DNA
<213> ORGANISM: Artificial Sequence
<220> FEATURE:
<223> OTHER INFORMATION: synthetic

<400> SEQUENCE: 22
atgatgtcct ttgtctctct gctcctggtt ggcatcctat tccatgccac ccaggccgag      60
gtacagcttt tggagtcagg cggggggctc gtccaacctg ggggtcact ccggttgtca     120

```
tgtgctgcca gtggcttcac attctcatct tacattatga gtgggttcg acaggcccct    180
gggaagggc tggagtgggt ttcctccatc taccctccg ggaattac cttctatgcc      240
gacacggtaa agggtcgctt cactataagt cgagataaca gcaaaaatac gctgtatctc   300
cagatgaact ctctcagggc tgaggacaca gctgtatatt actgcgcgcg gattaagttg   360
gggaccgtca caacagtgga ttactgggt caaggcactc tggtaaccgt atcctcagca    420
tccaccaagg gcccaagtgt attcccgctg gccccttcaa gtaaatccac gtctggcggc   480
acagccgctc tcggttgcct ggttaaggac tacttcccag aacctgtcac tgtcagttgg   540
aactcaggcg cattgacatc tggtgtccat acattcccg cagtcctgca aagctctgga    600
ctttacagtc ttagtagcgt agtgacagtc ccatcttcaa gtcttgggac ccaaacttat   660
atttgcaacg taaatcataa accctccaac actaaagtag acaaaaagt agagccgaaa    720
tcttgcgaca aaacgcatac atgcccacca tgtcccgctc cggaactcct gggcggcccg   780
tccgttttc tctttccccc aaagcccaag gatacgctta tgatcagcag aacaccggaa    840
gttacttgtg tagtcgttga cgtgtctcac gaagatcccg aagtcaaatt taattggtat   900
gtggatggcg tcgaagtgca caacgcaaaa accaaaccca gagaggaaca gtataacagc   960
acgtatcgag tggtctccgt acttacggtc ctccaccagg actggttgaa tggcaaggag   1020
tacaagtgca aagtgagcaa taaagcgttg ccagccccga tcgaaaaaac catcagcaag   1080
gccaagggac agcctagaga gccgcaggtt tacaccttgc cgccatcaag ggatgaactg   1140
actaaaaacc aggtatccct gacctgcctg gttaagggtt tttaccccag tgatatagcg   1200
gttgaatggg agtctaacgg gcagccagag aacaactaca aaacgacacc tcccgttctg   1260
gattccgatg gcagctttt cttgtattct aaactcaccg tggataaatc ccgatggcag   1320
caaggcaacg tcttctcctg cagcgtgatg catgaagcct tgcacaacca ctatacccaa   1380
aagagtctca gcctgtcacc cgggaaatcc gggggtggcg gatccgatga ggctgcaggg   1440
ataggcccag aagttcctga tgaccgcgac ttcgagccct ccctaggccc agtgtgcccc   1500
ttccgctgtc aatgccatct tcgagtggtc cagtgttctg atttgggtct ggacaaagtg   1560
ccaaaggatc ttcccctga cacaactctg ctagacctgc aaaacaacaa ataaccgaa    1620
atcaaagatg gagactttaa gaacctgaag aaccttcacg cattgattct tgtcaacaat   1680
aaaattagca agttagtcc tggagcattt acacctttgg tgaagttgga acgactttat   1740
ctgtccaaga atcagctgaa ggaattgcca gaaaaaatgc ccaaaactct tcaggagctg   1800
cgtgcccatg agaatgagat caccaaagtg cgaaaagtta ctttcaatgg actgaaccag   1860
atgattgtca tagaactggg caccaatccg ctgaagagct caggaattga aaatggggct   1920
ttccagggaa tgaagaagct ctcctacatc cgcattgctg ataccaatat caccagcatt   1980
cctcaaggtc ttcctccttc ccttacggaa ttacatcttg atggcaacaa aatcagcaga   2040
gttgatgcag ctagcctgaa aggactgaat aatttggcta agttgggatt gagtttcaac   2100
agcatctctg ctgttgacaa tggctctctg gccaacacgc tcatctgag ggagcttcac    2160
ttggacaaca acaagcttac cagagtacct ggtgggctgg cagagcataa gtacatccag   2220
gttgtctacc ttcataacaa caatatctct gtagttggat caagtgactt ctgcccacct   2280
ggacacaaca ccaaaaaggc ttcttattcg ggtgtgagtc ttttcagcaa cccggtccag   2340
tactgggaga tacagccatc caccttcaga tgtgtctacg tgcgctctgc cattcaactc   2400
ggaaactata agtga                                                    2415
```

-continued

```
<210> SEQ ID NO 23
<211> LENGTH: 804
<212> TYPE: PRT
<213> ORGANISM: Artificial Sequence
<220> FEATURE:
<223> OTHER INFORMATION: synthetic

<400> SEQUENCE: 23

Met Met Ser Phe Val Ser Leu Leu Val Gly Ile Leu Phe His Ala
1               5                   10                  15

Thr Gln Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ile Met Met Trp Val Arg Gln Ala Pro Gly Lys Gly Leu
    50                  55                  60

Glu Trp Val Ser Ser Ile Tyr Pro Ser Gly Gly Ile Thr Phe Tyr Ala
65                  70                  75                  80

Asp Thr Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ile Lys Leu Gly Thr Val Thr Val Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
```

```
            370                 375                 380
Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
        450                 455                 460

Leu Ser Pro Gly Lys Ser Gly Gly Gly Ser Asp Glu Ala Ala Gly
465                 470                 475                 480

Ile Gly Pro Glu Val Pro Asp Asp Arg Asp Phe Glu Pro Ser Leu Gly
                485                 490                 495

Pro Val Cys Pro Phe Arg Cys Gln Cys His Leu Arg Val Val Gln Cys
                500                 505                 510

Ser Asp Leu Gly Leu Asp Lys Val Pro Lys Asp Leu Pro Pro Asp Thr
        515                 520                 525

Thr Leu Leu Asp Leu Gln Asn Asn Lys Ile Thr Glu Ile Lys Asp Gly
        530                 535                 540

Asp Phe Lys Asn Leu Lys Asn Leu His Ala Leu Ile Leu Val Asn Asn
545                 550                 555                 560

Lys Ile Ser Lys Val Ser Pro Gly Ala Phe Thr Pro Leu Val Lys Leu
                565                 570                 575

Glu Arg Leu Tyr Leu Ser Lys Asn Gln Leu Lys Glu Leu Pro Glu Lys
                580                 585                 590

Met Pro Lys Thr Leu Gln Glu Leu Arg Ala His Glu Asn Glu Ile Thr
                595                 600                 605

Lys Val Arg Lys Val Thr Phe Asn Gly Leu Asn Gln Met Ile Val Ile
        610                 615                 620

Glu Leu Gly Thr Asn Pro Leu Lys Ser Ser Gly Ile Glu Asn Gly Ala
625                 630                 635                 640

Phe Gln Gly Met Lys Lys Leu Ser Tyr Ile Arg Ile Ala Asp Thr Asn
                645                 650                 655

Ile Thr Ser Ile Pro Gln Gly Leu Pro Pro Ser Leu Thr Glu Leu His
                660                 665                 670

Leu Asp Gly Asn Lys Ile Ser Arg Val Asp Ala Ala Ser Leu Lys Gly
                675                 680                 685

Leu Asn Asn Leu Ala Lys Leu Gly Leu Ser Phe Asn Ser Ile Ser Ala
        690                 695                 700

Val Asp Asn Gly Ser Leu Ala Asn Thr Pro His Leu Arg Glu Leu His
705                 710                 715                 720

Leu Asp Asn Asn Lys Leu Thr Arg Val Pro Gly Gly Leu Ala Glu His
                725                 730                 735

Lys Tyr Ile Gln Val Val Tyr Leu His Asn Asn Ile Ser Val Val
        740                 745                 750

Gly Ser Ser Asp Phe Cys Pro Pro Gly His Asn Thr Lys Lys Ala Ser
        755                 760                 765

Tyr Ser Gly Val Ser Leu Phe Ser Asn Pro Val Gln Tyr Trp Glu Ile
        770                 775                 780

Gln Pro Ser Thr Phe Arg Cys Val Tyr Val Arg Ser Ala Ile Gln Leu
785                 790                 795                 800
```

Gly Asn Tyr Lys

<210> SEQ ID NO 24
<211> LENGTH: 708
<212> TYPE: DNA
<213> ORGANISM: Artificial Sequence
<220> FEATURE:
<223> OTHER INFORMATION: synthetic

<400> SEQUENCE: 24

```
atgatgtcct ttgtctctct gctcctggtt ggcatcctat tccatgccac ccaggcccag    60
tctgcactta cacaaccggc gtccgtttcc ggatctccag gacagagcat tactatcagt   120
tgcacgggaa cctcctcaga cgtagggggg tataattatg tgtcttggta tcaacagcat   180
cccgggaaag cccccaaact gatgatctac gatgtcagca atagaccaag cggtgtgagt   240
aatcgattta gcgggtctaa atctggtaac acagcatccc tcactattag tggactgcaa   300
gcagaagatg aggcagacta ttattgcagt agctatacgt ctagttccac ccgcgttttt   360
ggcactggga cgaaagtcac cgttctcgga caaccaaaag caaacccac cgtgactctg    420
tttccgccta gcagcgaaga attgcaggcc aataaggcga cactcgtatg ccttatctcc   480
gacttctacc cgggcgctgt gacagtcgcg tggaaagccg acggcagccc tgttaaagct   540
ggagtcgaga ccacgaagcc gtccaagcag agtaacaata gtatgctgc atccagttat    600
ctctctctca ctccggaaca gtggaagtcc catcggtcct atagttgcca agtgacccat   660
gagggttcca ccgtagagaa aacggtagca cctaccgaat gtagttga              708
```

<210> SEQ ID NO 25
<211> LENGTH: 235
<212> TYPE: PRT
<213> ORGANISM: Artificial Sequence
<220> FEATURE:
<223> OTHER INFORMATION: synthetic

<400> SEQUENCE: 25

Met Met Ser Phe Val Ser Leu Leu Val Gly Ile Leu Phe His Ala
1               5                   10                  15

Thr Gln Ala Gln Ser Ala Leu Thr Gln Pro Ala Ser Val Ser Gly Ser
                20                  25                  30

Pro Gly Gln Ser Ile Thr Ile Ser Cys Thr Gly Thr Ser Ser Asp Val
            35                  40                  45

Gly Gly Tyr Asn Tyr Val Ser Trp Tyr Gln Gln His Pro Gly Lys Ala
        50                  55                  60

Pro Lys Leu Met Ile Tyr Asp Val Ser Asn Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Ser Ser Tyr
            100                 105                 110

Thr Ser Ser Ser Thr Arg Val Phe Gly Thr Gly Thr Lys Val Thr Val
        115                 120                 125

Leu Gly Gln Pro Lys Ala Asn Pro Thr Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Gly Ser
                165                 170                 175

```
Pro Val Lys Ala Gly Val Glu Thr Thr Lys Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 26
<211> LENGTH: 450
<212> TYPE: PRT
<213> ORGANISM: Artificial Sequence
<220> FEATURE:
<223> OTHER INFORMATION: synthetic

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 27
<211> LENGTH: 216
<212> TYPE: PRT
<213> ORGANISM: Artificial Sequence
<220> FEATURE:
<223> OTHER INFORMATION: synthetic

<400> SEQUENCE: 27

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205
```

Thr Val Ala Pro Thr Glu Cys Ser
    210             215

<210> SEQ ID NO 28
<211> LENGTH: 2418
<212> TYPE: DNA
<213> ORGANISM: Artificial Sequence
<220> FEATURE:
<223> OTHER INFORMATION: synthetic

<400> SEQUENCE: 28

| | | | | | |
|---|---|---|---|---|---|
| atgatgtcct | ttgtctctct | gctcctggtt | ggcatcctat | tccatgccac | ccaggccgag | 60 |
| gtccagcttg | ttgaaagcgg | tggtggcctc | gtgcagcctg | gtggcagttt | gcggttgtct | 120 |
| tgcgcagcta | gtggttttac | cttctccaga | tactggatgt | catgggtccg | acaggcccct | 180 |
| ggcaagggc | ttgaatgggt | tgcaaatata | aagcaggacg | gttctgaaaa | gtactatgta | 240 |
| gactccgtca | aggaagatt | tactattagt | cgagacaacg | ccaagaatag | cctctacctt | 300 |
| cagatgaatt | ctttgcgagc | ggaggacaca | gccgtatatt | actgcgcacg | agaaggggg | 360 |
| tggttcggtg | aactggcttt | tgactactgg | ggcaaggta | cgcttgtcac | ggtgagctct | 420 |
| gcctctacaa | aggggccgtc | tgtgtttcca | cttgctccat | ctagtaagtc | aacttctgga | 480 |
| ggtactgcgg | cattgggatg | ccttgttaag | gattattttc | ccgaacctgt | aactgtgagc | 540 |
| tggaattcag | gtgccctcac | ctctggtgta | catacctttc | cagcagtttt | gcaatcttcc | 600 |
| ggtttgtact | ctcttagttc | agttgtaact | gtcccctctt | cctctcttgg | tacccaaaca | 660 |
| tacatttgta | atgtcaatca | caaaccaagc | aataccaagg | tagacaagcg | ggtggaaccc | 720 |
| aaatcttgtg | acaaaactca | tacctgccca | ccatgtcccg | ccccggagtt | tgaaggaggt | 780 |
| ccaagtgtat | ttctttccc | gcctaagcct | aaggatacc | tcatgataag | tcggacacca | 840 |
| gaggtgacgt | gtgttgtggt | agacgtgagt | cacgaagatc | ccgaagttaa | atttaattgg | 900 |
| tatgtggacg | gggtggaagt | ccataacgcg | aagacaaagc | cacgcgaaga | gcagtacaat | 960 |
| tccacgtaca | gggtggttag | cgtgcttacc | gtcctgcatc | aagattggct | gaacgggaaa | 1020 |
| gaatacaaat | gcaaagtatc | caacaaggcg | ttgcctgcga | gtatcgagaa | aacgatttct | 1080 |
| aaagctaaag | acaaccccg | ggaaccccag | gtctatacac | tgccgcccag | cagagaagag | 1140 |
| atgacgaaaa | atcaagtatc | ccttacgtgt | ctcgtcaaag | gcttctaccc | ttccgatatt | 1200 |
| gctgtagagt | gggaatctaa | cgggcagccg | gaaaataact | acaagactac | tccgccagta | 1260 |
| cttgattcag | acggctcctt | cttcctttat | tcaaaactca | ccgtagataa | agtaggtgg | 1320 |
| caacaaggta | atgttttag | ctgtagcgta | atgcacgaag | cgttgcataa | ccattataca | 1380 |
| cagaaatcac | tcagcctgtc | ccccgggaaa | tccggggtg | gcggatccga | tgaggctgca | 1440 |
| gggataggcc | agaagttcc | tgatgaccgc | gacttcgagc | cctccctagg | cccagtgtgc | 1500 |
| ccccttccgct | gtcaatgcca | tcttcgagtg | gtccagtgtt | ctgatttggg | tctggacaaa | 1560 |
| gtgccaaagg | atcttccccc | tgacacaact | ctgctagacc | tgcaaaacaa | caaaataacc | 1620 |
| gaaatcaaag | atggagactt | taagaacctg | aagaacctc | acgcattgat | tcttgtcaac | 1680 |
| aataaaatta | gcaagttag | tcctggagca | tttacacctt | tggtgaagtt | ggaacgactt | 1740 |
| tatctgtcca | gaatcagct | gaaggaattg | ccagaaaaaa | tgcccaaaac | tcttcaggag | 1800 |
| ctgcgtgccc | atgagaatga | gatcaccaaa | gtgcgaaaag | ttactttcaa | tggactgaac | 1860 |
| cagatgattg | tcatagaact | gggcaccaat | ccgctgaaga | gctcaggaat | tgaaaatggg | 1920 |
| gcttccagg | gaatgaagaa | gctctcctac | atccgcattg | ctgataccaa | tatcaccagc | 1980 |

```
attcctcaag gtcttcctcc ttcccttacg gaattacatc ttgatggcaa caaaatcagc    2040
agagttgatg cagctagcct gaaaggactg aataatttgg ctaagttggg attgagtttc    2100
aacagcatct ctgctgttga caatggctct ctggccaaca cgcctcatct gagggagctt    2160
cacttggaca caacaagct  taccagagta cctggtgggc tggcagagca taagtacatc    2220
caggttgtct accttcataa caacaatatc tctgtagttg gatcaagtga cttctgccca    2280
cctggacaca acaccaaaaa ggcttcttat tcgggtgtga gtcttttcag caacccggtc    2340
cagtactggg agatacagcc atccaccttc agatgtgtct acgtgcgctc tgccattcaa    2400
ctcggaaact ataagtga                                                  2418
```

<210> SEQ ID NO 29
<211> LENGTH: 805
<212> TYPE: PRT
<213> ORGANISM: Artificial Sequence
<220> FEATURE:
<223> OTHER INFORMATION: synthetic

<400> SEQUENCE: 29

```
Met Met Ser Phe Val Ser Leu Leu Val Gly Ile Leu Phe His Ala
1               5                   10                  15

Thr Gln Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Arg Tyr Trp Met Ser Trp Val Arg Gln Ala Pro Gly Lys Gly Leu
    50                  55                  60

Glu Trp Val Ala Asn Ile Lys Gln Asp Gly Ser Glu Lys Tyr Tyr Val
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Glu Gly Gly Trp Phe Gly Glu Leu Ala Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Phe Glu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
```

```
            275                 280                 285
Val Ser His Glu Asp Pro Glu Val Lys Phe Asn Trp Tyr Val Asp Gly
        290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
            340                 345                 350
Ala Ser Ile Glu Lys Thr Ile Ser Lys Ala Lys Gly Gln Pro Arg Glu
        355                 360                 365
Pro Gln Val Tyr Thr Leu Pro Pro Ser Arg Glu Glu Met Thr Lys Asn
370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
        435                 440                 445
Ser Val Met His Glu Ala Leu His Asn His Tyr Thr Gln Lys Ser Leu
450                 455                 460
Ser Leu Ser Pro Gly Lys Ser Gly Gly Gly Ser Asp Glu Ala Ala
465                 470                 475                 480
Gly Ile Gly Pro Glu Val Pro Asp Asp Arg Asp Phe Glu Pro Ser Leu
                485                 490                 495
Gly Pro Val Cys Pro Phe Arg Cys Gln Cys His Leu Arg Val Val Gln
            500                 505                 510
Cys Ser Asp Leu Gly Leu Asp Lys Val Pro Lys Asp Leu Pro Pro Asp
        515                 520                 525
Thr Thr Leu Leu Asp Leu Gln Asn Asn Lys Ile Thr Glu Ile Lys Asp
530                 535                 540
Gly Asp Phe Lys Asn Leu Lys Asn Leu His Ala Leu Ile Leu Val Asn
545                 550                 555                 560
Asn Lys Ile Ser Lys Val Ser Pro Gly Ala Phe Thr Pro Leu Val Lys
                565                 570                 575
Leu Glu Arg Leu Tyr Leu Ser Lys Asn Gln Leu Lys Glu Leu Pro Glu
            580                 585                 590
Lys Met Pro Lys Thr Leu Gln Glu Leu Arg Ala His Glu Asn Glu Ile
        595                 600                 605
Thr Lys Val Arg Lys Val Thr Phe Asn Gly Leu Asn Gln Met Ile Val
610                 615                 620
Ile Glu Leu Gly Thr Asn Pro Leu Lys Ser Ser Gly Ile Glu Asn Gly
625                 630                 635                 640
Ala Phe Gln Gly Met Lys Lys Leu Ser Tyr Ile Arg Ile Ala Asp Thr
                645                 650                 655
Asn Ile Thr Ser Ile Pro Gln Gly Leu Pro Pro Ser Leu Thr Glu Leu
            660                 665                 670
His Leu Asp Gly Asn Lys Ile Ser Arg Val Asp Ala Ala Ser Leu Lys
        675                 680                 685
Gly Leu Asn Asn Leu Ala Lys Leu Gly Leu Ser Phe Asn Ser Ile Ser
690                 695                 700
```

Ala Val Asp Asn Gly Ser Leu Ala Asn Thr Pro His Leu Arg Glu Leu
705                 710                 715                 720

His Leu Asp Asn Asn Lys Leu Thr Arg Val Pro Gly Gly Leu Ala Glu
            725                 730                 735

His Lys Tyr Ile Gln Val Val Tyr Leu His Asn Asn Ile Ser Val
        740                 745                 750

Val Gly Ser Ser Asp Phe Cys Pro Pro Gly His Asn Thr Lys Lys Ala
            755                 760                 765

Ser Tyr Ser Gly Val Ser Leu Phe Ser Asn Pro Val Gln Tyr Trp Glu
        770                 775                 780

Ile Gln Pro Ser Thr Phe Arg Cys Val Tyr Val Arg Ser Ala Ile Gln
785                 790                 795                 800

Leu Gly Asn Tyr Lys
            805

<210> SEQ ID NO 30
<211> LENGTH: 705
<212> TYPE: DNA
<213> ORGANISM: Artificial Sequence
<220> FEATURE:
<223> OTHER INFORMATION: synthetic

<400> SEQUENCE: 30
atgatgtcct tgtctctct gctcctggtt ggcatcctat tccatgccac ccaggccgag      60
atagttttga ctcaaagccc tggaacgctc tctttgtctc ccggcgagcg ggcgacccct     120
tcctgtaggg ctagccagag ggtatcttcc tcttacctgg catggtacca gcaaaagccc     180
ggacaagccc cccgacttct gatttatgac gcctcatccc gggcgacagg catccctgac     240
cgattttcag ggagtggctc tggtaccgat tttacgctta cgatttccag gctggagccc     300
gaggatttcg cagtgtatta ctgtcaacaa tacggcagct gccctggac cttggacaa     360 ggaaccaagg tagagatcaa aggaccgtt gccgccccgt ccgtgttcat cttccctccg     420
agcgatgagc aacttaaaag tggaactgca agcgttgtat gtcttctgaa caatttctat     480
ccccgagaag ccaaggtaca gtggaaagtg ataatgccc tccaatctgg caatagccaa     540
gagtctgtca cagagcagga cagcaaggac tcaacttatt cacttagctc caccctgacg     600
ctgagtaaag cagactacga gaagcataag gtgtatgctt gtgaggttac acaccaaggc     660
ttgtcttctc ctgtcacgaa gtctttcaat aggggcgaat gctga              705

<210> SEQ ID NO 31
<211> LENGTH: 234
<212> TYPE: PRT
<213> ORGANISM: Artificial Sequence
<220> FEATURE:
<223> OTHER INFORMATION: synthetic

<400> SEQUENCE: 31

Met Met Ser Phe Val Ser Leu Leu Leu Val Gly Ile Leu Phe His Ala
1               5                   10                  15

Thr Gln Ala Glu Ile Val Leu Thr Gln Ser Pro Gly Thr Leu Ser Leu
            20                  25                  30

Ser Pro Gly Glu Arg Ala Thr Leu Ser Cys Arg Ala Ser Gln Arg Val
        35                  40                  45

Ser Ser Ser Tyr Leu Ala Trp Tyr Gln Gln Lys Pro Gly Gln Ala Pro
    50                  55                  60

Arg Leu Leu Ile Tyr Asp Ala Ser Ser Arg Ala Thr Gly Ile Pro Asp

```
                65                  70                  75                  80
Arg Phe Ser Gly Ser Gly Ser Gly Thr Asp Phe Thr Leu Thr Ile Ser
                    85                  90                  95

Arg Leu Glu Pro Glu Asp Phe Ala Val Tyr Tyr Cys Gln Gln Tyr Gly
                100                 105                 110

Ser Leu Pro Trp Thr Phe Gly Gln Gly Thr Lys Val Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 32
<211> LENGTH: 451
<212> TYPE: PRT
<213> ORGANISM: Artificial Sequence
<220> FEATURE:
<223> OTHER INFORMATION: synthetic

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
```

```
            195                 200                 205
Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 33
<211> LENGTH: 215
<212> TYPE: PRT
<213> ORGANISM: Artificial Sequence
<220> FEATURE:
<223> OTHER INFORMATION: synthetic

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
```

```
              100                 105                 110
Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 34
<211> LENGTH: 2385
<212> TYPE: DNA
<213> ORGANISM: Artificial Sequence
<220> FEATURE:
<223> OTHER INFORMATION: synthetic

<400> SEQUENCE: 34
atgatgtcct tgtctctctc gctcctggtt ggcatcctat tccatgccac ccaggcccaa      60
gtccagctcg tggaatcagg aggggtgta gtccaaccag gcggagcct ccgacttgat       120 tgtaaagcat caggaattac attttctaat agcggaatgc attgggtccg acaagcgcca     180
ggcaagggac tggaatgggt cgcggtgata tggtatgatg atcaaaacg ctattatgcg      240 gactctgtga agggtcgatt cactattagc agagataaca gcaagaatac tctcttcctt    300
cagatgaatt cacttagggc agaggacaca gcggtgtact attgcgcgac gaacgacgat    360
tattggggcc aagggacatt ggtaacggtg agttctgcta gtactaaagg gccttccgtc    420
ttcccactcg cccttgttc tagaagtact agtgagtcaa cagctgcttt gggttgcttg    480
gttaaagact actttcctga cccgtgact gtgtcttgga attccggtgc tcttacttca     540
ggtgttcata cattcccagc agtattgcag agctctggct tgtattctct ctcctcagtg    600
gtgacagtac cttcctcctc tcttggcaca aaaacttaca catgtaatgt agaccataaa    660
ccatcaaaca cgaaagttga caagagagta gaaagcaagt atgggcctcc atgtccccg     720 tgcccggcgc ccgagttcct gggtggtccg tcagtgttct tgttccctcc caagccaaaa   780
gatacattga tgataagtcg gacgccggag gtcacatgtg tagtagttga tgtctctcag    840
gaggatcctg aggtgcagtt taactggtac gtcgatggtg ttgaggtaca caacgccaaa    900
actaagccga gggaagagca gttcaattca acatatcggg tcgtgtccgt attgacagtt    960
ctgcaccaag attggttgaa cggaaaagag tataagtgca aagttagcaa taagggactt   1020
ccgtcctcaa ttgaaaaaac catttccaaa gcgaaggcc aacctcggga acctcaggta    1080
tataccttgc cacccagcca agaagaaatg actaaaaacc aggttagttt gacatgtttg   1140
gttaaaggct tttacccgtc cgacattgcc gtcgagtggg aaagcaatgg cagcctgaa    1200 aataactaca agacaacccc accagtattg gattccgacg gttccttctt tctttacagc   1260
cgcctcaccg tcgataagag tcggtggcaa gaggggaatg tcttttcctg tagtgtcatg   1320
cacgaagcac ttcacaacca ttacacccaa aaatcattgt ccctgtcact ggggaaatcc   1380
```

```
ggggggtggcg atccgatga ggctgcaggg ataggcccag aagttcctga tgaccgcgac    1440
ttcgagccct ccctaggccc agtgtgcccc ttccgctgtc aatgccatct tcgagtggtc    1500
cagtgttctg atttgggtct ggacaaagtg ccaaggatc ttcccctga cacaactctg      1560 ctagacctgc aaaacaacaa aataaccgaa atcaaagatg agactttaa gaacctgaag     1620 aaccttcacg cattgattct tgtcaacaat aaaattagca aagttagtcc tggagcattt    1680
acacctttgg tgaagttgga acgactttat ctgtccaaga atcagctgaa ggaattgcca    1740
gaaaaaatgc ccaaaactct tcaggagctg cgtgcccatg agaatgagat caccaaagtg    1800
cgaaaagtta ctttcaatgg actgaaccag atgattgtca tagaactggg caccaatccg    1860
ctgaagagct caggaattga aaatggggct ttccagggaa tgaagaagct ctcctacatc    1920
cgcattgctg ataccaatat caccagcatt cctcaaggtc ttcctccttc ccttacggaa    1980
ttacatcttg atggcaacaa aatcagcaga gttgatgcag ctagcctgaa aggactgaat    2040
aatttggcta agtgggatt gagtttcaac agcatctctg ctgttgacaa tggctctctg    2100
gccaacacgc ctcatctgag ggagcttcac ttggacaaca acaagcttac cagagtacct    2160
ggtgggctgg cagagcataa gtacatccga gttgtctacc ttcataacaa caatatctct    2220
gtagttggat caagtgactt ctgcccacct ggacacaaca ccaaaaaggc ttcttattcg    2280
ggtgtgagtc ttttcagcaa cccggtccag tactgggaga tacagccatc caccttcaga    2340
tgtgtctacg tgcgctctgc cattcaactc ggaaactata agtga                   2385
```

<210> SEQ ID NO 35
<211> LENGTH: 794
<212> TYPE: PRT
<213> ORGANISM: Artificial Sequence
<220> FEATURE:
<223> OTHER INFORMATION: synthetic

<400> SEQUENCE: 35

```
Met Met Ser Phe Val Ser Leu Leu Val Gly Ile Leu Phe His Ala
1               5                   10                  15

Thr Gln Ala Gln Val Gln Leu Val Glu Ser Gly Gly Gly Val Val Gln
                20                  25                  30

Pro Gly Arg Ser Leu Arg Leu Asp Cys Lys Ala Ser Gly Ile Thr Phe
            35                  40                  45

Ser Asn Ser Gly Met His Trp Val Arg Gln Ala Pro Gly Lys Gly Leu
        50                  55                  60

Glu Trp Val Ala Val Ile Trp Tyr Asp Gly Ser Lys Arg Tyr Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Val
            100                 105                 110

Tyr Tyr Cys Ala Thr Asn Asp Asp Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190
```

```
Gly Leu Tyr Ser Leu Ser Ser Val Thr Val Pro Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
                260                 265                 270

Cys Val Val Val Asp Val Ser Gln Glu Asp Pro Glu Val Gln Phe Asn
                275                 280                 285

Trp Tyr Val Asp Gly Val Glu Val His Asn Ala Lys Thr Lys Pro Arg
                290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
                340                 345                 350

Gly Gln Pro Arg Glu Pro Gln Val Tyr Thr Leu Pro Pro Ser Gln Glu
                355                 360                 365

Glu Met Thr Lys Asn Gln Val Ser Leu Thr Cys Leu Val Lys Gly Phe
                370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
                420                 425                 430

Asn Val Phe Ser Cys Ser Val Met His Glu Ala Leu His Asn His Tyr
                435                 440                 445

Thr Gln Lys Ser Leu Ser Leu Ser Leu Gly Lys Ser Gly Gly Gly Gly
                450                 455                 460

Ser Asp Glu Ala Ala Gly Ile Gly Pro Glu Val Pro Asp Asp Arg Asp
465                 470                 475                 480

Phe Glu Pro Ser Leu Gly Pro Val Cys Pro Phe Arg Cys Gln Cys His
                485                 490                 495

Leu Arg Val Val Gln Cys Ser Asp Leu Gly Leu Asp Lys Val Pro Lys
                500                 505                 510

Asp Leu Pro Pro Asp Thr Thr Leu Leu Asp Leu Gln Asn Asn Lys Ile
                515                 520                 525

Thr Glu Ile Lys Asp Gly Asp Phe Lys Asn Leu Lys Asn Leu His Ala
530                 535                 540

Leu Ile Leu Val Asn Asn Lys Ile Ser Lys Val Ser Pro Gly Ala Phe
545                 550                 555                 560

Thr Pro Leu Val Lys Leu Glu Arg Leu Tyr Leu Ser Lys Asn Gln Leu
                565                 570                 575

Lys Glu Leu Pro Glu Lys Met Pro Lys Thr Leu Gln Glu Leu Arg Ala
                580                 585                 590

His Glu Asn Glu Ile Thr Lys Val Arg Lys Val Thr Phe Asn Gly Leu
                595                 600                 605
```

Asn Gln Met Ile Val Ile Glu Leu Gly Thr Asn Pro Leu Lys Ser Ser
    610                 615                 620

Gly Ile Glu Asn Gly Ala Phe Gln Gly Met Lys Lys Leu Ser Tyr Ile
625                 630                 635                 640

Arg Ile Ala Asp Thr Asn Ile Thr Ser Ile Pro Gln Gly Leu Pro Pro
                645                 650                 655

Ser Leu Thr Glu Leu His Leu Asp Gly Asn Lys Ile Ser Arg Val Asp
            660                 665                 670

Ala Ala Ser Leu Lys Gly Leu Asn Asn Leu Ala Lys Leu Gly Leu Ser
        675                 680                 685

Phe Asn Ser Ile Ser Ala Val Asp Asn Gly Ser Leu Ala Asn Thr Pro
690                 695                 700

His Leu Arg Glu Leu His Leu Asp Asn Asn Lys Leu Thr Arg Val Pro
705                 710                 715                 720

Gly Gly Leu Ala Glu His Lys Tyr Ile Gln Val Val Tyr Leu His Asn
                725                 730                 735

Asn Asn Ile Ser Val Val Gly Ser Ser Asp Phe Cys Pro Pro Gly His
            740                 745                 750

Asn Thr Lys Lys Ala Ser Tyr Ser Gly Val Ser Leu Phe Ser Asn Pro
        755                 760                 765

Val Gln Tyr Trp Glu Ile Gln Pro Ser Thr Phe Arg Cys Val Tyr Val
770                 775                 780

Arg Ser Ala Ile Gln Leu Gly Asn Tyr Lys
785                 790

<210> SEQ ID NO 36
<211> LENGTH: 702
<212> TYPE: DNA
<213> ORGANISM: Artificial Sequence
<220> FEATURE:
<223> OTHER INFORMATION: synthetic

<400> SEQUENCE: 36
atgatgtcct tgtctctct gctcctggtt ggcatcctat tccatgccac ccaggccgaa     60
atcgtattga ctcagtcccc tgctacactt tcactgagtc cgggtgagcg ggcgactttg    120
tcatgtcggg catcacagag tgtaagtagt tatctggcct ggtatcaaca gaaaccggga    180
caggctcctc gcctgctgat ttatgacgca agcaatcgcg cgaccggcat cccggcgagg    240
ttctcagggt ctggatcagg tactgacttt acccttacga tctcttctct cgaacctgag    300
gatttcgctg tctattactg ccagcagtct tctaactggc cgagaacatt tggtcaaggg    360
acaaaagtcg agattaagcg aactgtcgca gcgccatctg tctttatctt ccctccaagc    420
gacgaacagc ttaagagtgg caccgccagt gttgtctgcc ttctgaataa cttctatcca    480
agggaagcga agttcagtg gaaggtggat aacgctctgc agtctgggaa ctctcaggaa    540
agtgtaacag aacaagactc caaagactca acctactctc ttagttccac gttgaccctc    600
tccaaagcgg actatgagaa gcataaggtc tacgcttgcg aggtaacaca ccaggggctg    660
agtagtccgg ttacgaagag cttcaacaga ggaatgct ga                       702

<210> SEQ ID NO 37
<211> LENGTH: 233
<212> TYPE: PRT
<213> ORGANISM: Artificial Sequence
<220> FEATURE:
<223> OTHER INFORMATION: synthetic

<400> SEQUENCE: 37

Met Met Ser Phe Val Ser Leu Leu Val Gly Ile Leu Phe His Ala
1               5                   10                  15

Thr Gln Ala Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Ser Ser Tyr Leu Ala Trp Tyr Gln Gln Lys Pro Gly Gln Ala Pro Arg
50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Ser Ser Asn
            100                 105                 110

Trp Pro Arg Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 38
<211> LENGTH: 440
<212> TYPE: PRT
<213> ORGANISM: Artificial Sequence
<220> FEATURE:
<223> OTHER INFORMATION: synthetic

<400> SEQUENCE: 38

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

```
Arg Ser Thr Ser Glu Ser Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 39
<211> LENGTH: 214
<212> TYPE: PRT
<213> ORGANISM: Artificial Sequence
<220> FEATURE:
<223> OTHER INFORMATION: synthetic

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45
```

```
Tyr Asp Ala Ser Asn Arg Ala Thr Gly Ile Pro Ala Arg Phe Ser Gly
 50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Ser Ser Asn Trp Pro Arg
                 85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 40
<211> LENGTH: 2406
<212> TYPE: DNA
<213> ORGANISM: Artificial Sequence
<220> FEATURE:
<223> OTHER INFORMATION: synthetic

<400> SEQUENCE: 40
atgatgtcct tgtctctct gctcctggtt ggcatcctat tccatgccac ccaggcccag     60
gtgcaattgg tccaaagtgg ggtcgaggtc aagaagccag gagcttctgt aaaagtttca   120
tgtaaggcat ctgggtatac cttcacgaac tactatatgt attgggtgcg ccaagcgcca   180
gggcagggcc tcgaatggat gggtggcatc aatccgagca acggggggcac caactttaac   240
gaaaagttta aaaccgggt caccttgaca acgacagta gcacgactac cgcttatatg   300
gagctgaaga gtttgcagtt tgatgatact gcggtttatt attgtgcacg cagagattat   360
aggttcgaca tgggcttcga ctactggggt caaggtacta cggtaactgt atcatctgct   420
agtacaaagg gcccttccgt tttcccctc gccccgtgca gccgctcaac gtccgaaagc   480
accgctgcac ttgggtgcct tgtaaaagac tattttccag agccagttac cgtgtcttgg   540
aatagtggcg cacttacgtc cggggtgcac acttttccgg ctgtcttgca atcctctgga   600
ctctattcct tgagtagcgt cgtaacagta ccaagtagta gtctcggcac caaaacgtat   660
acgtgcaatg ttgatcataa gcctagcaac acgaaagttg acaaaagagt tgagagtaaa   720
tatggacccc cctgtccgcc atgcccggcc cctgaattcc ttgggggccc gtctgtattt   780
cttttcccgc caagccgaa ggatacactg atgataagca gaacgcctga ggttacctgc   840
gtcgtggtcg acgtaagcca ggaagatcct gaggtgcaat taattggta tgtggacggg   900
gtcgaggttc ataatgcaaa acaaaaaccc gagaggagc aatttaattc aacgtacaga   960
gtcgttagcg tacttacagt gctgcaccag gattggctca acgggaagga gtataagtgc  1020
aaggtgtcta ataaaggttt gccctccagt atagaaaaaa ccatctcaaa ggcgaaagga  1080
```

```
cagcctagag aacctcaagt atatacccctc ccaccctccc aagaagagat gacaaagaac    1140
caagtgagtc tcacatgcct cgtcaagggt ttctacccaa gcgatatagc cgtagagtgg    1200
gaatcaaatg gtcagccgga gaataactac aaaactactc cgccagtctt ggatagcgac    1260 gggtctttttt tcctgtactc taggctgacg gtggacaagt caagatggca ggaaggaaat    1320
gtttttagct gctccgttat gcatgaggct ctccacaatc attatacaca aaaaagtttg    1380
tctctgtcat tggggaaatc cggggggtggc ggatccgatg aggctgcagg gataggccca    1440
gaagttcctg atgaccgcga cttcgagccc tccctaggcc cagtgtgccc cttccgctgt    1500
caatgccatc ttcgagtggt ccagtgttct gatttgggtc tggacaaagt gccaaaggat    1560
cttccccctg acacaactct gctagacctg caaaacaaca aataaccga atcaaagat    1620 ggagacttta agaacctgaa gaaccttcac gcattgattc ttgtcaacaa taaaattagc    1680
aaagttagtc ctggagcatt tacacctttg gtgaagttgg aacgacttta tctgtccaag    1740
aatcagctga aggaattgcc agaaaaaatg cccaaaactc ttcaggagct gcgtgcccat    1800
gagaatgaga tcaccaaagt gcgaaaagtt actttcaatg gactgaacca gatgattgtc    1860
atagaactgg gcaccaatcc gctgaagagc tcaggaattg aaaatggggc tttccaggga    1920
atgaagaagc tctcctacat ccgcattgct gataccaata tcaccagcat tcctcaaggt    1980
cttcctcctt cccttacgga attacatctt gatggcaaca aaatcagcag agttgatgca    2040
gctagcctga aaggactgaa taatttggct aagttgggat tgagtttcaa cagcatctct    2100
gctgttgaca atggctctct ggccaacacg cctcatctga gggagcttca cttggacaac    2160
aacaagctta ccagagtacc tggtgggctg gcagagcata agtacatcca ggttgtctac    2220
cttcataaca caatatctc tgtagttgga tcaagtgact tctgcccacc tggacacaac    2280
accaaaaagg cttcttattc gggtgtgagt cttttcagca acccggtcca gtactgggag    2340
atacagccat ccaccttcag atgtgtctac gtgcgctctg ccattcaact cggaaactat    2400
aagtga                                                              2406
```

<210> SEQ ID NO 41
<211> LENGTH: 801
<212> TYPE: PRT
<213> ORGANISM: Artificial Sequence
<220> FEATURE:
<223> OTHER INFORMATION: synthetic

<400> SEQUENCE: 41

Met Met Ser Phe Val Ser Leu Leu Leu Val Gly Ile Leu Phe His Ala
1               5                   10                  15

Thr Gln Ala Gln Val Gln Leu Val Gln Ser Gly Val Glu Val Lys Lys
            20                  25                  30

Pro Gly Ala Ser Val Lys Val Ser Cys Lys Ala Ser Gly Tyr Thr Phe
        35                  40                  45

Thr Asn Tyr Tyr Met Tyr Trp Val Arg Gln Ala Pro Gly Gln Gly Leu
    50                  55                  60

Glu Trp Met Gly Gly Ile Asn Pro Ser Asn Gly Gly Thr Asn Phe Asn
65                  70                  75                  80

Glu Lys Phe Lys Asn Arg Val Thr Leu Thr Thr Asp Ser Ser Thr Thr
                85                  90                  95

Thr Ala Tyr Met Glu Leu Lys Ser Leu Gln Phe Asp Asp Thr Ala Val
            100                 105                 110

Tyr Tyr Cys Ala Arg Arg Asp Tyr Arg Phe Asp Met Gly Phe Asp Tyr

-continued

```
            115                 120                 125
Trp Gly Gln Gly Thr Thr Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Lys Thr Tyr Thr Cys Asn Val
210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser Gln Glu
                275                 280                 285

Asp Pro Glu Val Gln Phe Asn Trp Tyr Val Asp Gly Val Glu Val His
290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
                340                 345                 350

Lys Thr Ile Ser Lys Ala Lys Gly Gln Pro Arg Glu Pro Gln Val Tyr
                355                 360                 365

Thr Leu Pro Pro Ser Gln Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
                420                 425                 430

Lys Ser Arg Trp Gln Glu Gly Asn Val Phe Ser Cys Ser Val Met His
                435                 440                 445

Glu Ala Leu His Asn His Tyr Thr Gln Lys Ser Leu Ser Leu Ser Leu
                450                 455                 460

Gly Lys Ser Gly Gly Gly Gly Ser Asp Glu Ala Ala Gly Ile Gly Pro
465                 470                 475                 480

Glu Val Pro Asp Asp Arg Asp Phe Glu Pro Ser Leu Gly Pro Val Cys
                485                 490                 495

Pro Phe Arg Cys Gln Cys His Leu Arg Val Val Gln Cys Ser Asp Leu
                500                 505                 510

Gly Leu Asp Lys Val Pro Lys Asp Leu Pro Pro Asp Thr Thr Leu Leu
                515                 520                 525

Asp Leu Gln Asn Asn Lys Ile Thr Glu Ile Lys Asp Gly Asp Phe Lys
530                 535                 540
```

Asn Leu Lys Asn Leu His Ala Leu Ile Leu Val Asn Asn Lys Ile Ser
545                 550                 555                 560

Lys Val Ser Pro Gly Ala Phe Thr Pro Leu Val Lys Leu Glu Arg Leu
            565                 570                 575

Tyr Leu Ser Lys Asn Gln Leu Lys Glu Leu Pro Glu Lys Met Pro Lys
        580                 585                 590

Thr Leu Gln Glu Leu Arg Ala His Glu Asn Glu Ile Thr Lys Val Arg
    595                 600                 605

Lys Val Thr Phe Asn Gly Leu Asn Gln Met Ile Val Ile Glu Leu Gly
610                 615                 620

Thr Asn Pro Leu Lys Ser Ser Gly Ile Glu Asn Gly Ala Phe Gln Gly
625                 630                 635                 640

Met Lys Lys Leu Ser Tyr Ile Arg Ile Ala Asp Thr Asn Ile Thr Ser
            645                 650                 655

Ile Pro Gln Gly Leu Pro Pro Ser Leu Thr Glu Leu His Leu Asp Gly
        660                 665                 670

Asn Lys Ile Ser Arg Val Asp Ala Ala Ser Leu Lys Gly Leu Asn Asn
    675                 680                 685

Leu Ala Lys Leu Gly Leu Ser Phe Asn Ser Ile Ser Ala Val Asp Asn
690                 695                 700

Gly Ser Leu Ala Asn Thr Pro His Leu Arg Glu Leu His Leu Asp Asn
705                 710                 715                 720

Asn Lys Leu Thr Arg Val Pro Gly Gly Leu Ala Glu His Lys Tyr Ile
            725                 730                 735

Gln Val Val Tyr Leu His Asn Asn Ile Ser Val Val Gly Ser Ser
        740                 745                 750

Asp Phe Cys Pro Pro Gly His Asn Thr Lys Lys Ala Ser Tyr Ser Gly
    755                 760                 765

Val Ser Leu Phe Ser Asn Pro Val Gln Tyr Trp Glu Ile Gln Pro Ser
770                 775                 780

Thr Phe Arg Cys Val Tyr Val Arg Ser Ala Ile Gln Leu Gly Asn Tyr
785                 790                 795                 800

Lys

<210> SEQ ID NO 42
<211> LENGTH: 714
<212> TYPE: DNA
<213> ORGANISM: Artificial Sequence
<220> FEATURE:
<223> OTHER INFORMATION: synthetic

<400> SEQUENCE: 42
atgatgtcct ttgtctctct gctcctggtt ggcatcctat tccatgccac ccaggccgaa      60
attgttctta cgcagagtcc agcaactttg tcactctctc ccggcgaacg agcgacattg     120
tcctgtcgcg cgagtaaggg tgtctcaaca tctggatact catatctgca ttggtaccag     180
caaaaaccgg gacaagcgcc gcgattgctg atttatctcg cctcctacct tgaaagtggt     240
gtgcctgcga ggttctccgg tagtggatca ggcaccgatt tcactttgac catcagcagc     300
ctcgaaccag aagattttgc cgtctactac tgccaacata gcagggattt gccactgaca     360
ttcggcgggg gtacgaaagt tgagattaaa cggactgtag cggcaccttc tgtcttcatc     420
ttcccaccaa gcgatgagca gcttaaaagc ggtacagctt cagtggtgtg ccttttgaac     480 aactttatc cgcgagaagc caaggtccaa tggaaggtgg ataacgcttt gcaatccggt     540

```
aactcacagg agtcagtaac agagcaagat agtaaagata gcacgtattc acttagcagt    600
acccttactc ttagcaaggc tgattatgaa aaacataagg tatatgcgtg cgaggtaacg    660
caccaaggac ttagctcccc agtgacgaag tcatttaacc ggggggagtg ctga          714
```

<210> SEQ ID NO 43
<211> LENGTH: 237
<212> TYPE: PRT
<213> ORGANISM: Artificial Sequence
<220> FEATURE:
<223> OTHER INFORMATION: synthetic

<400> SEQUENCE: 43

```
Met Met Ser Phe Val Ser Leu Leu Leu Val Gly Ile Leu Phe His Ala
1               5                   10                  15

Thr Gln Ala Glu Ile Val Leu Thr Gln Ser Pro Ala Thr Leu Ser Leu
            20                  25                  30

Ser Pro Gly Glu Arg Ala Thr Leu Ser Cys Arg Ala Ser Lys Gly Val
        35                  40                  45

Ser Thr Ser Gly Tyr Ser Tyr Leu His Trp Tyr Gln Gln Lys Pro Gly
    50                  55                  60

Gln Ala Pro Arg Leu Leu Ile Tyr Leu Ala Ser Tyr Leu Glu Ser Gly
65                  70                  75                  80

Val Pro Ala Arg Phe Ser Gly Ser Gly Ser Gly Thr Asp Phe Thr Leu
                85                  90                  95

Thr Ile Ser Ser Leu Glu Pro Glu Asp Phe Ala Val Tyr Tyr Cys Gln
            100                 105                 110

His Ser Arg Asp Leu Pro Leu Thr Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 44
<211> LENGTH: 447
<212> TYPE: PRT
<213> ORGANISM: Artificial Sequence
<220> FEATURE:
<223> OTHER INFORMATION: synthetic

<400> SEQUENCE: 44

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45
```

Gly Gly Ile Asn Pro Ser Asn Gly Gly Thr Asn Phe Asn Glu Lys Phe
            50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
                115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 45
<211> LENGTH: 218

```
<212> TYPE: PRT
<213> ORGANISM: Artificial Sequence
<220> FEATURE:
<223> OTHER INFORMATION: synthetic

<400> SEQUENCE: 45

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 46
<211> LENGTH: 14
<212> TYPE: PRT
<213> ORGANISM: Artificial Sequence
<220> FEATURE:
<223> OTHER INFORMATION: synthetic

<400> SEQUENCE: 46

Gly Pro Phe Gln Gln Arg Gly Leu Phe Asp Phe Met Leu Glu
1               5                   10

<210> SEQ ID NO 47
<211> LENGTH: 42
<212> TYPE: DNA
<213> ORGANISM: Artificial Sequence
<220> FEATURE:
<223> OTHER INFORMATION: synthetic

<400> SEQUENCE: 47
ggcccgtttc aacagagagg cttatttgac tttatgctag aa                         42

<210> SEQ ID NO 48
<211> LENGTH: 990
<212> TYPE: DNA
<213> ORGANISM: Artificial Sequence
```

```
<220> FEATURE:
<223> OTHER INFORMATION: synthetic

<400> SEQUENCE: 48
gatgaggctg cagggatagg cccagaagtt cctgatgacc gcgacttcga gccctccta      60
ggcccagtgt gcccccttccg ctgtcaatgc catcttcgag tggtccagtg ttctgatttg   120
ggtctggaca aagtgccaaa ggatcttccc cctgacacaa ctctgctaga cctgcaaaac   180
aacaaaataa ccgaaatcaa agatggagac tttaagaacc tgaagaacct tcacgcattg   240
attcttgtca caataaaat tagcaaagtt agtcctggag catttacacc tttggtgaag    300
ttggaacgac tttatctgtc caagaatcag ctgaaggaat gccagaaaaa aatgcccaaa   360
actcttcagg agctgcgtgc ccatgagaat gagatcacca aagtgcgaaa agttactttc   420
aatggactga accagatgat tgtcatagaa ctgggcacca atccgctgaa gagctcagga   480
attgaaaatg gggctttcca gggaatgaag aagctctcct acatccgcat tgctgatacc   540
aatatcacca gcattcctca aggtcttcct ccttccctta cggaattaca tcttgatggc   600
aacaaaatca gcagagttga tgcagctagc ctgaaaggac tgaataattt ggctaagttg   660
ggattgagtt tcaacagcat ctctgctgtt gacaatggct ctctggccaa cacgcctcat   720
ctgagggagc ttcacttgga caacaacaag cttaccagag tacctggtgg gctggcagag   780
cataagtaca tccaggttgt ctaccttcat aacaacaata tctctgtagt tggatcaagt   840
gacttctgcc cacctggaca caacaccaaa aaggcttctt attcgggtgt gagtcttttc   900
agcaacccgg tccagtactg ggagatacag ccatccacct tcagatgtgt ctacgtgcgc   960
tctgccattc aactcggaaa ctataagtga                                     990

<210> SEQ ID NO 49
<211> LENGTH: 2415
<212> TYPE: DNA
<213> ORGANISM: Artificial Sequence
<220> FEATURE:
<223> OTHER INFORMATION: synthetic

<400> SEQUENCE: 49
atgatgtcct ttgtctctct gctcctggtt ggcatcctat tccatgccac ccaggccgag    60
gtacagcttt tggagtcagg cggggggctc gtccaacctg gggggtcact ccggttgtca   120
tgtgctgcca gtggcttcac attctcatct tacattatga tgtgggttcg acaggccct   180
gggaaggggc tggagtgggt ttcctccatc taccctccg ggggaattac cttctatgcc    240
gacacggtaa agggtcgctt cactataagt cgagataaca gcaaaaatac gctgtatctc   300
cagatgaact ctctcagggc tgaggacaca gctgtatatt actgcgcgcg gattaagttg   360
gggaccgtca acagtgtgga ttactggggt caaggcactc tggtaaccgt atcctcagca   420
tccaccaagg gcccaagtgt attcccgctg gccccttcaa gtaaatccac gtctggcggc   480
acagccgctc tcggttgcct ggttaaggac tacttcccag aacctgtcac tgtcagttgg   540
aactcaggcg cattgacatc tggtgtccat acattcccg cagtcctgca aagctctgga   600
ctttacagtc ttagtagcgt agtgacagtc ccatcttcaa gtcttgggac ccaaacttat   660
atttgcaacg taaatcataa accctccaac actaaagtag acaaaaaagt agagccgaaa   720
tcttgcgaca aaacgcatac atgcccacca tgtcccgctc cggaactcct gggcggcccg   780
tccgtttttc tctttccccc aaagcccaag gatacgctta tgatcagcag aacaccggaa   840
gttacttgtg tagtcgttga cgtgtctcac gaagatcccg aagtcaaatt taattggtat   900
```

```
gtggatggcg tcgaagtgca caacgcaaaa accaaaccca gagaggaaca gtataacagc    960
acgtatcgag tggtctccgt acttacggtc ctccaccagg actggttgaa tggcaaggag   1020
tacaagtgca aagtgagcaa taaagcgttg ccagccccga tcgaaaaaac catcagcaag   1080
gccaagggac agcctagaga gccgcaggtt tacaccttgc cgccatcaag ggatgaactg   1140
actaaaaacc aggtatccct gacctgcctg gttaagggtt tttaccccag tgatatagcg   1200
gttgaatggg agtctaacgg gcagccagag aacaactaca aaacgacacc tcccgttctg   1260
gattccgatg gcagcttttt cttgtattct aaactcaccg tggataaatc ccgatggcag   1320
caaggcaacg tcttctcctg cagcgtgatg catgaagcct tgcacaacca ctatacccaa   1380
aagagtctca gcctgtcacc cgggaaatcc gggggtggcg gatccgatga ggctgcaggg   1440
ataggcccag aagttcctga tgaccgcgac ttcgagccct ccctaggccc agtgtgcccc   1500
ttccgctgtc aatgccatct tcgagtggtc cagtgttctg atttgggtct ggacaaagtg   1560
ccaaaggatc ttccccctga cacaactctg ctagacctgc aaaacaacaa aataaccgaa   1620
atcaaagatg gagactttaa gaacctgaag aaccttcacg cattgattct tgtcaacaat   1680
aaaattagca agttagtcc tggagcattt acacctttgg tgaagttgga acgactttat   1740
ctgtccaaga atcagctgaa ggaattgcca gaaaaaatgc caaaactct tcaggagctg   1800 cgtgcccatg agaatgagat caccaaagtg cgaaaagtta ctttcaatgg actgaaccag   1860
atgattgtca tagaactggg caccaatccg ctgaagagct caggaattga aaatggggct   1920
ttccagggaa tgaagaagct ctcctacatc cgcattgctg ataccaatat caccagcatt   1980
cctcaaggtc ttcctccttc ccttacggaa ttacatcttg atggcaacaa atcagcaga   2040 gttgatgcag ctagcctgaa aggactgaat aatttggcta agttgggatt gagtttcaac   2100
agcatctctg ctgttgacaa tggctctctg gccaacacgc tcatctgag ggagcttcac   2160 ttggacaaca acaagcttac cagagtacct ggtgggctgg cagagcataa gtacatccag   2220
gttgtctacc ttcataacaa caatatctct gtagttggat caagtgactt ctgcccacct   2280
ggacacaaca ccaaaaaggc ttcttattcg ggtgtgagtc ttttcagcaa cccggtccag   2340
tactgggaga tacagccatc caccttcaga tgtgtctacg tgcgctctgc cattcaactc   2400
ggaaactata agtga                                                    2415
```

<210> SEQ ID NO 50
<211> LENGTH: 804
<212> TYPE: PRT
<213> ORGANISM: Artificial Sequence
<220> FEATURE:
<223> OTHER INFORMATION: synthetic

<400> SEQUENCE: 50

Met Met Ser Phe Val Ser Leu Leu Leu Val Gly Ile Leu Phe His Ala
1               5                   10                  15

Thr Gln Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ile Met Met Trp Val Arg Gln Ala Pro Gly Lys Gly Leu
    50                  55                  60

Glu Trp Val Ser Ser Ile Tyr Pro Ser Gly Gly Ile Thr Phe Tyr Ala
65                  70                  75                  80

Asp Thr Val Lys Gly Arg Phe Thr Ile Ser Arg Asp Asn Ser Lys Asn
                85                  90                  95

-continued

Thr Leu Tyr Leu Gln Met Asn Ser Leu Arg Ala Glu Asp Thr Ala Val
            100                 105                 110

Tyr Tyr Cys Ala Arg Ile Lys Leu Gly Thr Val Thr Val Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
            210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
            450                 455                 460

Leu Ser Pro Gly Lys Ser Gly Gly Gly Ser Asp Glu Ala Ala Gly
465                 470                 475                 480

Ile Gly Pro Glu Val Pro Asp Asp Arg Asp Phe Glu Pro Ser Leu Gly
            485                 490                 495

Pro Val Cys Pro Phe Arg Cys Gln Cys His Leu Arg Val Val Gln Cys
            500                 505                 510

Ser Asp Leu Gly Leu Asp Lys Val Pro Lys Asp Leu Pro Pro Asp Thr
515                 520                 525

Thr Leu Leu Asp Leu Gln Asn Asn Lys Ile Thr Glu Ile Lys Asp Gly
530                 535                 540

Asp Phe Lys Asn Leu Lys Asn Leu His Ala Leu Ile Leu Val Asn Asn
545                 550                 555                 560

Lys Ile Ser Lys Val Ser Pro Gly Ala Phe Thr Pro Leu Val Lys Leu
            565                 570                 575

Glu Arg Leu Tyr Leu Ser Lys Asn Gln Leu Lys Glu Leu Pro Glu Lys
                580                 585                 590

Met Pro Lys Thr Leu Gln Glu Leu Arg Ala His Glu Asn Glu Ile Thr
            595                 600                 605

Lys Val Arg Lys Val Thr Phe Asn Gly Leu Asn Gln Met Ile Val Ile
            610                 615                 620

Glu Leu Gly Thr Asn Pro Leu Lys Ser Ser Gly Ile Glu Asn Gly Ala
625                 630                 635                 640

Phe Gln Gly Met Lys Lys Leu Ser Tyr Ile Arg Ile Ala Asp Thr Asn
                645                 650                 655

Ile Thr Ser Ile Pro Gln Gly Leu Pro Pro Ser Leu Thr Glu Leu His
            660                 665                 670

Leu Asp Gly Asn Lys Ile Ser Arg Val Asp Ala Ala Ser Leu Lys Gly
            675                 680                 685

Leu Asn Asn Leu Ala Lys Leu Gly Leu Ser Phe Asn Ser Ile Ser Ala
            690                 695                 700

Val Asp Asn Gly Ser Leu Ala Asn Thr Pro His Leu Arg Glu Leu His
705                 710                 715                 720

Leu Asp Asn Asn Lys Leu Thr Arg Val Pro Gly Gly Leu Ala Glu His
                725                 730                 735

Lys Tyr Ile Gln Val Val Tyr Leu His Asn Asn Asn Ile Ser Val Val
                740                 745                 750

Gly Ser Ser Asp Phe Cys Pro Pro Gly His Asn Thr Lys Lys Ala Ser
            755                 760                 765

Tyr Ser Gly Val Ser Leu Phe Ser Asn Pro Val Gln Tyr Trp Glu Ile
770                 775                 780

Gln Pro Ser Thr Phe Arg Cys Val Tyr Val Arg Ser Ala Ile Gln Leu
785                 790                 795                 800

Gly Asn Tyr Lys

<210> SEQ ID NO 51
<211> LENGTH: 708
<212> TYPE: DNA
<213> ORGANISM: Artificial Sequence
<220> FEATURE:
<223> OTHER INFORMATION: synthetic

<400> SEQUENCE: 51

```
atgatgtcct tgtctctctc gctcctggtt ggcatcctat tccatgccac ccaggcccag      60
tctgcactta cacaaccggc gtccgtttcc ggatctccag gacagagcat tactatcagt     120
tgcacgggaa cctcctcaga cgtagggggg tataattatg tgtcttggta tcaacagcat     180
cccgggaaag cccccaaact gatgatctac gatgtcagca atagaccaag cggtgtgagt     240
aatcgattta gcgggtctaa atctggtaac acagcatccc tcactattag tggactgcaa     300
gcagaagatg aggcagacta ttattgcagt agctatacgt ctagttccac ccgcgttttt     360
ggcactggga cgaaagtcac cgttctcgga caaccaaaag caaaccccac cgtgactctg     420
```

```
tttccgccta gcagcgaaga attgcaggcc aataaggcga cactcgtatg ccttatctcc      480
gacttctacc cgggcgctgt gacagtcgcg tggaaagccg acggcagccc tgttaaagct      540
ggagtcgaga ccacgaagcc gtccaagcag agtaacaata agtatgctgc atccagttat      600
ctctctctca ctccggaaca gtggaagtcc catcggtcct atagttgcca agtgacccat      660
gagggttcca ccgtagagaa aacggtagca cctaccgaat gtagttga                  708
```

```
<210> SEQ ID NO 52
<211> LENGTH: 235
<212> TYPE: PRT
<213> ORGANISM: Artificial Sequence
<220> FEATURE:
<223> OTHER INFORMATION: synthetic

<400> SEQUENCE: 52
```

| | | | | | | | | | | | | | | |
|---|---|---|---|---|---|---|---|---|---|---|---|---|---|---|
| Met | Met | Ser | Phe | Val | Ser | Leu | Leu | Leu | Val | Gly | Ile | Leu | Phe | His | Ala |
| 1 | | | | 5 | | | | | 10 | | | | | 15 | |

| Thr | Gln | Ala | Gln | Ser | Ala | Leu | Thr | Gln | Pro | Ala | Ser | Val | Ser | Gly | Ser |
| | | | 20 | | | | | 25 | | | | | 30 | | |

| Pro | Gly | Gln | Ser | Ile | Thr | Ile | Ser | Cys | Thr | Gly | Thr | Ser | Ser | Asp | Val |
| | | | 35 | | | | | 40 | | | | | 45 | | |

| Gly | Gly | Tyr | Asn | Tyr | Val | Ser | Trp | Tyr | Gln | Gln | His | Pro | Gly | Lys | Ala |
| | | | 50 | | | | | 55 | | | | | 60 | | |

| Pro | Lys | Leu | Met | Ile | Tyr | Asp | Val | Ser | Asn | Arg | Pro | Ser | Gly | Val | Ser |
| 65 | | | | | 70 | | | | | 75 | | | | | 80 |

| Asn | Arg | Phe | Ser | Gly | Ser | Lys | Ser | Gly | Asn | Thr | Ala | Ser | Leu | Thr | Ile |
| | | | | 85 | | | | | 90 | | | | | 95 | |

| Ser | Gly | Leu | Gln | Ala | Glu | Asp | Glu | Ala | Asp | Tyr | Tyr | Cys | Ser | Ser | Tyr |
| | | | | 100 | | | | | 105 | | | | | 110 | |

| Thr | Ser | Ser | Ser | Thr | Arg | Val | Phe | Gly | Thr | Gly | Thr | Lys | Val | Thr | Val |
| | | | | 115 | | | | | 120 | | | | | 125 | |

| Leu | Gly | Gln | Pro | Lys | Ala | Asn | Pro | Thr | Val | Thr | Leu | Phe | Pro | Pro | Ser |
| | | | | 130 | | | | | 135 | | | | | 140 | |

| Ser | Glu | Glu | Leu | Gln | Ala | Asn | Lys | Ala | Thr | Leu | Val | Cys | Leu | Ile | Ser |
| 145 | | | | | 150 | | | | | 155 | | | | | 160 |

| Asp | Phe | Tyr | Pro | Gly | Ala | Val | Thr | Val | Ala | Trp | Lys | Ala | Asp | Gly | Ser |
| | | | | 165 | | | | | 170 | | | | | 175 | |

| Pro | Val | Lys | Ala | Gly | Val | Glu | Thr | Thr | Lys | Pro | Ser | Lys | Gln | Ser | Asn |
| | | | | 180 | | | | | 185 | | | | | 190 | |

| Asn | Lys | Tyr | Ala | Ala | Ser | Ser | Tyr | Leu | Ser | Leu | Thr | Pro | Glu | Gln | Trp |
| | | | | 195 | | | | | 200 | | | | | 205 | |

| Lys | Ser | His | Arg | Ser | Tyr | Ser | Cys | Gln | Val | Thr | His | Glu | Gly | Ser | Thr |
| | | | | 210 | | | | | 215 | | | | | 220 | |

| Val | Glu | Lys | Thr | Val | Ala | Pro | Thr | Glu | Cys | Ser | | | | | |
| 225 | | | | | 230 | | | | | 235 | | | | | |

```
<210> SEQ ID NO 53
<211> LENGTH: 3420
<212> TYPE: DNA
<213> ORGANISM: Artificial Sequence
<220> FEATURE:
<223> OTHER INFORMATION: synthetic

<400> SEQUENCE: 53
atgatgtcct tgtctctctct gctcctggtt ggcatcctat tccatgccac ccaggccgag      60
gtacagcttt tggagtcagg cgggggggctc gtccaacctg gggggtcact ccggttgtca     120
```

-continued

```
tgtgctgcca gtggcttcac attctcatct tacattatga gtgggttcg acaggcccct      180 gggaagggc tggagtgggt ttcctccatc taccccctccg gggaattac cttctatgcc      240 gacacggtaa agggtcgctt cactataagt cgagataaca gcaaaaatac gctgtatctc      300
cagatgaact ctctcagggc tgaggacaca gctgtatatt actgcgcgcg gattaagttg      360
gggaccgtca caacagtgga ttactggggt caaggcactc tggtaaccgt atcctcagca      420
tccaccaagg gcccaagtgt attcccgctg gcccttcaa gtaaatccac gtctggcggc      480
acagccgctc tcggttgcct ggttaaggac tacttcccag aacctgtcac tgtcagttgg      540
aactcaggcg cattgacatc tggtgtccat acattcccg cagtcctgca aagctctgga      600
ctttacagtc ttagtagcgt agtgacagtc ccatcttcaa gtcttgggac ccaaacttat      660
atttgcaacg taaatcataa accctccaac actaaagtag acaaaaaagt agagccgaaa      720
tcttgcgaca aaacgcatac atgcccacca tgtcccgctc cggaactcct gggcggcccg      780 tccgttttc tctttccccc aaagcccaag gatacgctta tgatcagcag aacaccggaa      840
gttacttgtg tagtcgttga cgtgtctcac gaagatcccg aagtcaaatt taattggtat      900
gtggatggcg tcgaagtgca caacgcaaaa accaaaccca gagaggaaca gtataacagc      960
acgtatcgag tggtctccgt acttacggtc ctccaccagg actggttgaa tggcaaggag      1020
tacaagtgca aagtgagcaa taaagcgttg ccagccccga tcgaaaaaac catcagcaag      1080
gccaagggac agcctagaga gccgcaggtt tacaccttgc cgccatcaag ggatgaactg      1140
actaaaaacc aggtatccct gacctgcctg gttaagggtt tttacccccag tgatatagcg      1200 gttgaatggg agtctaacgg gcagccagag aacaactaca aaacgacacc tcccgttctg      1260
gattccgatg gcagctttt cttgtattct aaactcaccg tggataaatc ccgatggcag      1320
caaggcaacg tcttctcctg cagcgtgatg catgaagcct tgcacaacca ctatacccaa      1380
aagagtctca gcctgtcacc cgggaaatcc gggggtggcg gatccgatga ggctgcaggg      1440
ataggcccag aagttcctga tgaccgcgac ttcgagccct ccctaggccc agtgtgcccc      1500
ttccgctgtc aatgccatct tcgagtggtc cagtgttctg atttgggtct ggacaaagtg      1560
ccaaaggatc ttccccctga cacaactctg ctagacctgc aaaacaacaa aataaccgaa      1620
atcaaagatg gagactttaa gaacctgaag aaccttcacg cattgattct tgtcaacaat      1680
aaaattagca agttagtcc tggagcattt acacctttgg tgaagttgga acgactttat      1740
ctgtccaaga atcagctgaa ggaattgcca gaaaaaatgc caaaactct tcaggagctg      1800 cgtgcccatg agaatgagat caccaaagtg cgaaaagtta ctttcaatgg actgaaccag      1860
atgattgtca tagaactggg caccaatccg ctgaagagct caggaattga aaatggggct      1920
ttccagggaa tgaagaagct ctcctacatc cgcattgctg ataccaatat caccagcatt      1980
cctcaaggtc ttcctccttc ccttacggaa ttacatcttg atggcaacaa aatcagcaga      2040
gttgatgcag ctagcctgaa aggactgaat aatttggcta agttgggatt gagtttcaac      2100
agcatctctg ctgttgacaa tggctctctg gccaacacgc ctcatctgag ggagcttcac      2160
ttggacaaca acaagcttac cagagtacct ggtgggctgg cagagcataa gtacatccag      2220
gttgtctacc ttcataacaa caatatctct gtagttggat caagtgactt ctgcccacct      2280
ggacacaaca ccaaaaggc ttcttattcg ggtgtgagtc ttttcagcaa cccggtccag      2340
tactgggaga tacagccatc caccttcaga tgtgtctacg tgcgctctgc cattcaactc      2400
ggaaactata agtccggggg tggcggatcc gatgaggctg cagggatagg cccagaagtt      2460
```

```
cctgatgacc gcgacttcga gccctcccta ggcccagtgt gccccttccg ctgtcaatgc    2520
catcttcgag tggtccagtg ttctgatttg ggtctggaca aagtgccaaa ggatcttccc    2580
cctgacacaa ctctgctaga cctgcaaaac aacaaaataa ccgaaatcaa agatggagac    2640
tttaagaacc tgaagaacct tcacgcattg attcttgtca acaataaaat tagcaaagtt    2700
agtcctggag catttacacc tttggtgaag ttggaacgac tttatctgtc caagaatcag    2760
ctgaaggaat tgccagaaaa aatgcccaaa actcttcagg agctgcgtgc ccatgagaat    2820
gagatcacca aagtgcgaaa agttactttc aatggactga accagatgat tgtcatagaa    2880
ctgggcacca atccgctgaa gagctcagga attgaaaatg gggctttcca gggaatgaag    2940
aagctctcct acatccgcat tgctgatacc aatatcacca gcattcctca aggtcttcct    3000
ccttccctta cggaattaca tcttgatggc aacaaaatca gcagagttga tgcagctagc    3060
ctgaaaggac tgaataattt ggctaagttg ggattgagtt tcaacagcat ctctgctgtt    3120
gacaatggct ctctggccaa cacgcctcat ctgagggagc ttcacttgga caacaacaag    3180
cttaccagag tacctggtgg gctggcagag cataagtaca tccaggttgt ctaccttcat    3240
aacaacaata tctctgtagt tggatcaagt gacttctgcc cacctggaca caacaccaaa    3300
aaggcttctt attcgggtgt gagtctttc agcaacccgg tccagtactg ggagatacag    3360
ccatccacct tcagatgtgt ctacgtgcgc tctgccattc aactcggaaa ctataagtga    3420
```

<210> SEQ ID NO 54
<211> LENGTH: 1139
<212> TYPE: PRT
<213> ORGANISM: Artificial Sequence
<220> FEATURE:
<223> OTHER INFORMATION: synthetic

<400> SEQUENCE: 54

```
Met Met Ser Phe Val Ser Leu Leu Leu Val Gly Ile Leu Phe His Ala
1               5                   10                  15

Thr Gln Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ile Met Met Trp Val Arg Gln Ala Pro Gly Lys Gly Leu
    50                  55                  60

Glu Trp Val Ser Ser Ile Tyr Pro Ser Gly Gly Ile Thr Phe Tyr Ala
65                  70                  75                  80

Asp Thr Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ile Lys Leu Gly Thr Val Thr Thr Val Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
```

-continued

```
                195                 200                 205
Thr Val Pro Ser Ser Leu Gly Thr Gln Thr Tyr Ile Cys Asn Val
210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
        290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
450                 455                 460

Leu Ser Pro Gly Lys Ser Gly Gly Gly Gly Ser Asp Glu Ala Ala Gly
465                 470                 475                 480

Ile Gly Pro Glu Val Pro Asp Asp Arg Asp Phe Glu Pro Ser Leu Gly
                485                 490                 495

Pro Val Cys Pro Phe Arg Cys Gln Cys His Leu Arg Val Val Gln Cys
                500                 505                 510

Ser Asp Leu Gly Leu Asp Lys Val Pro Lys Asp Leu Pro Pro Asp Thr
        515                 520                 525

Thr Leu Leu Asp Leu Gln Asn Asn Lys Ile Thr Glu Ile Lys Asp Gly
        530                 535                 540

Asp Phe Lys Asn Leu Lys Asn Leu His Ala Leu Ile Leu Val Asn Asn
545                 550                 555                 560

Lys Ile Ser Lys Val Ser Pro Gly Ala Phe Thr Pro Leu Val Lys Leu
                565                 570                 575

Glu Arg Leu Tyr Leu Ser Lys Asn Gln Leu Lys Glu Leu Pro Glu Lys
                580                 585                 590

Met Pro Lys Thr Leu Gln Glu Leu Arg Ala His Glu Asn Glu Ile Thr
                595                 600                 605

Lys Val Arg Lys Val Thr Phe Asn Gly Leu Asn Gln Met Ile Val Ile
610                 615                 620
```

-continued

```
Glu Leu Gly Thr Asn Pro Leu Lys Ser Ser Gly Ile Glu Asn Gly Ala
625                 630                 635                 640

Phe Gln Gly Met Lys Lys Leu Ser Tyr Ile Arg Ile Ala Asp Thr Asn
                645                 650                 655

Ile Thr Ser Ile Pro Gln Gly Leu Pro Pro Ser Leu Thr Glu Leu His
            660                 665                 670

Leu Asp Gly Asn Lys Ile Ser Arg Val Asp Ala Ala Ser Leu Lys Gly
        675                 680                 685

Leu Asn Asn Leu Ala Lys Leu Gly Leu Ser Phe Asn Ser Ile Ser Ala
690                 695                 700

Val Asp Asn Gly Ser Leu Ala Asn Thr Pro His Leu Arg Glu Leu His
705                 710                 715                 720

Leu Asp Asn Asn Lys Leu Thr Arg Val Pro Gly Gly Leu Ala Glu His
                725                 730                 735

Lys Tyr Ile Gln Val Val Tyr Leu His Asn Asn Ile Ser Val Val
                740                 745                 750

Gly Ser Ser Asp Phe Cys Pro Pro Gly His Asn Thr Lys Lys Ala Ser
            755                 760                 765

Tyr Ser Gly Val Ser Leu Phe Ser Asn Pro Val Gln Tyr Trp Glu Ile
770                 775                 780

Gln Pro Ser Thr Phe Arg Cys Val Tyr Val Arg Ser Ala Ile Gln Leu
785                 790                 795                 800

Gly Asn Tyr Lys Ser Gly Gly Gly Ser Asp Glu Ala Ala Gly Ile
                805                 810                 815

Gly Pro Glu Val Pro Asp Asp Arg Asp Phe Glu Pro Ser Leu Gly Pro
                820                 825                 830

Val Cys Pro Phe Arg Cys Gln Cys His Leu Arg Val Val Gln Cys Ser
                835                 840                 845

Asp Leu Gly Leu Asp Lys Val Pro Lys Asp Leu Pro Pro Asp Thr Thr
850                 855                 860

Leu Leu Asp Leu Gln Asn Asn Lys Ile Thr Glu Ile Lys Asp Gly Asp
865                 870                 875                 880

Phe Lys Asn Leu Lys Asn Leu His Ala Leu Ile Leu Val Asn Asn Lys
                885                 890                 895

Ile Ser Lys Val Ser Pro Gly Ala Phe Thr Pro Leu Val Lys Leu Glu
            900                 905                 910

Arg Leu Tyr Leu Ser Lys Asn Gln Leu Lys Glu Leu Pro Glu Lys Met
        915                 920                 925

Pro Lys Thr Leu Gln Glu Leu Arg Ala His Glu Asn Glu Ile Thr Lys
    930                 935                 940

Val Arg Lys Val Thr Phe Asn Gly Leu Asn Gln Met Ile Val Ile Glu
945                 950                 955                 960

Leu Gly Thr Asn Pro Leu Lys Ser Ser Gly Ile Glu Asn Gly Ala Phe
                965                 970                 975

Gln Gly Met Lys Lys Leu Ser Tyr Ile Arg Ile Ala Asp Thr Asn Ile
            980                 985                 990

Thr Ser Ile Pro Gln Gly Leu Pro Pro Ser Leu Thr Glu Leu His Leu
        995                 1000                1005

Asp Gly Asn Lys Ile Ser Arg Val Asp Ala Ala Ser Leu Lys Gly
    1010                1015                1020

Leu Asn Asn Leu Ala Lys Leu Gly Leu Ser Phe Asn Ser Ile Ser
    1025                1030                1035
```

| | | | | | | | | | | | |
|---|---|---|---|---|---|---|---|---|---|---|---|
| Ala | Val | Asp | Asn | Gly | Ser | Leu | Ala | Asn | Thr | Pro | His | Leu | Arg | Glu |
| | 1040 | | | | 1045 | | | | | 1050 | | | | |
| Leu | His | Leu | Asp | Asn | Asn | Lys | Leu | Thr | Arg | Val | Pro | Gly | Gly | Leu |
| 1055 | | | | | 1060 | | | | | 1065 | | | | |
| Ala | Glu | His | Lys | Tyr | Ile | Gln | Val | Val | Tyr | Leu | His | Asn | Asn | Asn |
| 1070 | | | | | 1075 | | | | | 1080 | | | | |
| Ile | Ser | Val | Val | Gly | Ser | Ser | Asp | Phe | Cys | Pro | Pro | Gly | His | Asn |
| 1085 | | | | | 1090 | | | | | 1095 | | | | |
| Thr | Lys | Lys | Ala | Ser | Tyr | Ser | Gly | Val | Ser | Leu | Phe | Ser | Asn | Pro |
| 1100 | | | | | 1105 | | | | | 1110 | | | | |
| Val | Gln | Tyr | Trp | Glu | Ile | Gln | Pro | Ser | Thr | Phe | Arg | Cys | Val | Tyr |
| 1115 | | | | | 1120 | | | | | 1125 | | | | |
| Val | Arg | Ser | Ala | Ile | Gln | Leu | Gly | Asn | Tyr | Lys | | | | |
| 1130 | | | | | 1135 | | | | | | | | | |

<210> SEQ ID NO 55
<211> LENGTH: 2373
<212> TYPE: DNA
<213> ORGANISM: Artificial Sequence
<220> FEATURE:
<223> OTHER INFORMATION: synthetic

<400> SEQUENCE: 55

| | | | | | |
|---|---|---|---|---|---|
| atgatgtcct | ttgtctctct | gctcctggtt | ggcatcctat | tccatgccac | ccaggccgag | 60 |
| gtacagcttt | tggagtcagg | cggggggctc | gtccaacctg | ggggtcact | ccggttgtca | 120 |
| tgtgctgcca | gtggcttcac | attctcatct | tacattatga | tgtgggttcg | acaggccct | 180 |
| gggaagggc | tggagtgggt | tcctccatc | taccctccg | gggaattac | cttctatgcc | 240 |
| gacacggtaa | agggtcgctt | cactataagt | cgagataaca | gcaaaaatac | gctgtatctc | 300 |
| cagatgaact | ctctcagggc | tgaggacaca | gctgtatatt | actgcgcgcg | gattaagttg | 360 |
| gggaccgtca | aacagtgga | ttactgggt | caaggcactc | tggtaaccgt | atcctcagca | 420 |
| tccaccaagg | gcccaagtgt | attcccgctg | gcccccttcaa | gtaaatccac | gtctggcggc | 480 |
| acagccgctc | tcggttgcct | ggttaaggac | tacttcccag | aacctgtcac | tgtcagttgg | 540 |
| aactcaggcg | cattgacatc | tggtgtccat | acattccccg | cagtcctgca | aagctctgga | 600 |
| ctttacagtc | ttagtagcgt | agtgacagtc | ccatcttcaa | gtcttgggac | ccaaacttat | 660 |
| atttgcaacg | taaatcataa | accctccaac | actaaagtag | acaaaaaagt | agagccgaaa | 720 |
| tcttgcgaca | aaacgcatac | atgcccacca | tgtcccgctc | cggaactcct | gggcggcccg | 780 |
| tccgtttttc | tctttccccc | aaagcccaag | gatacgctta | tgatcagcag | aacaccggaa | 840 |
| gttacttgtg | tagtcgttga | cgtgtctcac | gaagatcccg | aagtcaaatt | taattggtat | 900 |
| gtggatggcg | tcgaagtgca | aacgcaaaa | accaaaccca | gagaggaaca | gtataacagc | 960 |
| acgtatcgag | tggtctccgt | acttacggtc | ctccaccagg | actggttgaa | tggcaaggag | 1020 |
| tacaagtgca | aagtgagcaa | taagcgcgttg | ccagccccga | tcgaaaaaac | catcagcaag | 1080 |
| gccaagggac | agcctagaga | gccgcaggtt | tacaccttgc | cgccatcaag | ggatgaactg | 1140 |
| actaaaaacc | aggtatccct | gacctgcctg | gttaagggtt | tttaccccag | tgatatagcg | 1200 |
| gttgaatggg | agtctaacgg | gcagccagag | aacaactaca | aaacgacacc | tcccgttctg | 1260 |
| gattccgatg | gcagctttt | cttgtattct | aaactcaccg | tggataaatc | ccgatggcag | 1320 |
| caaggcaacg | tcttctcctg | cagcgtgatg | catgaagcct | tgcacaacca | ctataccaa | 1380 |
| aagagtctca | gcctgtcacc | cgggaaatcc | gggggtggcg | gatccgactt | cgagccctcc | 1440 |

```
ctaggcccag tgtgcccctt ccgctgtcaa tgccatcttc gagtggtcca gtgttctgat    1500
ttgggtctgg acaaagtgcc aaaggatctt cccctgaca caactctgct agacctgcaa    1560
aacaacaaaa taaccgaaat caaagatgga gactttaaga acctgaagaa ccttcacgca    1620
ttgattcttg tcaacaataa aattagcaaa gttagtcctg agcatttac accttggtg     1680 aagttggaac gactttatct gtccaagaat cagctgaagg aattgccaga aaaatgccc    1740 aaaactcttc aggagctgcg tgcccatgag aatgagatca ccaaagtgcg aaaagttact    1800
ttcaatggac tgaaccagat gattgtcata gaactgggca ccaatccgct gaagagctca    1860
ggaattgaaa atggggcttt ccagggaatg aagaagctct cctacatccg cattgctgat    1920
accaatatca ccagcattcc tcaaggtctt cctccttccc ttacggaatt acatcttgat    1980
ggcaacaaaa tcagcagagt tgatgcagct agcctgaaag gactgaataa tttggctaag    2040
ttgggattga gtttcaacag catctctgct gttgacaatg gctctctggc caacacgcct    2100
catctgaggg agcttcactt ggacaacaac aagcttacca gagtacctgg tgggctggca    2160
gagcataagt acatccaggt tgtctacctt cataacaaca atatctctgt agttggatca    2220
agtgacttct gcccacctgg acacaacacc aaaaaggctt cttattcggg tgtgagtctt    2280
ttcagcaacc cggtccagta ctgggagata cagccatcca ccttcagatg tgtctacgtg    2340
cgctctgcca ttcaactcgg aaactataag tga                                 2373
```

<210> SEQ ID NO 56
<211> LENGTH: 790
<212> TYPE: PRT
<213> ORGANISM: Artificial Sequence
<220> FEATURE:
<223> OTHER INFORMATION: synthetic
<400> SEQUENCE: 56

```
Met Met Ser Phe Val Ser Leu Leu Leu Val Gly Ile Leu Phe His Ala
1               5                   10                  15

Thr Gln Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ile Met Met Trp Val Arg Gln Ala Pro Gly Lys Gly Leu
    50                  55                  60

Glu Trp Val Ser Ser Ile Tyr Pro Ser Gly Gly Ile Thr Phe Tyr Ala
65                  70                  75                  80

Asp Thr Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ile Lys Leu Gly Thr Val Thr Thr Val Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
```

-continued

```
            195                 200                 205
Thr Val Pro Ser Ser Leu Gly Thr Gln Thr Tyr Ile Cys Asn Val
210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
                275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
450                 455                 460

Leu Ser Pro Gly Lys Ser Gly Gly Gly Gly Ser Asp Phe Glu Pro Ser
465                 470                 475                 480

Leu Gly Pro Val Cys Pro Phe Arg Cys Gln Cys His Leu Arg Val Val
                485                 490                 495

Gln Cys Ser Asp Leu Gly Leu Asp Lys Val Pro Lys Asp Leu Pro Pro
                500                 505                 510

Asp Thr Thr Leu Leu Asp Leu Gln Asn Asn Lys Ile Thr Glu Ile Lys
                515                 520                 525

Asp Gly Asp Phe Lys Asn Leu Lys Asn Leu His Ala Leu Ile Leu Val
                530                 535                 540

Asn Asn Lys Ile Ser Lys Val Ser Pro Gly Ala Phe Thr Pro Leu Val
545                 550                 555                 560

Lys Leu Glu Arg Leu Tyr Leu Ser Lys Asn Gln Leu Lys Glu Leu Pro
                565                 570                 575

Glu Lys Met Pro Lys Thr Leu Gln Glu Leu Arg Ala His Glu Asn Glu
                580                 585                 590

Ile Thr Lys Val Arg Lys Val Thr Phe Asn Gly Leu Asn Gln Met Ile
                595                 600                 605

Val Ile Glu Leu Gly Thr Asn Pro Leu Lys Ser Ser Gly Ile Glu Asn
610                 615                 620
```

Gly Ala Phe Gln Gly Met Lys Lys Leu Ser Tyr Ile Arg Ile Ala Asp
625                 630                 635                 640

Thr Asn Ile Thr Ser Ile Pro Gln Gly Leu Pro Pro Ser Leu Thr Glu
            645                 650                 655

Leu His Leu Asp Gly Asn Lys Ile Ser Arg Val Asp Ala Ala Ser Leu
        660                 665                 670

Lys Gly Leu Asn Asn Leu Ala Lys Leu Gly Leu Ser Phe Asn Ser Ile
    675                 680                 685

Ser Ala Val Asp Asn Gly Ser Leu Ala Asn Thr Pro His Leu Arg Glu
690                 695                 700

Leu His Leu Asp Asn Asn Lys Leu Thr Arg Val Pro Gly Gly Leu Ala
705                 710                 715                 720

Glu His Lys Tyr Ile Gln Val Val Tyr Leu His Asn Asn Asn Ile Ser
                725                 730                 735

Val Val Gly Ser Ser Asp Phe Cys Pro Pro Gly His Asn Thr Lys Lys
            740                 745                 750

Ala Ser Tyr Ser Gly Val Ser Leu Phe Ser Asn Pro Val Gln Tyr Trp
        755                 760                 765

Glu Ile Gln Pro Ser Thr Phe Arg Cys Val Tyr Val Arg Ser Ala Ile
    770                 775                 780

Gln Leu Gly Asn Tyr Lys
785                 790

<210> SEQ ID NO 57
<211> LENGTH: 3336
<212> TYPE: DNA
<213> ORGANISM: Artificial Sequence
<220> FEATURE:
<223> OTHER INFORMATION: synthetic

<400> SEQUENCE: 57
atgatgtcct ttgtctctct gctcctggtt ggcatcctat tccatgccac ccaggccgag     60
gtacagcttt tggagtcagg cggggggctc gtccaacctg gggggtcact ccggttgtca    120
tgtgctgcca gtggcttcac attctcatct tacattatga tgtgggttcg acaggccct    180 gggaaggggc tggagtgggt ttcctccatc taccccctccg ggggaattac cttctatgcc    240
gacacggtaa agggtcgctt cactataagt cgagataaca gcaaaaatac gctgtatctc    300
cagatgaact ctctcagggc tgaggacaca gctgtatatt actgcgcgcg gattaagttg    360
gggaccgtca acagtggaa ttactggggt caaggcactc tggtaaccgt atcctcagca    420
tccaccaagg gcccaagtgt attcccgctg gccccttcaa gtaaatccac gtctggcggc    480
acagccgctc tcggttgcct ggttaaggac tacttcccag aacctgtcac tgtcagttgg    540
aactcaggcg cattgacatc tggtgtccat acattccccg cagtcctgca aagctctgga    600
ctttacagtc ttagtagcgt agtgacagtc ccatcttcaa gtcttgggac ccaaacttat    660
atttgcaacg taaatcataa accctccaac actaaagtag acaaaaaagt agagccgaaa    720
tcttgcgaca aaacgcatac atgcccacca tgtcccgctc cggaactcct gggcggcccg    780 tccgttttc tctttccccc aaagcccaag gatacgctta tgatcagcag aacaccggaa    840
gttacttgtg tagtcgttga cgtgtctcac gaagatcccg aagtcaaatt taattggtat    900
gtggatggcg tcgaagtgca caacgcaaaa accaaaccca gagaggaaca gtataacagc    960
acgtatcgag tggtctccgt acttacggtc ctccaccagg actggttgaa tggcaaggag   1020
tacaagtgca aagtgagcaa taagcgttg ccagccccga tcgaaaaaac catcagcaag   1080

```
gccaagggac agcctagaga gccgcaggtt tacaccttgc cgccatcaag ggatgaactg    1140
actaaaaacc aggtatccct gacctgcctg gttaagggtt tttacccag tgatatagcg     1200 gttgaatggg agtctaacgg gcagccagag aacaactaca aaacgacacc tcccgttctg    1260
gattccgatg gcagcttttt cttgtattct aaactcaccg tggataaatc ccgatggcag    1320
caaggcaacg tcttctcctg cagcgtgatg catgaagcct tgcacaacca ctatacccaa    1380
aagagtctca gcctgtcacc cgggaaatcc ggggtggcg gatccgactt cgagccctcc    1440
ctaggcccag tgtgcccctt ccgctgtcaa tgccatcttc gagtggtcca gtgttctgat    1500
ttgggtctgg acaaagtgcc aaaggatctt ccccctgaca caactctgct agacctgcaa    1560
aacaacaaaa taaccgaaat caagatgga gactttaaga acctgaagaa ccttcacgca     1620
ttgattcttg tcaacaataa aattagcaaa gttagtcctg gagcatttac acctttggtg    1680
aagttggaac gactttatct gtccaagaat cagctgaagg aattgccaga aaaaatgccc    1740
aaaactcttc aggagctgcg tgcccatgag aatgagatca ccaaagtgcg aaaagttact    1800
ttcaatggac tgaaccagat gattgtcata gaactgggca ccaatccgct gaagagctca    1860
ggaattgaaa atgggctttt ccagggaatg aagaagctct cctacatccg cattgctgat    1920
accaatatca ccagcattcc tcaaggtctt cctccttccc ttacggaatt acatcttgat    1980
ggcaacaaaa tcagcagagt tgatgcagct agcctgaaag gactgaataa tttggctaag    2040
ttgggattga gtttcaacag catctctgct gttgacaatg gctctctggc caacacgcct    2100
catctgaggg agcttcactt ggacaacaac aagcttacca gagtacctgg tgggctggca    2160
gagcataagt acatccaggt tgtctacctt cataacaaca atatctctgt agttggatca    2220
agtgacttct gcccacctgg acacaacacc aaaaaggctt cttattcggg tgtgagtctt    2280
ttcagcaacc cggtccagta ctgggagata cagccatcca ccttcagatg tgtctacgtg    2340
cgctctgcca ttcaactcgg aaactataag tccgggggtg gcggatccga cttcgagccc    2400
tccctaggcc cagtgtgccc cttccgctgt caatgccatc ttcgagtggt ccagtgttct    2460
gatttgggtc tggacaaagt gccaaaggat cttccccctg acacaactct gctagacctg    2520
caaaacaaca aaataaccga aatcaaagat ggagacttta gaacctgaa gaaccttcac    2580 gcattgattc ttgtcaacaa taaaattagc aaagttagtc ctggagcatt tacacctttg    2640
gtgaagttgg aacgacttta tctgtccaag aatcagctga aggaattgcc agaaaaaatg    2700
cccaaaactc ttcaggagct gcgtgcccat gagaatgaga tcaccaaagt gcgaaaagtt    2760
actttcaatg gactgaacca gatgattgtc atagaactgg gcaccaatcc gctgaagagc    2820
tcaggaattg aaaatggggc tttccaggga atgaagaagc tctcctacat ccgcattgct    2880
gataccaata tcaccagcat tcctcaaggt cttcctcctt cccttacgga attacatctt    2940
gatggcaaca aaatcagcag agttgatgca gctagcctga aggactgaa taatttggct    3000 aagttgggat tgagtttcaa cagcatctct gctgttgaca atggctctct ggccaacacg    3060
cctcatctga gggagcttca cttggacaac aacaagctta ccagagtacc tggtgggctg    3120
gcagagcata gtacatcca ggttgtctac cttcataaca acaatatctc tgtagttgga    3180
tcaagtgact tctgcccacc tggacacaac accaaaaagg cttcttattc gggtgtgagt    3240
cttttcagca acccggtcca gtactgggag atacagccat ccaccttcag atgtgtctac    3300
gtgcgctctg ccattcaact cggaaactat aagtga                             3336
```

<210> SEQ ID NO 58

<211> LENGTH: 1111
<212> TYPE: PRT
<213> ORGANISM: Artificial Sequence
<220> FEATURE:
<223> OTHER INFORMATION: synthetic

<400> SEQUENCE: 58

Met Met Ser Phe Val Ser Leu Leu Leu Val Gly Ile Leu Phe His Ala
1               5                   10                  15

Thr Gln Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ile Met Met Trp Val Arg Gln Ala Pro Gly Lys Gly Leu
    50                  55                  60

Glu Trp Val Ser Ser Ile Tyr Pro Ser Gly Gly Ile Thr Phe Tyr Ala
65                  70                  75                  80

Asp Thr Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ile Lys Leu Gly Thr Val Thr Val Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

```
Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
    450                 455                 460

Leu Ser Pro Gly Lys Ser Gly Gly Gly Ser Asp Phe Glu Pro Ser
465                 470                 475                 480

Leu Gly Pro Val Cys Pro Phe Arg Cys Gln Cys His Leu Arg Val Val
                485                 490                 495

Gln Cys Ser Asp Leu Gly Leu Asp Lys Val Pro Lys Asp Leu Pro Pro
            500                 505                 510

Asp Thr Thr Leu Leu Asp Leu Gln Asn Asn Lys Ile Thr Glu Ile Lys
        515                 520                 525

Asp Gly Asp Phe Lys Asn Leu Lys Asn Leu His Ala Leu Ile Leu Val
    530                 535                 540

Asn Asn Lys Ile Ser Lys Val Ser Pro Gly Ala Phe Thr Pro Leu Val
545                 550                 555                 560

Lys Leu Glu Arg Leu Tyr Leu Ser Lys Asn Gln Leu Lys Glu Leu Pro
                565                 570                 575

Glu Lys Met Pro Lys Thr Leu Gln Glu Leu Arg Ala His Glu Asn Glu
            580                 585                 590

Ile Thr Lys Val Arg Lys Val Thr Phe Asn Gly Leu Asn Gln Met Ile
        595                 600                 605

Val Ile Glu Leu Gly Thr Asn Pro Leu Lys Ser Ser Gly Ile Glu Asn
    610                 615                 620

Gly Ala Phe Gln Gly Met Lys Lys Leu Ser Tyr Ile Arg Ile Ala Asp
625                 630                 635                 640

Thr Asn Ile Thr Ser Ile Pro Gln Gly Leu Pro Pro Ser Leu Thr Glu
                645                 650                 655

Leu His Leu Asp Gly Asn Lys Ile Ser Arg Val Asp Ala Ala Ser Leu
            660                 665                 670

Lys Gly Leu Asn Asn Leu Ala Lys Leu Gly Leu Ser Phe Asn Ser Ile
            675                 680                 685

Ser Ala Val Asp Asn Gly Ser Leu Ala Asn Thr Pro His Leu Arg Glu
    690                 695                 700

Leu His Leu Asp Asn Asn Lys Leu Thr Arg Val Pro Gly Gly Leu Ala
705                 710                 715                 720

Glu His Lys Tyr Ile Gln Val Val Tyr Leu His Asn Asn Asn Ile Ser
                725                 730                 735

Val Val Gly Ser Ser Asp Phe Cys Pro Pro Gly His Asn Thr Lys Lys
            740                 745                 750

Ala Ser Tyr Ser Gly Val Ser Leu Phe Ser Asn Pro Val Gln Tyr Trp
            755                 760                 765

Glu Ile Gln Pro Ser Thr Phe Arg Cys Val Tyr Val Arg Ser Ala Ile
        770                 775                 780

Gln Leu Gly Asn Tyr Lys Ser Gly Gly Gly Ser Asp Phe Glu Pro
785                 790                 795                 800
```

Ser Leu Gly Pro Val Cys Pro Phe Arg Cys Gln Cys His Leu Arg Val
                    805                 810                 815

Val Gln Cys Ser Asp Leu Gly Leu Asp Lys Val Pro Lys Asp Leu Pro
            820                 825                 830

Pro Asp Thr Thr Leu Leu Asp Leu Gln Asn Asn Lys Ile Thr Glu Ile
        835                 840                 845

Lys Asp Gly Asp Phe Lys Asn Leu Lys Asn Leu His Ala Leu Ile Leu
    850                 855                 860

Val Asn Asn Lys Ile Ser Lys Val Ser Pro Gly Ala Phe Thr Pro Leu
865                 870                 875                 880

Val Lys Leu Glu Arg Leu Tyr Leu Ser Lys Asn Gln Leu Lys Glu Leu
                885                 890                 895

Pro Glu Lys Met Pro Lys Thr Leu Gln Glu Leu Arg Ala His Glu Asn
            900                 905                 910

Glu Ile Thr Lys Val Arg Lys Val Thr Phe Asn Gly Leu Asn Gln Met
        915                 920                 925

Ile Val Ile Glu Leu Gly Thr Asn Pro Leu Lys Ser Ser Gly Ile Glu
    930                 935                 940

Asn Gly Ala Phe Gln Gly Met Lys Lys Leu Ser Tyr Ile Arg Ile Ala
945                 950                 955                 960

Asp Thr Asn Ile Thr Ser Ile Pro Gln Gly Leu Pro Pro Ser Leu Thr
                965                 970                 975

Glu Leu His Leu Asp Gly Asn Lys Ile Ser Arg Val Asp Ala Ala Ser
            980                 985                 990

Leu Lys Gly Leu Asn Asn Leu Ala Lys Leu Gly Leu Ser Phe Asn Ser
        995                 1000                1005

Ile Ser Ala Val Asp Asn Gly Ser Leu Ala Asn Thr Pro His Leu
    1010                1015                1020

Arg Glu Leu His Leu Asp Asn Asn Lys Leu Thr Arg Val Pro Gly
    1025                1030                1035

Gly Leu Ala Glu His Lys Tyr Ile Gln Val Val Tyr Leu His Asn
    1040                1045                1050

Asn Asn Ile Ser Val Val Gly Ser Ser Asp Phe Cys Pro Pro Gly
    1055                1060                1065

His Asn Thr Lys Lys Ala Ser Tyr Ser Gly Val Ser Leu Phe Ser
    1070                1075                1080

Asn Pro Val Gln Tyr Trp Glu Ile Gln Pro Ser Thr Phe Arg Cys
    1085                1090                1095

Val Tyr Val Arg Ser Ala Ile Gln Leu Gly Asn Tyr Lys
    1100                1105                1110

<210> SEQ ID NO 59
<211> LENGTH: 1746
<212> TYPE: DNA
<213> ORGANISM: Artificial Sequence
<220> FEATURE:
<223> OTHER INFORMATION: synthetic

<400> SEQUENCE: 59
atgatgtcct tgtctctct gctcctggtt ggcatcctat tccatgccac ccaggccgag     60
gtacagcttt tggagtcagg cggggggctc gtccaacctg ggggtcact ccggttgtca    120 tgtgctgcca gtggcttcac attctcatct tacattatga tgtgggttcg acaggcccct    180
gggaaggggc tggagtgggt ttcctccatc tacccctccg ggggaattac cttctatgcc    240
gacacggtaa aggtcgctt cactataagt cgagataaca gcaaaaatac gctgtatctc    300

```
cagatgaact ctctcagggc tgaggacaca gctgtatatt actgcgcgcg gattaagttg    360
gggaccgtca caacagtgga ttactggggt caaggcactc tggtaaccgt atcctcagca    420
tccaccaagg gcccaagtgt attcccgctg gccccttcaa gtaaatccac gtctggcggc    480
acagccgctc tcggttgcct ggttaaggac tacttcccag aacctgtcac tgtcagttgg    540
aactcaggcg cattgacatc tggtgtccat acattcccg cagtcctgca agctctgga    600 ctttacagtc ttagtagcgt agtgacagtc ccatcttcaa gtcttgggac ccaaacttat    660
atttgcaacg taaatcataa accctccaac actaaagtag acaaaaaagt agagccgaaa    720
tcttgcgaca aaacgcatac atgcccacca tgtcccgctc cggaactcct gggcggcccg    780 tccgttttc tctttccccc aaagcccaag gatacgctta tgatcagcag aacaccggaa    840
gttacttgtg tagtcgttga cgtgtctcac gaagatcccg aagtcaaatt taattggtat    900
gtggatggcg tcgaagtgca caacgcaaaa accaaaccca gagaggaaca gtataacagc    960
acgtatcgag tggtctccgt acttacggtc ctccaccagg actggttgaa tggcaaggag   1020
tacaagtgca agtgagcaa taaagcgttg ccagccccga tcgaaaaaac catcagcaag   1080
gccaagggac agcctagaga ccgcaggtt tacaccttgc cgccatcaag ggatgaactg   1140
actaaaaacc aggtatccct gacctgcctg gttaagggtt tttaccccag tgatatagcg   1200
gttgaatggg agtctaacgg gcagccagag aacaactaca aaacgacacc tcccgttctg   1260
gattccgatg gcagcttttt cttgtattct aaactcaccg tggataaatc ccgatggcag   1320
caaggcaacg tcttctcctg cagcgtgatg catgaagcct gcacaaacca ctataccca    1380 aagagtctca gcctgtcacc cgggaaatcc gggggtggcg gatccctgcg tgcccatgag   1440
aatgagatca ccaaagtgcg aaaagttact ttcaatggac tgaaccagat gattgtcata   1500
gaactgggca ccaatccgct gaagagctca ggaattgaaa atggggcttt ccagggaatg   1560
aagaagctct cctacatccg cattgctgat accaatatca ccagcattcc tcaaggtctt   1620
cctccttccc ttacggaatt acatcttgat ggcaacaaaa tcagcagagt tgatgcagct   1680
agcctgaaag gactgaataa tttggctaag ttgggattga gtttcaacag catctctgct   1740
gtttga                                                              1746
```

<210> SEQ ID NO 60
<211> LENGTH: 581
<212> TYPE: PRT
<213> ORGANISM: Artificial Sequence
<220> FEATURE:
<223> OTHER INFORMATION: synthetic

<400> SEQUENCE: 60

```
Met Met Ser Phe Val Ser Leu Leu Leu Val Gly Ile Leu Phe His Ala
1               5                   10                  15

Thr Gln Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ile Met Met Trp Val Arg Gln Ala Pro Gly Lys Gly Leu
    50                  55                  60

Glu Trp Val Ser Ser Ile Tyr Pro Ser Gly Gly Ile Thr Phe Tyr Ala
65                  70                  75                  80

Asp Thr Val Lys Gly Arg Phe Thr Ile Ser Arg Asp Asn Ser Lys Asn
                85                  90                  95
```

```
Thr Leu Tyr Leu Gln Met Asn Ser Leu Arg Ala Glu Asp Thr Ala Val
            100                 105                 110

Tyr Tyr Cys Ala Arg Ile Lys Leu Gly Thr Val Thr Thr Val Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys Ser Gly Gly Gly Ser Leu Arg Ala His Glu
465                 470                 475                 480

Asn Glu Ile Thr Lys Val Arg Lys Val Thr Phe Asn Gly Leu Asn Gln
                485                 490                 495

Met Ile Val Ile Glu Leu Gly Thr Asn Pro Leu Lys Ser Ser Gly Ile
            500                 505                 510

Glu Asn Gly Ala Phe Gln Gly Met Lys Lys Leu Ser Tyr Ile Arg Ile
```

```
            515                 520                 525
Ala Asp Thr Asn Ile Thr Ser Ile Pro Gln Gly Leu Pro Pro Ser Leu
    530                 535                 540

Thr Glu Leu His Leu Asp Gly Asn Lys Ile Ser Arg Val Asp Ala Ala
545                 550                 555                 560

Ser Leu Lys Gly Leu Asn Asn Leu Ala Lys Leu Gly Leu Ser Phe Asn
                565                 570                 575

Ser Ile Ser Ala Val
            580

<210> SEQ ID NO 61
<211> LENGTH: 2082
<212> TYPE: DNA
<213> ORGANISM: Artificial Sequence
<220> FEATURE:
<223> OTHER INFORMATION: synthetic

<400> SEQUENCE: 61
```

| | | | | | |
|---|---|---|---|---|---|
| atgatgtcct | ttgtctctct | gctcctggtt | ggcatcctat | tccatgccac | ccaggccgag | 60 |
| gtacagcttt | tggagtcagg | cggggggctc | gtccaacctg | gggggtcact | ccggttgtca | 120 |
| tgtgctgcca | gtggcttcac | attctcatct | tacattatga | tgtgggttcg | acaggccct | 180 |
| gggaaggggc | tggagtgggt | ttcctccatc | taccctccg | gggaattac | cttctatgcc | 240 |
| gacacggtaa | agggtcgctt | cactataagt | cgagataaca | gcaaaaatac | gctgtatctc | 300 |
| cagatgaact | ctctcagggc | tgaggacaca | gctgtatatt | actgcgcgcg | gattaagttg | 360 |
| gggaccgtca | caacagtgga | ttactgggt | caaggcactc | tggtaaccgt | atcctcagca | 420 |
| tccaccaagg | gcccaagtgt | attcccgctg | gccccttcaa | gtaaatccac | gtctggcggc | 480 |
| acagccgctc | tcggttgcct | ggttaaggac | tacttcccag | aacctgtcac | tgtcagttgg | 540 |
| aactcaggcg | cattgacatc | tggtgtccat | acattcccg | cagtcctgca | aagctctgga | 600 |
| ctttacagtc | ttagtagcgt | agtgacagtc | ccatcttcaa | gtcttgggac | ccaaacttat | 660 |
| atttgcaacg | taaatcataa | accctccaac | actaaagtag | acaaaaaagt | agagccgaaa | 720 |
| tcttgcgaca | aaacgcatac | atgcccacca | tgtcccgctc | cggaactcct | gggcggcccg | 780 |
| tccgttttc | tctttccccc | aaagcccaag | gatacgctta | tgatcagcag | aacaccggaa | 840 |
| gttacttgtg | tagtcgttga | cgtgtctcac | gaagatcccg | aagtcaaatt | taattggtat | 900 |
| gtggatggcg | tcgaagtgca | caacgcaaaa | accaaaccca | gagaggaaca | gtataacagc | 960 |
| acgtatcgag | tggtctccgt | acttacggtc | ctccaccagg | actggttgaa | tggcaaggag | 1020 |
| tacaagtgca | aagtgagcaa | taagcgttg | ccagccccga | tcgaaaaaac | catcagcaag | 1080 |
| gccaagggac | agcctagaga | gccgcaggtt | tacaccttgc | cgccatcaag | ggatgaactg | 1140 |
| actaaaaacc | aggtatccct | gacctgcctg | gttaagggtt | tttaccccag | tgatatagcg | 1200 |
| gttgaatggg | agtctaacgg | gcagccagag | aacaactaca | aaacgacacc | tcccgttctg | 1260 |
| gattccgatg | gcagctttttt | cttgtattct | aaactcaccg | tggataaatc | ccgatggcag | 1320 |
| caaggcaacg | tcttctcctg | cagcgtgatg | catgaagcct | tgcacaacca | ctatacccaa | 1380 |
| aagagtctca | gcctgtcacc | cgggaaatcc | gggggtggcg | gatccctgcg | tgcccatgag | 1440 |
| aatgagatca | ccaaagtgcg | aaaagttact | ttcaatggac | tgaaccagat | gattgtcata | 1500 |
| gaactgggca | ccaatccgct | gaagagctca | ggaattgaaa | atggggcttt | ccagggaatg | 1560 |
| aagaagctct | cctacatccg | cattgctgat | accaatatca | ccagcattcc | tcaaggtctt | 1620 |
| cctccttccc | ttacggaatt | acatcttgat | ggcaacaaaa | tcagcagagt | tgatgcagct | 1680 |

-continued

```
agcctgaaag gactgaataa tttggctaag ttgggattga gtttcaacag catctctgct   1740
gtttccgggg gtggcggatc cctgcgtgcc catgagaatg agatcaccaa agtgcgaaaa   1800
gttactttca atggactgaa ccagatgatt gtcatagaac tgggcaccaa tccgctgaag   1860
agctcaggaa ttgaaaatgg ggcttttcag ggaatgaaga agctctccta catccgcatt   1920
gctgatacca atatccaccag cattcctcaa ggtcttcctc cttcccttac ggaattacat   1980
cttgatggca acaaaatcag cagagttgat gcagctagcc tgaaaggact gaataatttg   2040
gctaagttgg gattgagttt caacagcatc tctgctgttt ga                      2082
```

<210> SEQ ID NO 62
<211> LENGTH: 693
<212> TYPE: PRT
<213> ORGANISM: Artificial Sequence
<220> FEATURE:
<223> OTHER INFORMATION: synthetic

<400> SEQUENCE: 62

```
Met Met Ser Phe Val Ser Leu Leu Leu Val Gly Ile Leu Phe His Ala
1               5                   10                  15

Thr Gln Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ile Met Met Trp Val Arg Gln Ala Pro Gly Lys Gly Leu
    50                  55                  60

Glu Trp Val Ser Ser Ile Tyr Pro Ser Gly Gly Ile Thr Phe Tyr Ala
65                  70                  75                  80

Asp Thr Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ile Lys Leu Gly Thr Val Thr Thr Val Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285
```

```
Ser His Glu Asp Pro Glu Val Lys Phe Asn Trp Tyr Val Asp Gly Val
    290                 295                 300
Glu Val His Asn Ala Lys Thr Lys Pro Arg Glu Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
        355                 360                 365
Gln Val Tyr Thr Leu Pro Pro Ser Arg Asp Glu Leu Thr Lys Asn Gln
370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Gly Asn Val Phe Ser Cys Ser
        435                 440                 445
Val Met His Glu Ala Leu His Asn His Tyr Thr Gln Lys Ser Leu Ser
450                 455                 460
Leu Ser Pro Gly Lys Ser Gly Gly Gly Ser Leu Arg Ala His Glu
465                 470                 475                 480
Asn Glu Ile Thr Lys Val Arg Lys Val Thr Phe Asn Gly Leu Asn Gln
                485                 490                 495
Met Ile Val Ile Glu Leu Gly Thr Asn Pro Leu Lys Ser Ser Gly Ile
            500                 505                 510
Glu Asn Gly Ala Phe Gln Gly Met Lys Lys Leu Ser Tyr Ile Arg Ile
        515                 520                 525
Ala Asp Thr Asn Ile Thr Ser Ile Pro Gln Gly Leu Pro Pro Ser Leu
            530                 535                 540
Thr Glu Leu His Leu Asp Gly Asn Lys Ile Ser Arg Val Asp Ala Ala
545                 550                 555                 560
Ser Leu Lys Gly Leu Asn Asn Leu Ala Lys Leu Gly Leu Ser Phe Asn
                565                 570                 575
Ser Ile Ser Ala Val Ser Gly Gly Gly Ser Leu Arg Ala His Glu
            580                 585                 590
Asn Glu Ile Thr Lys Val Arg Lys Val Thr Phe Asn Gly Leu Asn Gln
        595                 600                 605
Met Ile Val Ile Glu Leu Gly Thr Asn Pro Leu Lys Ser Ser Gly Ile
            610                 615                 620
Glu Asn Gly Ala Phe Gln Gly Met Lys Lys Leu Ser Tyr Ile Arg Ile
625                 630                 635                 640
Ala Asp Thr Asn Ile Thr Ser Ile Pro Gln Gly Leu Pro Pro Ser Leu
                645                 650                 655
Thr Glu Leu His Leu Asp Gly Asn Lys Ile Ser Arg Val Asp Ala Ala
            660                 665                 670
Ser Leu Lys Gly Leu Asn Asn Leu Ala Lys Leu Gly Leu Ser Phe Asn
        675                 680                 685
Ser Ile Ser Ala Val
    690
```

<210> SEQ ID NO 63
<211> LENGTH: 315
<212> TYPE: PRT
<213> ORGANISM: Artificial Sequence
<220> FEATURE:
<223> OTHER INFORMATION: synthetic

<400> SEQUENCE: 63

Asp Phe Glu Pro Ser Leu Gly Pro Val Cys Pro Phe Arg Cys Gln Cys
1               5                   10                  15

His Leu Arg Val Val Gln Cys Ser Asp Leu Gly Leu Asp Lys Val Pro
            20                  25                  30

Lys Asp Leu Pro Pro Asp Thr Thr Leu Leu Asp Leu Gln Asn Asn Lys
        35                  40                  45

Ile Thr Glu Ile Lys Asp Gly Asp Phe Lys Asn Leu Lys Asn Leu His
    50                  55                  60

Ala Leu Ile Leu Val Asn Asn Lys Ile Ser Lys Val Ser Pro Gly Ala
65                  70                  75                  80

Phe Thr Pro Leu Val Lys Leu Glu Arg Leu Tyr Leu Ser Lys Asn Gln
                85                  90                  95

Leu Lys Glu Leu Pro Glu Lys Met Pro Lys Thr Leu Gln Glu Leu Arg
            100                 105                 110

Ala His Glu Asn Glu Ile Thr Lys Val Arg Lys Val Thr Phe Asn Gly
        115                 120                 125

Leu Asn Gln Met Ile Val Ile Glu Leu Gly Thr Asn Pro Leu Lys Ser
    130                 135                 140

Ser Gly Ile Glu Asn Gly Ala Phe Gln Gly Met Lys Lys Leu Ser Tyr
145                 150                 155                 160

Ile Arg Ile Ala Asp Thr Asn Ile Thr Ser Ile Pro Gln Gly Leu Pro
                165                 170                 175

Pro Ser Leu Thr Glu Leu His Leu Asp Gly Asn Lys Ile Ser Arg Val
            180                 185                 190

Asp Ala Ala Ser Leu Lys Gly Leu Asn Asn Leu Ala Lys Leu Gly Leu
        195                 200                 205

Ser Phe Asn Ser Ile Ser Ala Val Asp Asn Gly Ser Leu Ala Asn Thr
    210                 215                 220

Pro His Leu Arg Glu Leu His Leu Asp Asn Asn Lys Leu Thr Arg Val
225                 230                 235                 240

Pro Gly Gly Leu Ala Glu His Lys Tyr Ile Gln Val Val Tyr Leu His
                245                 250                 255

Asn Asn Asn Ile Ser Val Val Gly Ser Ser Asp Phe Cys Pro Pro Gly
            260                 265                 270

His Asn Thr Lys Lys Ala Ser Tyr Ser Gly Val Ser Leu Phe Ser Asn
        275                 280                 285

Pro Val Gln Tyr Trp Glu Ile Gln Pro Ser Thr Phe Arg Cys Val Tyr
    290                 295                 300

Val Arg Ser Ala Ile Gln Leu Gly Asn Tyr Lys
305                 310                 315

<210> SEQ ID NO 64
<211> LENGTH: 636
<212> TYPE: PRT
<213> ORGANISM: Artificial Sequence
<220> FEATURE:
<223> OTHER INFORMATION: synthetic

<400> SEQUENCE: 64

```
Asp Phe Glu Pro Ser Leu Gly Pro Val Cys Pro Phe Arg Cys Gln Cys
1               5                   10                  15

His Leu Arg Val Val Gln Cys Ser Asp Leu Gly Leu Asp Lys Val Pro
            20                  25                  30

Lys Asp Leu Pro Pro Asp Thr Thr Leu Leu Asp Leu Gln Asn Asn Lys
            35                  40                  45

Ile Thr Glu Ile Lys Asp Gly Asp Phe Lys Asn Leu Lys Asn Leu His
50                  55                  60

Ala Leu Ile Leu Val Asn Asn Lys Ile Ser Lys Val Ser Pro Gly Ala
65                  70                  75                  80

Phe Thr Pro Leu Val Lys Leu Glu Arg Leu Tyr Leu Ser Lys Asn Gln
            85                  90                  95

Leu Lys Glu Leu Pro Glu Lys Met Pro Lys Thr Leu Gln Glu Leu Arg
            100                 105                 110

Ala His Glu Asn Glu Ile Thr Lys Val Arg Lys Val Thr Phe Asn Gly
            115                 120                 125

Leu Asn Gln Met Ile Val Ile Glu Leu Gly Thr Asn Pro Leu Lys Ser
            130                 135                 140

Ser Gly Ile Glu Asn Gly Ala Phe Gln Gly Met Lys Lys Leu Ser Tyr
145                 150                 155                 160

Ile Arg Ile Ala Asp Thr Asn Ile Thr Ser Ile Pro Gln Gly Leu Pro
            165                 170                 175

Pro Ser Leu Thr Glu Leu His Leu Asp Gly Asn Lys Ile Ser Arg Val
            180                 185                 190

Asp Ala Ala Ser Leu Lys Gly Leu Asn Asn Leu Ala Lys Leu Gly Leu
            195                 200                 205

Ser Phe Asn Ser Ile Ser Ala Val Asp Asn Gly Ser Leu Ala Asn Thr
210                 215                 220

Pro His Leu Arg Glu Leu His Leu Asp Asn Asn Lys Leu Thr Arg Val
225                 230                 235                 240

Pro Gly Gly Leu Ala Glu His Lys Tyr Ile Gln Val Val Tyr Leu His
            245                 250                 255

Asn Asn Asn Ile Ser Val Val Gly Ser Ser Asp Phe Cys Pro Pro Gly
            260                 265                 270

His Asn Thr Lys Lys Ala Ser Tyr Ser Gly Val Ser Leu Phe Ser Asn
            275                 280                 285

Pro Val Gln Tyr Trp Glu Ile Gln Pro Ser Thr Phe Arg Cys Val Tyr
            290                 295                 300

Val Arg Ser Ala Ile Gln Leu Gly Asn Tyr Lys Ser Gly Gly Gly Gly
305                 310                 315                 320

Ser Asp Phe Glu Pro Ser Leu Gly Pro Val Cys Pro Phe Arg Cys Gln
            325                 330                 335

Cys His Leu Arg Val Val Gln Cys Ser Asp Leu Gly Leu Asp Lys Val
            340                 345                 350

Pro Lys Asp Leu Pro Pro Asp Thr Thr Leu Leu Asp Leu Gln Asn Asn
            355                 360                 365

Lys Ile Thr Glu Ile Lys Asp Gly Asp Phe Lys Asn Leu Lys Asn Leu
            370                 375                 380

His Ala Leu Ile Leu Val Asn Asn Lys Ile Ser Lys Val Ser Pro Gly
385                 390                 395                 400

Ala Phe Thr Pro Leu Val Lys Leu Glu Arg Leu Tyr Leu Ser Lys Asn
            405                 410                 415

Gln Leu Lys Glu Leu Pro Glu Lys Met Pro Lys Thr Leu Gln Glu Leu
```

```
                420                 425                 430
Arg Ala His Glu Asn Glu Ile Thr Lys Val Arg Lys Val Thr Phe Asn
        435                 440                 445

Gly Leu Asn Gln Met Ile Val Ile Glu Leu Gly Thr Asn Pro Leu Lys
    450                 455                 460

Ser Ser Gly Ile Glu Asn Gly Ala Phe Gln Gly Met Lys Lys Leu Ser
465                 470                 475                 480

Tyr Ile Arg Ile Ala Asp Thr Asn Ile Thr Ser Ile Pro Gln Gly Leu
                485                 490                 495

Pro Pro Ser Leu Thr Glu Leu His Leu Asp Gly Asn Lys Ile Ser Arg
            500                 505                 510

Val Asp Ala Ala Ser Leu Lys Gly Leu Asn Asn Leu Ala Lys Leu Gly
        515                 520                 525

Leu Ser Phe Asn Ser Ile Ser Ala Val Asp Asn Gly Ser Leu Ala Asn
    530                 535                 540

Thr Pro His Leu Arg Glu Leu His Leu Asp Asn Asn Lys Leu Thr Arg
545                 550                 555                 560

Val Pro Gly Gly Leu Ala Glu His Lys Tyr Ile Gln Val Val Tyr Leu
                565                 570                 575

His Asn Asn Asn Ile Ser Val Val Gly Ser Ser Asp Phe Cys Pro Pro
            580                 585                 590

Gly His Asn Thr Lys Lys Ala Ser Tyr Ser Gly Val Ser Leu Phe Ser
        595                 600                 605

Asn Pro Val Gln Tyr Trp Glu Ile Gln Pro Ser Thr Phe Arg Cys Val
    610                 615                 620

Tyr Val Arg Ser Ala Ile Gln Leu Gly Asn Tyr Lys
625                 630                 635

<210> SEQ ID NO 65
<211> LENGTH: 106
<212> TYPE: PRT
<213> ORGANISM: Artificial Sequence
<220> FEATURE:
<223> OTHER INFORMATION: synthetic

<400> SEQUENCE: 65

Leu Arg Ala His Glu Asn Glu Ile Thr Lys Val Arg Lys Val Thr Phe
1               5                   10                  15

Asn Gly Leu Asn Gln Met Ile Val Ile Glu Leu Gly Thr Asn Pro Leu
            20                  25                  30

Lys Ser Ser Gly Ile Glu Asn Gly Ala Phe Gln Gly Met Lys Lys Leu
        35                  40                  45

Ser Tyr Ile Arg Ile Ala Asp Thr Asn Ile Thr Ser Ile Pro Gln Gly
    50                  55                  60

Leu Pro Pro Ser Leu Thr Glu Leu His Leu Asp Gly Asn Lys Ile Ser
65                  70                  75                  80

Arg Val Asp Ala Ala Ser Leu Lys Gly Leu Asn Asn Leu Ala Lys Leu
                85                  90                  95

Gly Leu Ser Phe Asn Ser Ile Ser Ala Val
            100                 105

<210> SEQ ID NO 66
<211> LENGTH: 218
<212> TYPE: PRT
<213> ORGANISM: Artificial Sequence
<220> FEATURE:
<223> OTHER INFORMATION: synthetic
```

-continued

```
<400> SEQUENCE: 66

Leu Arg Ala His Glu Asn Glu Ile Thr Lys Val Arg Lys Val Thr Phe
1               5                   10                  15

Asn Gly Leu Asn Gln Met Ile Val Ile Glu Leu Gly Thr Asn Pro Leu
            20                  25                  30

Lys Ser Ser Gly Ile Glu Asn Gly Ala Phe Gln Gly Met Lys Lys Leu
        35                  40                  45

Ser Tyr Ile Arg Ile Ala Asp Thr Asn Ile Thr Ser Ile Pro Gln Gly
    50                  55                  60

Leu Pro Pro Ser Leu Thr Glu Leu His Leu Asp Gly Asn Lys Ile Ser
65                  70                  75                  80

Arg Val Asp Ala Ala Ser Leu Lys Gly Leu Asn Asn Leu Ala Lys Leu
            85                  90                  95

Gly Leu Ser Phe Asn Ser Ile Ser Ala Val Ser Gly Gly Gly Gly Ser
                100                 105                 110

Leu Arg Ala His Glu Asn Glu Ile Thr Lys Val Arg Lys Val Thr Phe
            115                 120                 125

Asn Gly Leu Asn Gln Met Ile Val Ile Glu Leu Gly Thr Asn Pro Leu
        130                 135                 140

Lys Ser Ser Gly Ile Glu Asn Gly Ala Phe Gln Gly Met Lys Lys Leu
145                 150                 155                 160

Ser Tyr Ile Arg Ile Ala Asp Thr Asn Ile Thr Ser Ile Pro Gln Gly
                165                 170                 175

Leu Pro Pro Ser Leu Thr Glu Leu His Leu Asp Gly Asn Lys Ile Ser
            180                 185                 190

Arg Val Asp Ala Ala Ser Leu Lys Gly Leu Asn Asn Leu Ala Lys Leu
        195                 200                 205

Gly Leu Ser Phe Asn Ser Ile Ser Ala Val
            210                 215
```